United States Patent
Iida et al.

(10) Patent No.: US 6,881,315 B2
(45) Date of Patent: Apr. 19, 2005

(54) FRACTIONATING APPARATUS HAVING COLONIES OF PILLARS ARRANGED IN MIGRATION PASSAGE AT INTERVAL AND PROCESS FOR FABRICATING PILLARS

(75) Inventors: Kazuhiro Iida, Tokyo (JP); Hisao Kawaura, Tokyo (JP); Masakazu Baba, Tokyo (JP); Toshitsugu Sakamoto, Tokyo (JP); Toru Sano, Tokyo (JP); Noriyuki Iguchi, Tokyo (JP)

(73) Assignee: NEC Corporation, Tokyo (JP)

( * ) Notice: Subject to any disclaimer, the term of this patent is extended or adjusted under 35 U.S.C. 154(b) by 163 days.

(21) Appl. No.: 10/207,852

(22) Filed: Jul. 31, 2002

(65) Prior Publication Data

US 2003/0049563 A1 Mar. 13, 2003

(30) Foreign Application Priority Data

Aug. 3, 2001 (JP) .................................. 2001-237181
Sep. 10, 2001 (JP) .................................. 2001-272900
May 15, 2002 (JP) .................................. 2002-140777

(51) Int. Cl.⁷ .............................................. C07K 1/26
(52) U.S. Cl. ................... 204/600; 204/164; 204/549; 204/450; 430/311; 435/287.3; 435/283.1
(58) Field of Search ................... 204/164, 549, 204/450, 600; 430/311; 435/287.3, 283.1

(56) References Cited

U.S. PATENT DOCUMENTS 5,427,663 A * 6/1995 Austin et al. ............... 204/549
5,837,115 A    11/1998 Austin et al.

FOREIGN PATENT DOCUMENTS

| JP | 10-506991    | 7/1998 |
| JP | 2002-233792  | 8/2002 |
| JP | 2002-239317  | 8/2002 |
| WO | WO99/09042   | 2/1999 |

OTHER PUBLICATIONS

Japanese Office Action dated Jun. 1, 2004.

* cited by examiner

Primary Examiner—John A. McPherson
Assistant Examiner—Daborah Chacko-Davis
(74) Attorney, Agent, or Firm—Sughrue Mion, PLLC

(57) ABSTRACT

A fractionating apparatus is used for fractionating sample into micro-structures different in size, and includes a fractionating unit formed with a fractionating passage; the fractionating passage is defined in a groove formed in a substrate of the fractionating unit, and pillar patches are formed in the groove at intervals wider than the gap among the pillar patches; while the sample is migrated through the fractionating passage, small-sized DNA molecules are trapped in the pillar patches, and large-sized DNA molecules are smoothly migrated through the wide intervals; this results in that the large-sized DNA molecules reaches the end of the fractionating passage faster than the small-sized DNA molecules without clogging.

28 Claims, 48 Drawing Sheets

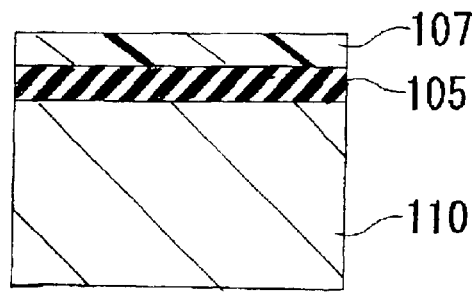
Fig. 2 9 A
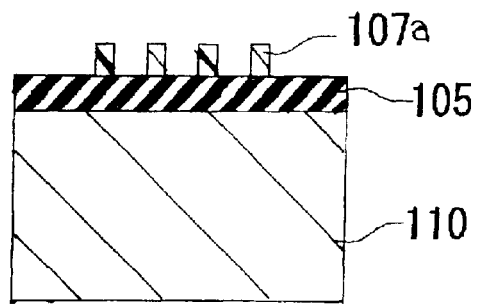
Fig. 2 9 B
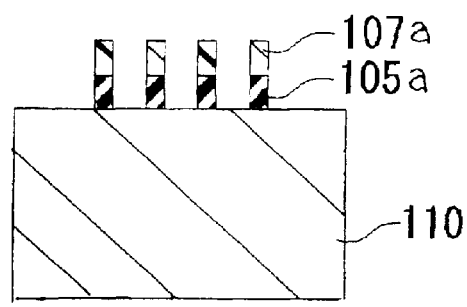
Fig. 2 9 C
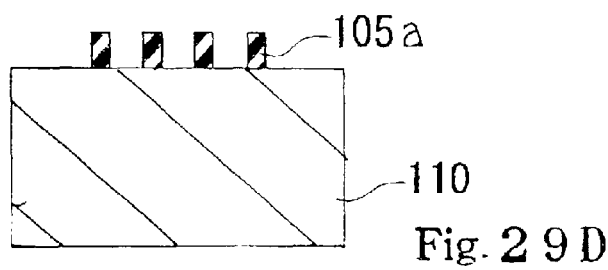
Fig. 2 9 D

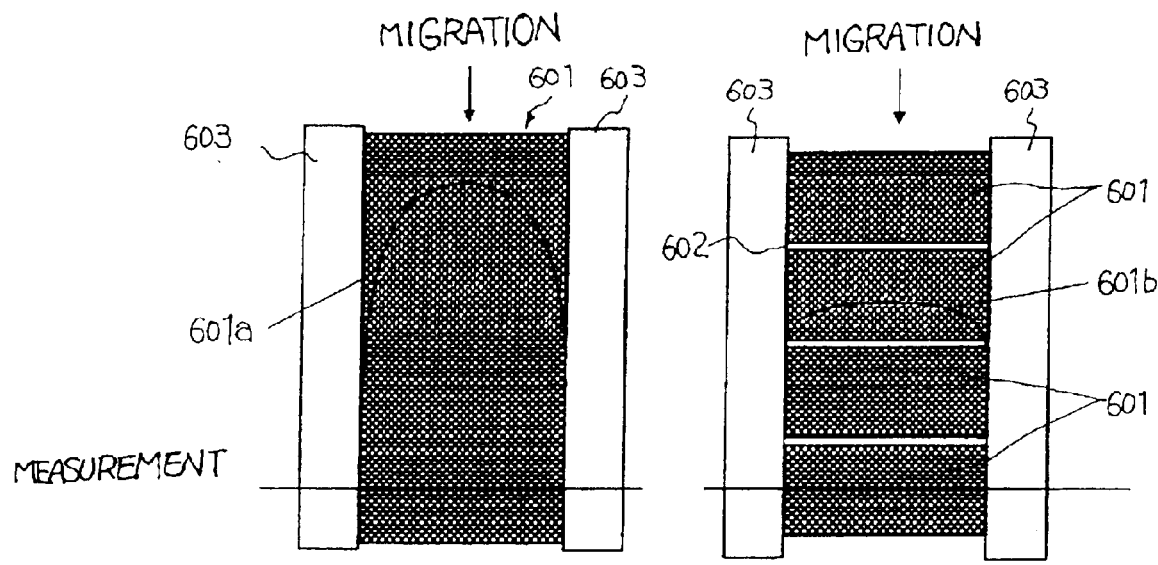
Fig. 3 5 A  Fig. 3 5 B
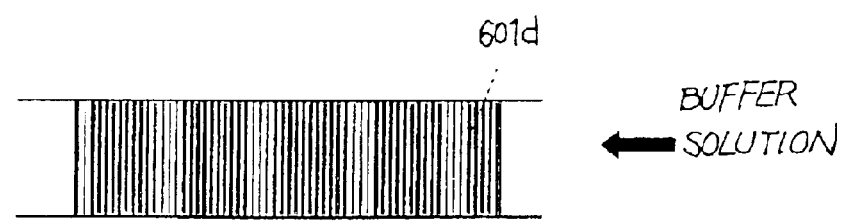
Fig. 3 6 A
Fig. 3 6 B
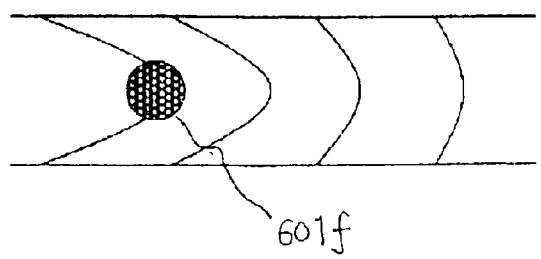
Fig. 3 6 C

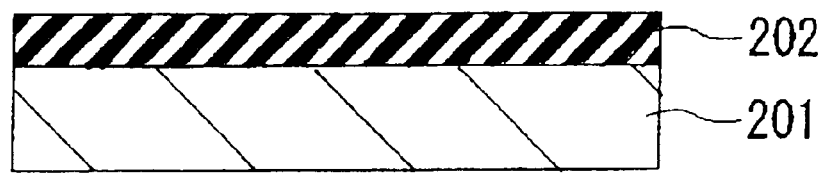
Fig. 5 1 A
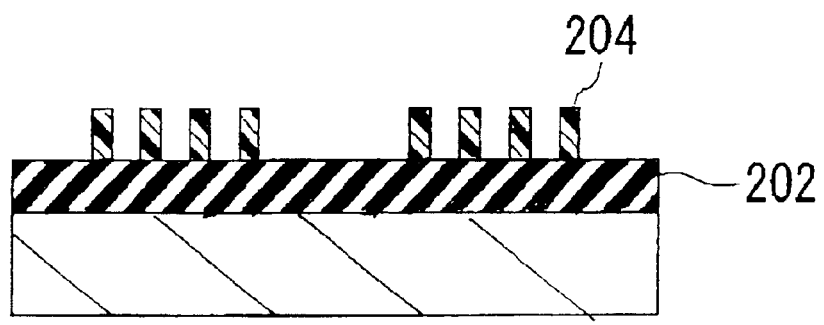
Fig. 5 1 B
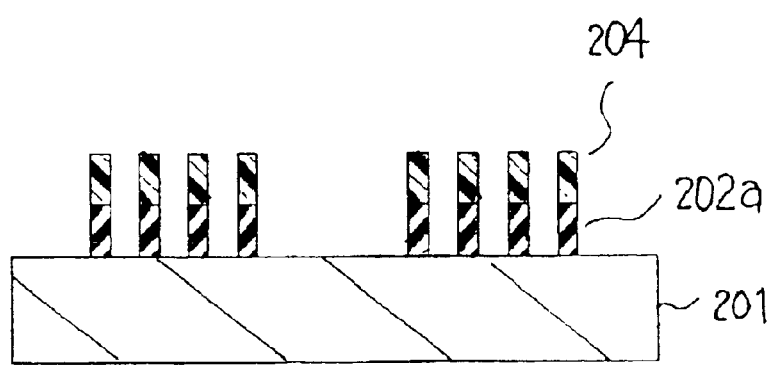
Fig. 5 1 C

FRACTIONATING APPARATUS HAVING COLONIES OF PILLARS ARRANGED IN MIGRATION PASSAGE AT INTERVAL AND PROCESS FOR FABRICATING PILLARS

FIELD OF THE INVENTION

This invention relates to fractionating technologies for a sample containing microstructures and, more particularly, to an apparatus for fractionating a sample into various sorts of microstructures different in size, i.e., cells and fragments of nucleic acid or organic molecules such as amino acids, peptides and proteins, metal ions, colloid and latex beads by using micro-scales and a process for fabricating micro pillars.

DESCRIPTION OF THE RELATED ART

In the analysis on basic building bodies of living creatures, it is popular to fractionate microstructures from a sample and refine the microstructures. Another process popular in the analysis is to sort microstructures in a sample into groups different in length or the amount of electric charge. For example, in the Maxam-Guilbert method, DNA (DeoxyriboNucleic Acid) molecules are marked at one ends with radioisotope $^{32}P$, and are chemically cut into fragments, which are different in length; thereafter, the fragments are fractionated through the electrophoresis, and the base sequence is read from the fragments by using the autoradiography. The fractionation consumes a long time period, and is to be shortened. Thus, to shorten the time period consumed by the fractionation is an important technical goal of the technical field. In other words, the researchers desire a fractionation technology through which microstructures are accurately fractionated within a short time.

An ultracentrifugal separator and a capillary electrophoresis system are widely used as the fractionation apparatus. However, the researchers require a long time for the fractionation through the ultracentrifugal separator and the capillary electrophoresis system. Another drawback inherent in those prior art apparatus/system is that a large amount of sample is required. Moreover, the resolution does not satisfy the researchers.

An apparatus for the fractionation is disclosed in U.S. Pat. No. 5,837,115. In the prior art apparatus disclosed in the U.S. Patent, a lot of obstacles are arranged in array on a surface of a substrate, and fragments in fluid medium are migrated through the array of obstacles. The object to be fractionated is cells, viruses, macromolecules and minute particles according to the U.S. Patent. However, the prior art apparatus has the following problems. First, the paths in the obstacle arrays are liable to be clogged with the fragments. This means that the clogged paths are to be frequently cleaned. This results in a low throughput. Second, it is difficult to form the obstacles at fine pitches. It is impossible to form the obstacles at the fine pitches equal to or less than 200 nanometers through the technologies in those days. For this reason, the prior art apparatus for the fractionation is merely used for microstructures in a certain limited range.

SUMMARY OF THE INVENTION

It is therefore an important object of the present invention to provide an apparatus, with which a small amount of sample is quickly fractionated into fractions different in size at high resolution without clogging. Nucleic acids and proteins are, by way of example, the fractions.

It is also an important object of the present invention to provide a process for fabricating the apparatus through which microbodies are formed in a fractionating passage at high density.

In accordance with one aspect of the present invention, there is provided an apparatus for fractionating a sample into microstructures different in size comprising a fractionating unit including a region for permitting the sample to be migrated and at least one colony of microbodies serving as obstacles against a migration of the microstructures, formed in an area of the region and defining a labyrinth for trapping small-sized microstructures so that a remaining area of the region serves as a path for large-sized microstructures.

In accordance with another aspect of the present invention, there is provided a process for fabricating a fractionating apparatus comprising the steps of a) preparing a substrate structure, b) transferring a pattern of microbodies serving as obstacles against a migration of microstructures from a pattern transferring layer patterned through an electron beam lithography to a surface area of the substrate structure, c) completing the microbodies in the pattern on the surface area, and d) completing a fractionating passage occupying a region of the substrate containing the surface area.

BRIEF DESCRIPTION OF THE DRAWINGS

The features and advantages of the apparatus and process will be more clearly understood from the following description taken in conjunction with the accompanying drawings, in which FIGS. 35A and 35B are plane views showing boundaries of fluid passing through different arrangements of fractionating regions, FIGS. 36A to 36C are schematic views showing buffer solution flowing into a space uniformly filled with artificial gel, FIGS. 43 to 45 are photographs showing a silicon oxide layer grown on the pillars of Sample 1, FIG. 46 is a photograph showing pillars of Sample 2 taken upon completion of an etching, FIGS. 47 to 49 are photographs showing a silicon oxide layer grown on the pillars of Sample 2, FIG. 57 is a graph showing relation between the size of DNA and mean migration speed measured by the inventors.

DETAILED DESCRIPTION ON THE INVENTION

Figure 1:
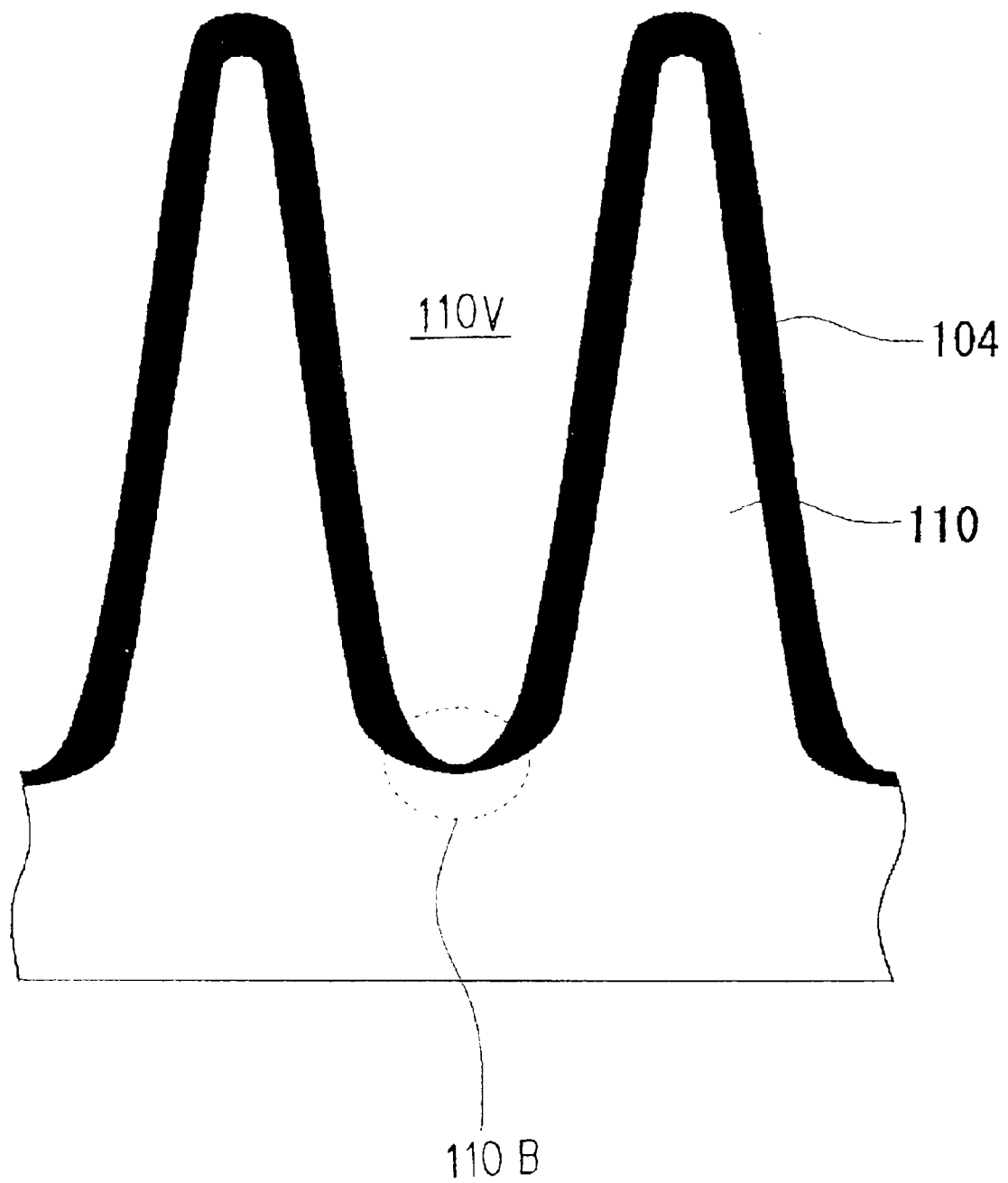
FIG. 1 is a schematic view showing a structure of pillars formed in an apparatus according to the present invention.

An apparatus according to the present invention comprises a body in which at least one passage is formed for sample. The sample flows through the at least one passage. The body is further provided with at least one fractionating region in the passage. Plural pillars are formed in the fractionating region.

An apparatus according to the present invention may comprises a body provided with a groove serving as a passage for sample, a feeder for guiding the sample to the passage, a fractionating region for fractionating the sample into fractions and a sample recovering portion for analyzing or recovering the fractions separately. A colony of pillars is formed in the fractionating region, and may be provided on an inner surface defining a part of the passage.

The plural pillars in the fractionating region are like teeth of a comb, and define intervals. Fractions of the sample are fractionated through the plural pillars. In other words, the pillars are to be many enough to fractionate the sample into the fractions. Even though the fractions are miniature like nucleic acids and proteins, the sample is fractionated into or sorted to the fractions.

The pillars may be covered with hydrophilic layers. The hydrophilic layers may be made of oxide of the material for the pillars. If the substrate and pillars are made of single crystal silicon, silicon oxide is available for the hydrophilic layers. When the sample is fractionated, buffer solution such as water solution is supplied to the apparatus. Since the pillars are covered with the hydrophilic layers, the buffer solution is smoothly introduced into the apparatus. If the pillars are hydrophobic, it is difficult to introduce the buffer solution into the apparatus on the condition that the intervals among the pillars are equal to or less than 200 nanometers. In case where the intervals are further reduced to 100 nanometers or less, the problem is serious. However, the hydrophilic pillars permit the buffer solution smoothly to flow through the extremely narrow intervals. Another advantage of the hydrophilic pillars is to restrict growth of voids.

The pillars may be increased in cross section from the top surfaces thereof toward the bottoms of the valleys like a cone, pyramid or frustum. This feature is desirable, because pillars are uniformly formed at large aspect ratio in good controllability. The irregularity of the aspect ratio is fallen within an extremely narrow range. Even though the oxide layers are grown on the pillars through oxidation, the oxidation is less influential to the aspect ratio. If the pillars have a rectangular parallelepiped configuration, the oxidation proceeds at the bottoms of the valleys faster than at the upper end portions, and the oxide become thicker at the bottoms of the valleys rather than the oxide on the upper end portions. The oxide swells into eminences on the bottoms of the valleys. This results in reduction in aspect ratio. However, the oxide tends to be uniformly grown on the pillars, which are increased in cross section toward the bottoms. Thus, the pillars, which are increased in cross section toward the bottoms, are preferable from the viewpoint of a large aspect ratio.

The pillars may be merged with one another at the bottom portions of the valleys. This feature is also desirable from the viewpoint of a large aspect ratio. In case where the pillars are contiguous to one another at the bottoms of the valleys, the excess oxidation is restricted at the bottoms, and the pillars have a large aspect ratio. If the pillars are widely spaced from one another, the valleys among the pillars have flat bottoms among the pillars. The oxidation proceeds faster on the flat bottoms, and the oxide swells into eminences. On the other hand, pillars contiguous to each other define sharp valleys there-among, and the sharp valleys have curved surfaces. While the substrate is being exposed to the oxidizing atmosphere, the oxidation proceeds non-uniformly over the entire surfaces of the pillars, and is restricted at the sharp bottoms of the valleys, because the compressive stress due to the volume expansion in the narrow bottoms is exerted on the oxide. The restriction on the growth results in a relatively thin oxide layer or an oxide layer as thin as the oxide layer on the upper end portions of the pillars. In other words, the oxide does not swell into eminences at the sharp bottoms, and the oxide layers permit the pillars to keep the aspect ration large. FIG. 1 shows conical pillars 110. The conical pillars 110 are contiguous to one another at the bottom 110B of the valley 110V. While the conical pillars 110 are being exposed to oxidation atmosphere, the surface portions of the pillars 110 are oxidized, and an oxide layer 104 is grown on the surfaces of the conical pillars 110. However, the oxide is less grown at the bottom 110B. The oxide layer 104 is thinner at the bottom 110B rather than on the side surfaces of the conical pillars 110. The reason why the oxide is less grown at the bottom 110B is that the volume expansion at the bottom 110B makes the compressive stress larger than the compressive stress on the side surfaces. The oxide does not swell into an eminence, and the thin oxide keeps the valley 110V deep. This results in a large aspect ratio.

The apparatus exhibits large resolution through the large-aspect ratio pillars gathered at high density. From this viewpoint, it is preferable that the pillars, which are increased in cross section toward the bottoms of the valleys, are contiguous to one another at the bottoms of the valleys. The pillars are to be uniform in measure. From this viewpoint, the pillars are to be formed without a large tolerance, because the manufacturer can easily optimize the pillars to sample to be fractionated. Although a patterning technology available for the pillars uniformly patterned at the large aspect ratio has not been known to persons skilled in the art, the present inventors find that an electron beam lithography is available for the pillars. A sort of electron beam resist is used in the electron beam lithography, and is named as calixarene, the structural unit of which is expressed as follows.

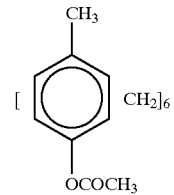

The electron beam resist is used for miniature patterns of the order of nanometers.

The apparatus may have a fractionating region where plural colonies of pillars or pillar patches are formed. The plural colonies of pillars are provided ed in a passage or passages through which the sample is migrated.

The apparatus described hereinbefore behaves on the basis of a principle different from the principle in the prior art apparatus disclosed in U.S. Pat. No. 5,837,115. The prior art apparatus disclosed in the U.S. Patent is on the basis of the principle that obstacles impede the migration of large-sized microstructures such as large-sized molecules more seriously than those impede the migration of small-sized microstructures or small-sized molecules. Accordingly, the small-sized microstructures are firstly output from the prior art apparatus, and the large-sized microstructures are output from the prior art apparatus after the small-sized microstructures.

On the other hand, the apparatus according to the present invention behaves on the basis of the principle that small-sized microstructures such as small-sized molecules are much liable to be trapped in the colony of pillars rather than large-sized microstructures such as large-sized molecules are. The small-sized microstructures trapped in the colony of pillars are to travel over a length greater than a traveling length of the large-sized microstructures. This results in that the small-sized microstructures are output from the apparatus later than the large-sized microstructures are. Thus, the large-sized microstructures are migrated through the fractionating region smoother than the small-sized microstructures are. This means that the fractionating region is less clogged with the microstructures. The throughput of the apparatus according to the present invention is larger than that of the prior art apparatus.

Nucleic acids and proteins are examples of the microstructures, and have respective values of inertial radius of curvature widely dispersed. If the nucleic acids and proteins are sorted by using the prior art apparatus, the migration paths are much liable to be clogged with the largest ones. Even if the prior art apparatus is cleaned, the largest ones are less removed from the migration paths. The apparatus according to the present invention is effective against the clogging with the large-sized ones, because the large-sized ones are smoothly migrated through the fractionating region.

According to the present invention, the width of the path is greater than the mean gap between the pillars, because large-sized microstructures are smoothly migrated through the path. The small-sized microstructures are migrated through the colony of pillars, and the traveling length is prolonged depending upon the size of the microstructures.

The values of gap between the pillars may be different among the colonies of pillars. This means that the apparatus according to the present invention has two sorts of parameters, i.e., the gap between the pillars and the width of the path for each colony of pillars. Even if a sample contains a wide variety of microstructures different in size, the sample is fractionated to groups of microstructures at high resolution without clogging and reduction in throughput by virtue of the two sorts of parameters. In case where small-sized molecules are to be sorted at a high resolution, the gap among the pillars is adjusted to several to tens nanometers, and the path is widened. Large-sized molecules are smoothly migrated through the path so that the path is less liable to be clogged with the large-sized molecules.

The path may be directed in a certain direction different from the direction of fluid passage through which the sample is migrated. In this instance, the molecules in the samples are frequently brought into contact with the colony of pillars, and small-sized microstructures or small-sized molecules are trapped in the colony of pillars at a high probability. This results in improvement in the resolution. It is preferable that the angle between the direction of the migration and the direction of the path is fallen within 10 degrees to 80 degrees. It is more preferable that the angle is fallen within 30 degrees to 60 degrees. If the angle is too small, the microstructures do not frequently contact with the colony of pillars. On the other hand, if the angle is too large, the pillars of the patch are obstacles against the flow so that the throughput is decreased.

The mean gap between the pillars may be equal to or less than 100 nanometers. The "gap" or "interval" is equivalent to the distance between the center line of a pillar and the center line of an adjacent pillar. Such a narrow gap is desirable, because small-sized microstructures, which the prior art apparatus has not been cable to sort, are sorted by using the colony of pillars. When the apparatus is used for fractionating a sample to nucleic acids and proteins, a colony of pillars, the pillars of which are arranged at intervals of hundreds nanometers or less, is indispensable. If the gap is too large, the colony of pillars can not function as a comb. With the apparatus equipped with a colony of pillars, the mean gap of which is 70 nanometers or less, a sample is more precisely fractionated into fractions or microstructures.

When the width of path and the gap among the pillars are determined, the median M of the fractions in a sample and standard deviation σ may take into consideration. The apparatus thus optimized is improved in the efficiency of the fractionation. When the gap among the pillars is adjusted to M, the width of path may be regulated to (M+2σ). The gap in another colony of pillars and the width of path may be adjusted to 2M and (2M+2σ), respectively.

In an apparatus having plural colonies of pillars in the passage, the pillar density may be decreased from the upstream toward the downstream. While the sample is migrated through the passage, large-sized microstructures or molecules are smoothly migrated through the passage, and small-sized microstructures or molecules stays in the colony of pillars for a long time. This results in that the small-sized microstructures are surely delayed so that the resolution is enhanced.

On the other hand, another apparatus may have plural colonies of pillars increased in density from the upstream toward the downstream. In this instance, clogging is strongly restricted so that the throughput is enhanced.

In yet another apparatus according to the present invention, the pillars may have respective tops spaced from the inner wall defining the passage. The gap between the tops and the inner wall offers a path for large-sized microstructures so that the passage is less clogged with the large-sized microstructures. Moreover, the gap between the tops and the inner wall further offers an entrance into the colony or colonies of pillars so that small-sized microstructures are much liable to be trapped in the colony or colonies of pillars. Thus, the pillars spaced from the inner wall are conducive to improvement in fractionation.

Still another apparatus according to the present invention may have pillars that form a row like a dam. The row of pillars gathers sample dispersed in medium in a region in the vicinity thereof. It is preferable to gather the sample before the fractionation. When the sample is gathered, the sample tends to form a narrow band, and the narrow band makes the fractionating efficiency enhanced. The dam-like pillars may be located at a certain portion contiguous to the fractionating region. In this instance, the sample is shaped into a narrow band prior to the fractionation so that the fractionating efficiency is enhanced. In other words, the apparatus achieves a high-precision fractionation.

The inner surface defining a passage may be hydrophilic. The hydrophilic inner wall makes the microstructures in a sample smoothly migrated through the passage, and is conducive to the enhancement of the fractionation.

The pillars of each colony of pillars may be same in size and arranged at regular intervals. This results in enhancement of the fractionating efficiency. The more the pillars in a patch, the higher the resolution.

The colonies of pillars may have respective groups of pillars different in size. In this instance, the pillars of each patch are different in intervals and size from the pillars of another patch. Even if a sample contains fractions widely different in size, the colonies of pillars fractionate the sample into the fractions at a high resolution without clogging and reduction in throughput.

An apparatus according to the present invention may further include a sample accelerator. The sample accelerator exerts external force on the sample so as to accelerate the migration through the passage. The sample accelerator varies the time consumed in the migration so that the resolution is changed depending upon the sample to be fractionated. The force to be exerted on the sample may be pressure or electric force generated in an electric field. The pressure and electric force are preferable, because the generator is compact. A sample may be migrated by using the capillary phenomenon. The migration through the capillary phenomenon permits the manufacturer to scale down the apparatus.

The microstructures to be sorted are nucleic acid molecules, fragments of the nucleic acid molecules, organic molecules such as amino acid, peptide and protein, metal ion, colloid and latex beads, by way of example. The apparatus according to the present invention is preferable for a sample containing nucleic acid molecules and fragments thereof or protein molecules and fragments thereof. These sorts of sample are to be fractionated into small-sized fractions at high resolution, and the intervals of the order of hundreds nanometers or less are required for the colony or colonies of pillars in the apparatus. Moreover, the sample contains large-sized microstructures, and the passage is liable to be clogged with the large-sized microstructures. The apparatus according to the present invention fulfills these requirements. Thus, the apparatus according to the present invention is preferable for the sample containing nucleic acid molecules and/or protein molecules.

The apparatus may have plural fractionating regions arranged in a passage spaced apart from one another by means of slit or slits. Each of the plural fractionating regions occupies entire cross section of the passage. The slit may be single or plural. The fractionating regions may be altered with buffer regions in which the pillars are formed sparsely rather than the fractionating regions. The band is shaped linearly. This is equivalent to a wide detecting region, and the sensitivity is enhanced.

An apparatus according to the present invention may include a nanostructure in which plural pillars are formed on a surface of a substrate. The plural pillars have respective base portions wider in cross section than respective top portions, and the base portions are merged with one another at the bottoms of the valleys defined among the pillars. As described hereinbefore, the oxidation at the bottoms of the valleys is restricted so that the pillars have individual values of the aspect ratio fallen within a narrow range. Such a uniformly produced pillars are preferable for the fractionating apparatus or a component or components of various sorts of element.

A process for fabricating the apparatus according to the present invention comprises the steps of preparing a substrate having a major surface and a die having a transfer surface with a pattern of projections, spreading resist material over the major surface so as to form a resist layer, pressing the major surface of the die to the resist layer for forming recesses in the resist layer, removing parts of the resist layer defining the recesses for forming openings in the resist layer and etching the substrate exposed to the openings for forming pillars.

The projections and recesses are transferred from the major surface of the die to the resist layer at fine pitches. A die is available for forming the pillars at intervals equal to or less than 200 nanometers. Another die is available for forming the pillars at intervals equal to or less than 100 nanometers. The die enhances the productivity. If an electron beam lithography is employed in the pattern formation, a long time period is consumed by the patterning step through the electron beam lithography, and the manufacturer suffers from a low productivity. The pattern transfer step through the electron beam lithography is not required for the process according to the present invention. The pattern transfer from the die to the resist layer is completed within a time period much shorter than the time period for the patterning step through the electron beam lithography. Thus, the fractionating apparatus are fabricated through the process according to the present invention at high productivity.

Any sensitivity to light and electron beam is not required for the resist used in the process according to the present invention. Nevertheless, the resist layer is practically deformed by the die, solidified through baking and has a certain degree of resistivity against a sort of etchant such as dry etchant. An example of the resist is resin in polymethyl methacrylate series. The resist layer may be partially removed through ashing.

The apparatus according to the present invention may be fabricated on a substrate having a resin layer, which offers a major surface. A die formed with a pattern of recesses is pressed to the resin layer so as to form pillars in the resin layers. Any electron beam lithography is not required for the pattern transfer so that the productivity is drastically enhanced.

The indispensable feature of the apparatus according to the present invention is the fractionating region. Even if a sample feeding region and the sample accelerator are not incorporated in the apparatus, a sample is fractionated into fractions. The fractionating region may be offered to users in the form of throw-away cartridge. The user assembles the through-away cartridge into an apparatus according to the present invention before the fractionation of a sample.

Another process for fabricating the apparatus according to the present invention comprises the steps of preparing a substrate having a silicon oxide layer, forming a silicon layer on the silicon oxide layer, selectively etching the silicon layer, thermally oxidizing the silicon layer for merging the thermally oxidized layer with the silicon oxide layer. The apparatus fabricated through the process is formed with a fluid passage for a sample electrically isolated from the substrate. The substrate is preferable for the apparatus equipped with the sample accelerator for accelerating the migration of sample in an electric field. A researcher can apply a high voltage. Thus, the substrate offers a highly flexible apparatus to users.

DESCRIPTION OF THE PREFERRED EMBODIMENTS

An apparatus according to the present invention is fabricated on a substrate. The substrate is, by way of example, made of single crystal silicon, glass such as, for example, quartz or synthetic resin such as silicone resin. A groove or grooves are formed in a major surface portion of the substrate. A passage or passages and a fractionating region or regions are formed in the groove or grooves. The major surface of the substrate is overlaid with a cover plate so that the passage/passages and fractionating region/regions are confined in the space defined by the substrate and the cover plate.

Pillars are formed on the substrate through an etching, by way of example. There is not any limit to the patterning technique. The pillars may have a configuration such as a cylinder, pyramid, prism or striped pattern of projections. A circular cylinder and a cylindroid are examples of the cylinder, and the pyramid contains a cone, elliptical cone, a trigonal pyramid and a quadrangular pyramid. A trigonal prism and a quadrangular prism are examples of the prism. The cylinder may measure 10–200 nanometers by 10–1000 nanometers.

The pillars are gathered so as to form a colony of pillars. The gap between the pillars adjacent to one another is to be adjusted to a certain value preferable to the fractionation. When the manufacturer designs the colony of pillars, the designer takes microstructures contained in a sample into account. The apparatus may be used for the fractionation and enrichment on the following samples.

The sample is presumed to contain cells and other sorts of microstructures. When the cells are separated from the other sorts of microstructures, the gap ranges from 1 micron to 10 microns.

The sample is homogenate, i.e. fractions of broken cells. When the fragments of cell membranes and organelles such as mitochondria and endoplasmic reticulums from soluble fraction, i.e., cytosol, the gap ranges from 100 nanometers to 1 micron.

The sample is the soluble fraction. When high molecule weight components such as DNA, RNA, proteins and sugar chains from low molecular weight components such as, for example, steroid and grape sugar, the gap ranges from 1 nanometer to 100 nanometers.

A single colony of pillars or more than one colony of pillars is incorporated in the apparatus. The pillars of the colony may be same in size and arranged at regular intervals. In another apparatus, the pillars of the colony are different in size, and are arranged at irregular intervals. The colonies of pillars may be different in size and arranged at irregular intervals.

The gap between adjacent colonies of pillars serves as a path through which the sample is migrated. It is preferable that the gap between the adjacent colonies of pillars is greater than the gap between the adjacent pillars, i.e., the intervals among the pillars, because the large-sized microstructures such as giant molecules are smoothly migrated through the path. This results in enhancement of the efficiency of the fractionation.

First Embodiment

Figure 2:
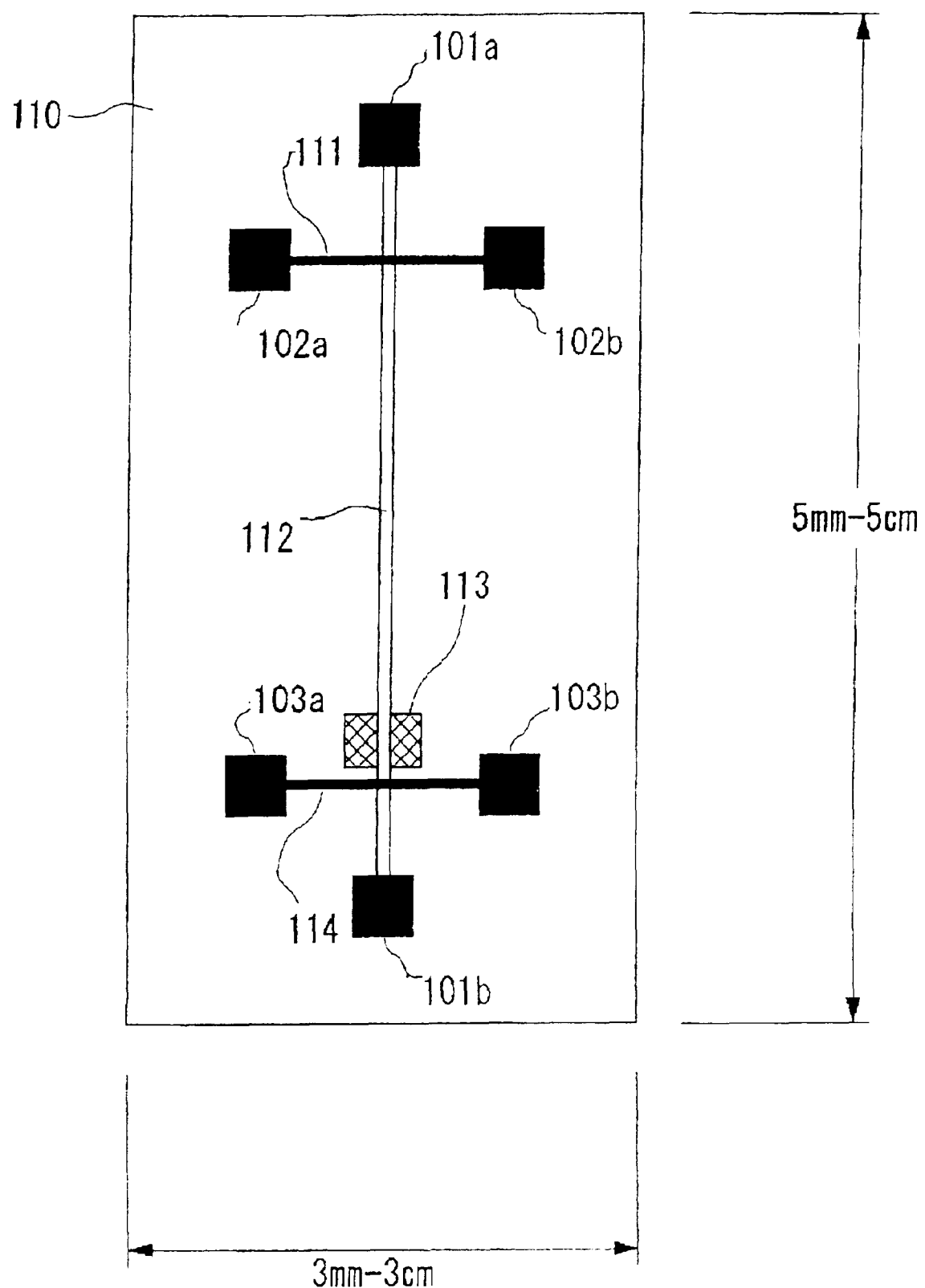
FIG. 2 is a schematic plane view showing a layout in an apparatus according to the present invention.
Figure 3:
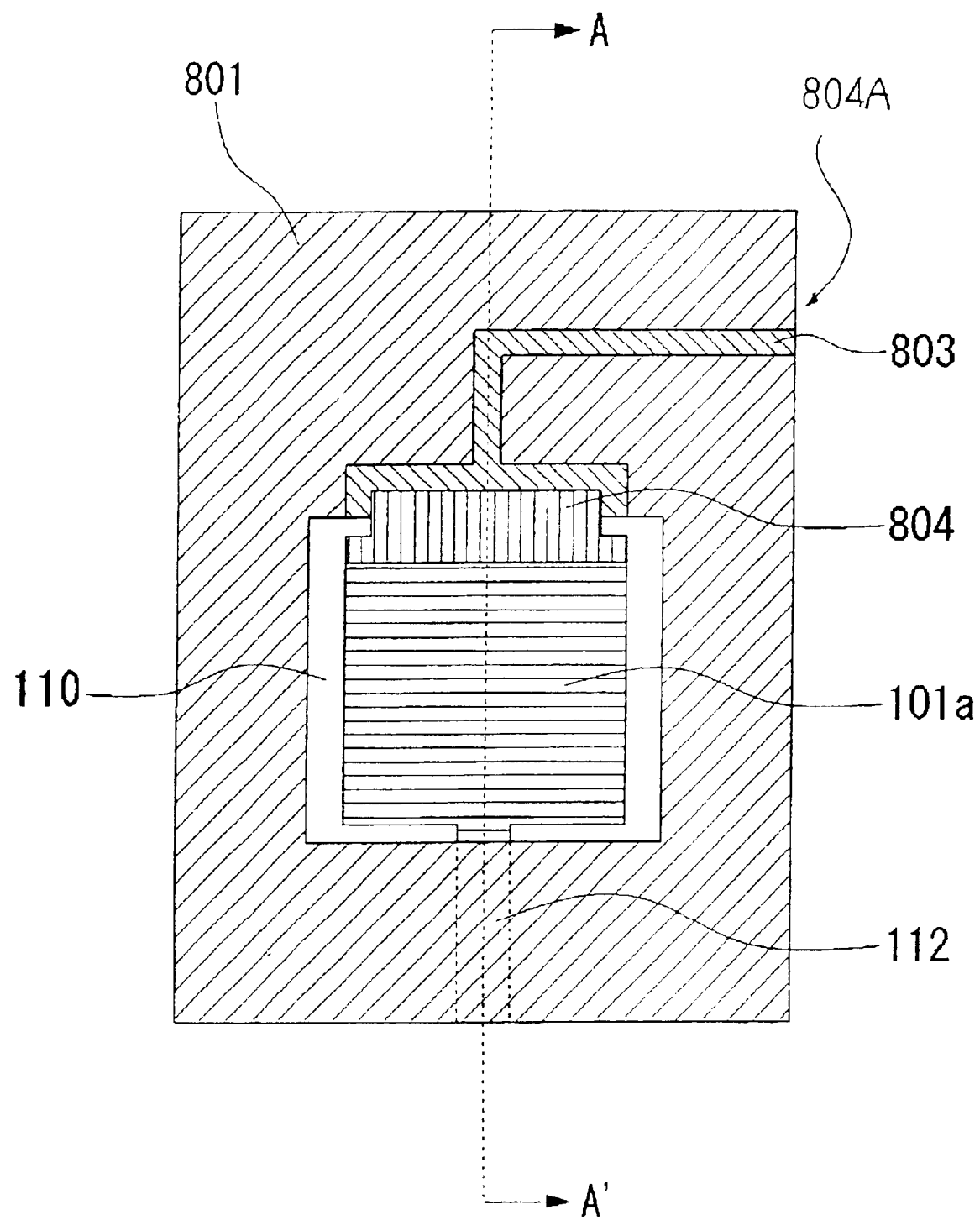
FIG. 3 is a plane view showing a liquid sump incorporated in the apparatus.
Figure 4:
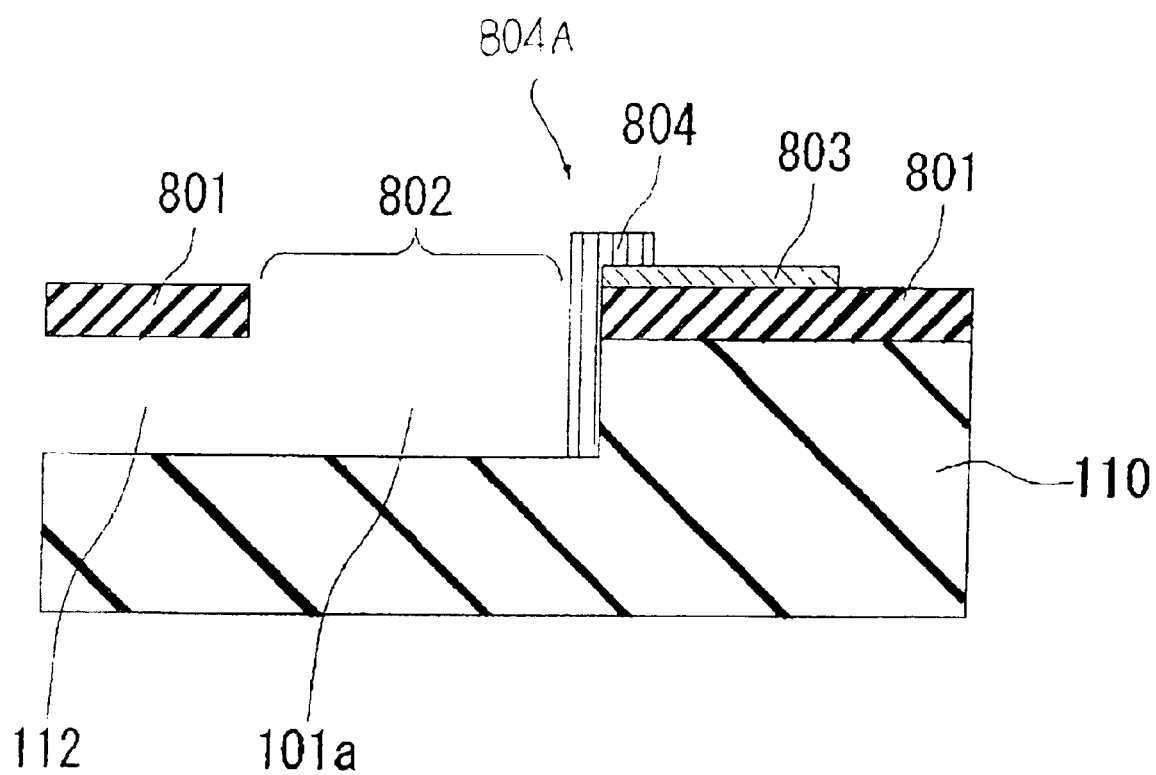
FIG. 4 is a cross sectional view taken along line A–A' of FIG. 3 and showing the structure of the liquid sump.

Referring first to FIG. 2 of the drawings, an apparatus embodying the present invention comprises a substrate 110 and a cover plate 801 (see FIGS. 3 and 4). Although a controller and a sample accelerator are further incorporated in the apparatus, they are not shown in FIG. 2.

The substrate 110 measures 5 millimeters to 5 centimeters by 3 millimeters to 3 centimeters. A fractionating passage 112 is formed in the substrate 110, and extends in the longitudinal direction. Though not shown in FIG. 1, pillars are formed in the fractionating passage 112. The pillars are designed to trap microstructures, i.e., molecules of a certain size. While a sample is migrated through the fractionating passage 112, the sample is fractionated into fractions different in size. Thus, the fractionating passage 112 partially serves as a fractionating region and partially as a path through which a sample is migrated.

Liquid sumps 101a and 101b are formed in the substrate 110 at both ends of the fractionating passage 112, and the fractionating passage 112 is connected to these liquid sumps 101a/101b. Electrodes 104 (see FIGS. 3 and 4) are provided in association with the liquid sumps 101a and 101b, and are connected to an electric power source (not shown). Bias voltage is applied between the electrodes 104 for creating an electric field between the liquid sumps 101a and 101b. When the electric field is created between the liquid sumps 101a and 101b, electric force is exerted on the sample, and the sample is migrated along the fractionating passage 112.

A detecting device 113 is provided in the fractionating passage 112. Fractions of the sample are optically or physico-chemically discriminated with the detecting device 113. An optical detecting device 113 is assumed to be employed in the apparatus. The detecting device 113 radiates a laser light beam to the fractions of the sample. A certain sort of fluorescent material has been bonded to a certain sort of molecules in the sample. When the certain sort of molecules reaches the detecting device 113, the molecules generate the fluorescence, and the fluorescence is incident on the detecting device 113. Then, the detecting device 113 outputs a detecting signal representative of the arrival of the molecules. Thus, the detecting device 113 discriminates certain microstructures with a tag, and reports the arrival to the controller (not shown) connected thereto.

A feed passage 111 and a recovery passage 114 cross the fractionating passage 112. The feed passage 111 extends in the lateral direction, and is connected to one end portion of the fractionating passage 112. The feed passage 111 is associated with liquid sumps 102a/102b. The recovery passage 114 also extends in the lateral direction, and is connected to the other end portion of the fractionating passage 112. The recovery passage 114 is also associated with liquid sumps 103a/103b. The recovery passage 114 is located between the detecting device 113 and the liquid sump 101b.

The liquid sumps 102a/102b are formed in the substrate 110 at both ends of the feed passage 111, and are connected to both end portions of the feed passage 111. On the other hand, the liquid sumps 103a/103b are formed in the substrate 110 at both ends of the recovery passage 114, and are connected to both end portions of the recovery passage 114. Electrodes are provided in association with the liquid sumps 102a/102b and 103a/103b, and are connectable to an electric power source (not shown). When the electrodes in the liquid sumps 102a/102b are biased, electric field is created between the liquid sumps 102a and 102b, and a sample is migrated through the feed passage 111. Similarly, when the electrodes in the liquid sumps 103a/103b are biased, electric field is created between the liquid sumps 103a and 103b, and fractions are migrated through the recovery passage 114.

The liquid sumps 101a/101b, 102a/102b and 103a/103b are similar in structure to one another so that only the liquid sump 101a is described with reference to FIGS. 3 and 4. Although FIGS. 3 does not show any cross-section, hatching lines are drawn in order to clearly discriminate components from one another.

The substrate 110 is overlaid with the cover plate 801, and an opening 802 is formed in the cover plate 801. The opening 802 is used for supplying buffer solution to the liquid sump 101a. A conductive strip 803 is patterned on the cover plate 801, and the electrode 804 is provided on a side wall defining a part of the liquid sump 101a. The conductive strip 803 reaches the liquid sump 101a, and inserted between the cover plate 801 and the electrode 804. The electrode 804 is pressed to the conductive strip 803, and is merged to the conductive strip 803. Thus, the bias voltage is supplied through the conductive strip 803 to the electrode 804. The electrodes 104 in the liquid sumps 101a/101b, 102a/102b and 103a/103b and the electric power source as a whole constitute the sample accelerator 804A.

Using the apparatus shown in FIGS. 2 to 4, a sample, which contains molecules of the certain size, is fractionated into fractions different in size as follows. First, the sample is supplied into one of the liquid sumps 102a or 102b. When the sample is supplied to the liquid sump 102a, the electric field is created in such a manner that the sample flows toward the other liquid sump 102b through the feed passage 111. If the sample is supplied to the other liquid sump 102b, the sample flows in the opposite direction through the feed passage 111 in the electric field created between the liquid sumps 102a and 102b. The sample flows from the liquid sump 102a/102b into the feed passage 111, and fills the feed passage 111. Since the feed passage 111 crosses the fractionating passage 112, part of the sample occupies the crossing point between the fractionating passage 112 and the feed passage 111, and forms a band which is as narrow as the width of the feed passage 111.

Subsequently, the electric field is removed from between the liquid sumps 102a and 102b, and bias voltage is applied between the liquid sump 101a and the liquid sump 101b in such a manner that the sample flows toward the liquid sump 101b. The electric force is differently exerted on the microstructures of the sample depending upon the molecular size and the amount of electric charge. The sample is migrated through the fractionating passage 112, and the molecules of the certain size are trapped in the pillars. However, the other microstructures larger in size than the molecules are migrated through the fractionating passage 112 without being trapped in the pillars. While the sample is migrated through the fractionating passage 112, the sample is fractionated into bands migrated at different speeds. When the band of microstructures, which are marked with a tag, reaches the detecting device 113, the detecting device 113 supplies the detecting signal to the controller (not shown). Then, the bias voltage is removed from between the electrodes 104 in the liquid sumps 101a and 101b. When the band of microstructures reaches the crossing point between the fractionating passage 112 and the recovery passage 114, bias voltage is applied between the electrodes in the liquid sumps 103a and 103b. The band of microstructures enters the recovery passage 114, and is migrated through the recovery passage 114 to one of the liquid sumps 103a/103b. Thus, the target microstructures or target molecules are separated from the other microstructures, and are enriched in the liquid sumps 103a or 103b.

Figure 5:
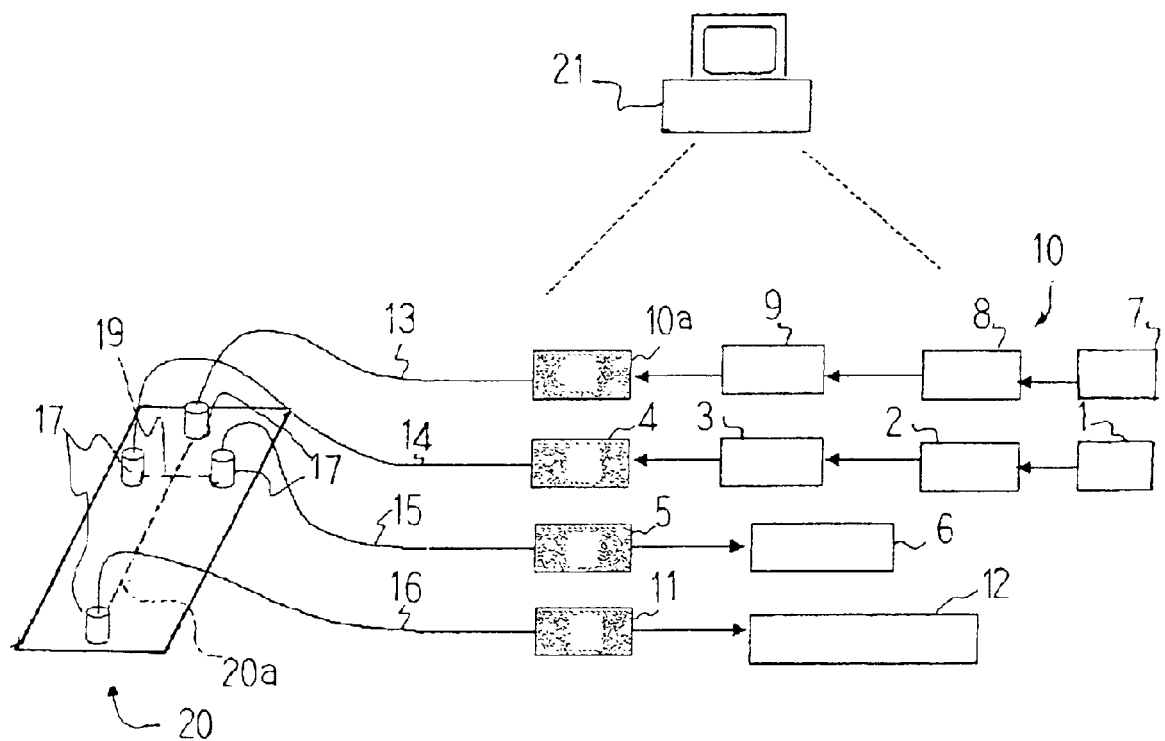
FIG. 5 is a perspective view showing the arrangement of another apparatus according to the present invention.

As will be understood from the foregoing description, the sample is fractionated through the fractionating passage 112 where at least one pillar passage is formed, and the target microstructures are enriched in the liquid sump 103a/103b.
Second Embodiment FIG. 5 shows another apparatus embodying the present invention. The apparatus implementing the second embodiment comprises a sample accelerator 10, a fractionating unit 20 and a controller 21. The fractionating unit 20 includes a substrate 20A and a cover plate 20B (see FIG. 6) as similar to that of the first embodiment. A fractionating passage 20a and a feed passage 19 are formed in the substrate 20A, and the fractionating passage 20a crosses the feed passage 19 at right angles. Pillars are formed in the fractionating passage 20a, and are designed to trap microstructures of a predetermined size thereinto. The pillars occupy an area of the fractionating passage 20a, and the remaining area serves as a path for large-sized microstructures. Openings 20c are formed in the cover plate, and are aligned with both end portions of the fractionating/feed passages 20a/19. In this instance, the openings have a diameter of the order of 2 millimeters.

The sample accelerator 10 comprises a series combination of a reservoir 1, a pump 2, a rate controller 3, an electromagnetic valve 4, a flexible tube 14 and a joint unit 17 and another series combination of a joint unit 17, a flexible tube 15, an electromagnetic valve 5 and a drain vessel 6. A sample is stored in the reservoir 1, and is pressurized by the pump 2. The rate controller 3 delivers the sample through the electromagnetic valve 4 to the flexible tube 14 at constant rate, and the flexible tube 14 is connected through the joint unit 17 to one end portion of the feed passage 19. On the other hand, the other end portion of the feed passage 19 is connected through the joint unit 17 to the flexible tube 15, and the flexible tube 15 is connected through the electromagnetic valve 5 to the drain vessel 6. The residue of the sample is recovered from the other end portion of the feed passage 19 to the drain vessel 6. Thus, the sample is supplied to the feed passage 19 through the series combination 1/2/3/4/14/17, and the residue is recovered through the other series combination 15/5/6.

The sample accelerator 10 further comprises yet another series combination of a reservoir 7, a pump 8, a rate controller 9, an electromagnetic valve 10a, a flexible tube 13 and a joint unit 17 and still another series combination of a joint unit 17, a flexible tube 16, an electromagnetic valve 11 and an auto-sampler 12. Buffer solution is stored in the reservoir 7, and is pressurized by the pump 8. The rate controller 9 delivers the buffer solution through the electromagnetic valve 10a to the flexible tube 13 at constant rate, and the flexible tube 14 is connected through the joint unit 17 to one end portion of the fractionating passage 20a. Part of the sample is migrated through the fractionating passage 20a together with the buffer solution. While the sample is migrated through the fractionating passage 20a, the sample is fractionated into fractions or microstructures different in size. The fractions intermittently reach the other end of the fractionating passage 20a depending upon the size of the microstructures. On the other hand, the other end portion of the fractionating passage 20a is connected through the joint unit 17 to the flexible tube 16, and the flexible tube 16 is connected through the electromagnetic valve 11 to the auto-sampler 12. The fractions of the sample are recovered from the other end portion of the fractionating passage 20a to the auto-sampler 12. Thus, the sample is supplied to the feed passage 19 through the series combination 1/2/3/4/14/17, and the residue is recovered through the other series combination 15/5/6.

Figure 6:
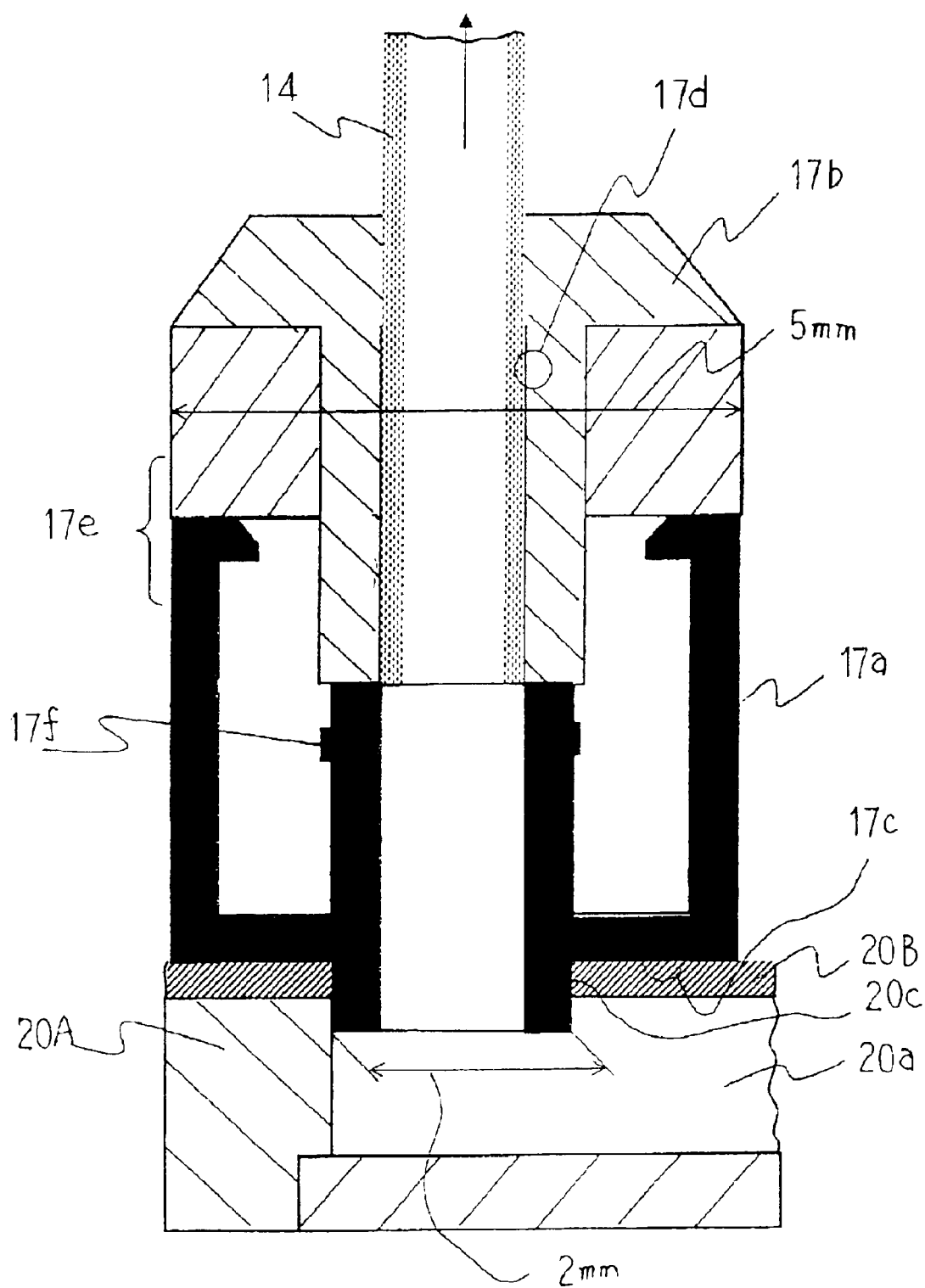
FIG. 6 is a schematic cross sectional view showing the structure of a joint unit incorporated in the apparatus.

The joint unit 17 is broken down into a female part 17a and a male part 17b (see FIG. 6). In order to clearly discriminate the female part from other components, the female part 17a is drawn in black. The female part 17a is inserted into the opening 20c, and is fixed to the cover plate 20B. The contact 17c between the female part 17a and the cover plate 20B is so tight that liquid can not be leaked therethrough. The flexible tube 14 is inserted into the male part 17b, and is secured to the male part 17b. The male part 17b has a diameter of the order of 5 millimeters. The contact 17d between the flexible tube 14 and the male part 17b is so tight that liquid can not be leaked there-through. The male part 17b is connectable to and disconnectable from the female part 17a. When the male part 17b is connected to the female part 18a, the contact 17e is so tight that liquid can not be leaked therethrough. Reference numeral 17f designates a packing piece. Thus, the flexible tube 14 is connected to the passage 20a/19 without any leakage by mean of the joint unit 17.

Turning back to FIG. 5, the controller 21 is connected to the electromagnetic valves 4/5/10a/11, pumps 2/8 and rate controllers 3/9. The controller 21 sequentially energizes those components 4/5/10a/11/2/8/3/9 at proper timings so as to control the fractionation as follows.

First, sample and buffer solution are stored in the reservoirs 1 and 7, respectively. The controller 21 removes the electric power from the electromagnetic valves 10a and 11. Then, the electromagnetic valves 10a/11 are closed, and the rate controller 9 and the auto-sampler 12 are isolated from the flexible tubes 13/16.

Subsequently, the controller 21 energizes the electromagnetic valves 4/5 so that the rate controller 3 and the flexible tube 15 are connected to the flexible tube 14 and the drain vessel 6. The sample has been already supplied to the reservoir 1. The controller 21 activates the pump 2 and rate controller 3. The sample is supplied through the electromagnetic valve 4 and flexible tube 14 to one end portion of the feed passage 19. The sample is filled in the feed passage 19, and excess sample is recovered to the drain vessel 6. However, the sample hardly flows into the fractionating passage 20a. This is because of the fact that the electromagnetic valves 10a/11 have been closed.

When the feed passage 19 is filled with the sample, the controller 21 removes the electric power from the electromagnetic valves 4/5, and energizes the electromagnetic valves 10a/11. The rate controller 9 and the flexible tube 16 are connected to the flexible tube 13 and the auto-sampler 12, respectively. The controller 21 energizes the pump 8 and rate controller 9. The buffer solution is supplied through the flexible tube 13 to one end portion of the fractionating passage 20a at constant rate, and exerts pressure on the part of the sample at the crossing point between the feed passage 19 and the fractionating passage 20a.

The sample is fractionated into fractions, i.e., microstructures different in size, and the fractions intermittently reach the other end of the fractionating passage 20a. Although target microstructures are trapped in the pillars, large-sized microstructures are smoothly migrated through the fractionating passage. The fractions flow into the flexible tube 16 together with the buffer solution, and are propagated through the electromagnetic valve 11 to the auto-sampler 12. Thus, the fractions are intermittently recovered by means of the auto-sampler 12.

As will be understood, the apparatus implementing the second embodiment is available for the fractionation of sample without clogging. The sample accelerator 10 exerts the pressure on the part of the sample so as to migrate it through the fractionating passage 20a. The sample accelerator 10 is simpler and smaller in size than the sample accelerator, which creates the electric fields in the apparatus implementing the first embodiment, is. The sample accelerator 10 is conducive to reduction in production cost of the apparatus according to the present invention.

Third Embodiment

Figure 7:
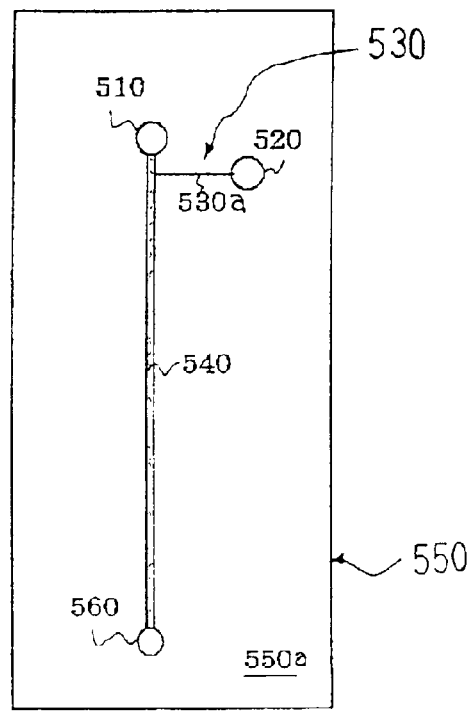
FIG. 7 is a schematic plane view showing the layout on a fractionating unit forming a part of yet another apparatus according to the present invention.

FIG. 7 shows a major surface of a substrate forming a part of yet another apparatus embodying the present invention. In the apparatus implementing the third embodiment, sample is migrated with an assistance of the capillary phenomenon. The apparatus implementing the third embodiment comprises a sample accelerator 530 and a fractionating unit 550. The sample accelerator 530 accelerates sample through the capillary phenomenon.

The fractionating unit 550 includes a substrate 550a and a cover plate (not shown), and the sample accelerator 530 is built in the substrate 550a as will be described hereinafter in detail. A fractionating passage 540 and a quantitative passage 530a are formed in the substrate 550a, and are open on the major surface of the substrate 550a. Pillars are formed in the fractionating passage 540, and are hereinbelow referred to as "fractionating pillars". The fractionating passage 540 extends in the longitudinal direction of the substrate 550a, and the quantitative passage 530a extends in the lateral direction of the substrate 550a. The quantitative passage 530a is connected to one end portion of the fractionating passage 540 at right angles. The major surface of the substrate 550a is overlaid with the cover plate (not shown), and feed ports and an air hole are formed in the cover plate. Circles 510/520/560 stand for the feed ports and the air hole. The feed port 510 is aligned with one end portion of the fractionating passage 540, and the air hole 560 is aligned with the other end portion of the fractionating passage 540. The feed port 520 is aligned with one end portion of the quantitative port 520, and the quantitative passage 530a is connected to the fractionating passage 540 in the vicinity of the feed port 510. The cover plate is tightly held in contact with the major surface of the substrate 550a so that sample and buffer solution are never leaked from the fractionating passage 540 and the quantitative passage 530a through between the substrate 550a and the cover plate.

Figure 8:
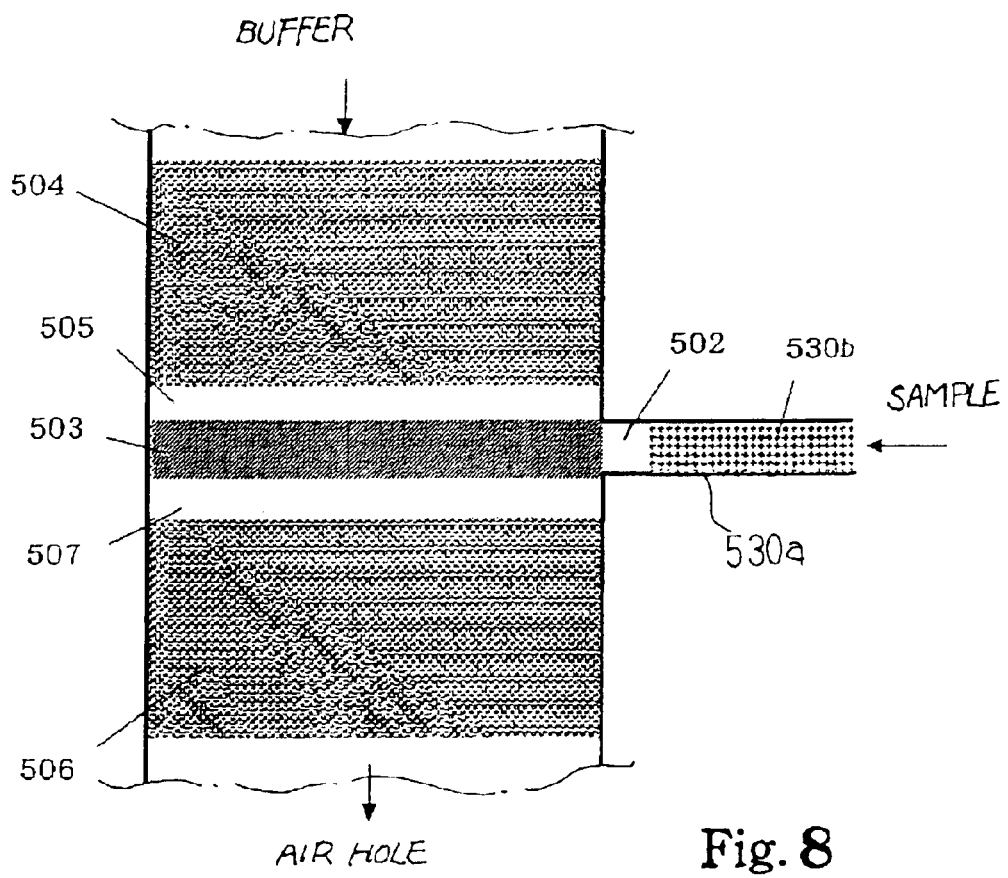
FIG. 8 is a schematic plane view showing a sample accelerator built in the fractionating unit.

FIG. 8 shows the fractionating pillars 506 and the sample accelerator 530 built in the substrate 550a. The sample accelerator 530 includes quantitative pillars 530b, a holding space 502, sample holding pillars 503, introducing pillars 504 and holding spaces 505/507. The fractionating pillars are as dense as the introducing pillars 504. The holding pillars 503b are denser than the fractionating pillars 506 and introducing pillars 504 are. However, the quantitative pillars are sparse rather than the fractionating pillars 506 and introducing pillars 504 are. For this reason, the sample is never fractionated into fractions in the quantitative pillars 530b. The holding pillars 503 occupy an area contiguous to the quantitative passage 530a, and is spaced from the quantitative pillars 530b by the holding space 502. The introducing pillars 504 occupy an area closer to the feed port 510 than the holding pillars 503, and is spaced from the holding pillars 503 by the holding space 505. On the other hand, the fractionating pillars 506 occupy an area on downstream side of the holding pillars 503, and the holding space 507 separates the fractionating pillars 506 from the holding pillars 503. The total amount of space among the holding pillars 503 is approximately equal to the total amount of space among the quantitative pillars 530b and the holding space 502. The quantitative pillars 530b are spaced from the holding pillars 503 wider than the holding spaces 505/507 between the holding pillars 503 and the introducing/fractionating pillars 504/506.

Sample is fractionated into fractions or microstructures different in size as follows. First, sample is gradually supplied through the feed port 520 into the quantitative passage 530a. The sample fills the quantitative passage 530a, and is held in the space among the quantitative pillars 530b. It is important that the sample does not overflow the feed port 520. As described hereinbefore, the sample is not fractionated in the quantitative pillars 530b.

The sample gradually percolates into the holding space 502, and reaches the boundary between the holding space 502 and the holding pillars 503. Then, the sample is attracted to the holding pillars 503, because the capillary action is stronger in the holding pillars 503 rather than in the quantitative pillars 530b. In other words, the total surface area of the holding pillars 503 is wider than the total surface area of the quantitative pillars 530b so that the holding pillars 503 gives rise to the capillary action stronger than the capillary action of the quantitative pillars 530b. Thus, all the sample is migrated from the quantitative passage 530a toward the holding pillars 503, and is held in the space among the holding pillars 503. While the sample is flowing into the space among the holding pillars 503, any piece of sample is never migrated to the fractionating pillars 506 and introducing pillars 504.

When the migration from the quantitative passage 530a to the space among the holding pillars 503 is completed, the buffer solution is supplied to the feed port 510. The buffer solution is migrated through the space among the introducing pillars 504, and reaches the boundary between the introducing pillars 504 and the holding space 505. The buffer solution is further supplied through the feed port 510 to the introducing pillars 504. The buffer solution percolates into the holding space 505, and flows into the space among the holding pillars 503. The buffer solution is migrated through the space among the holding pillars 503 into the holding space 507 together with the sample. The buffer solution and sample in turn are migrated into the space among the fractionating pillars 506. Since the quantitative pillars 530b are spaced from the holding pillars 503 wider than the holding spaces 505/507 are, the buffer solution does not flows into the space among the quantitative pillars 530b.

The buffer solution and sample are migrated through the fractionating pillars 506 toward the air hole 560 by virtue of the capillary action, and the sample is fractionated into microstructures different in size. When the buffer solution and sample reach the air hole 560, then the buffer solution does not flows into the feed port 510, and the fractions are recovered. A certain fraction may be recovered before the buffer solution reaches the air hole 560.

As will be understood, the sample accelerator 530 gives rise to the migration of the sample and buffer solution through the capillary action. The sample accelerator 530 is much simpler than the sample accelerators incorporated in the first and second embodiments, and is conducive to reduction in production cost of the apparatus.

Figure 9:
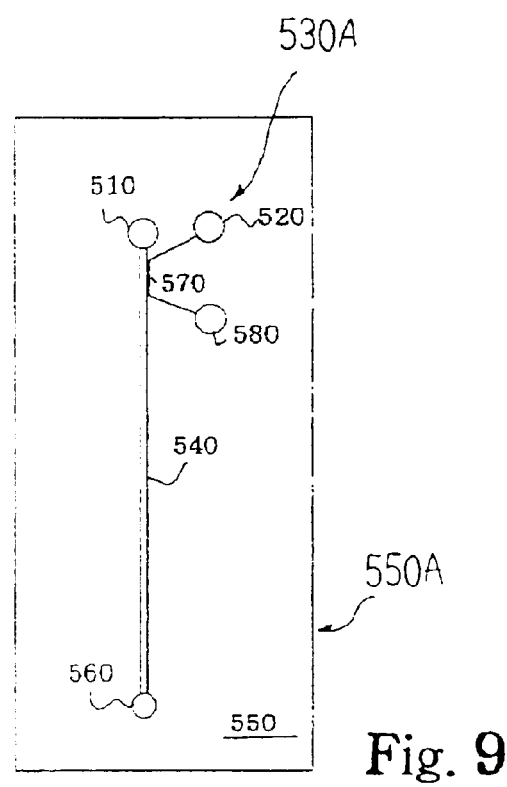
FIG. 9 is a schematic plane view showing the layout on a fractionating unit forming a part of a modification of the yet another apparatus according to the present invention.
Figure 10:
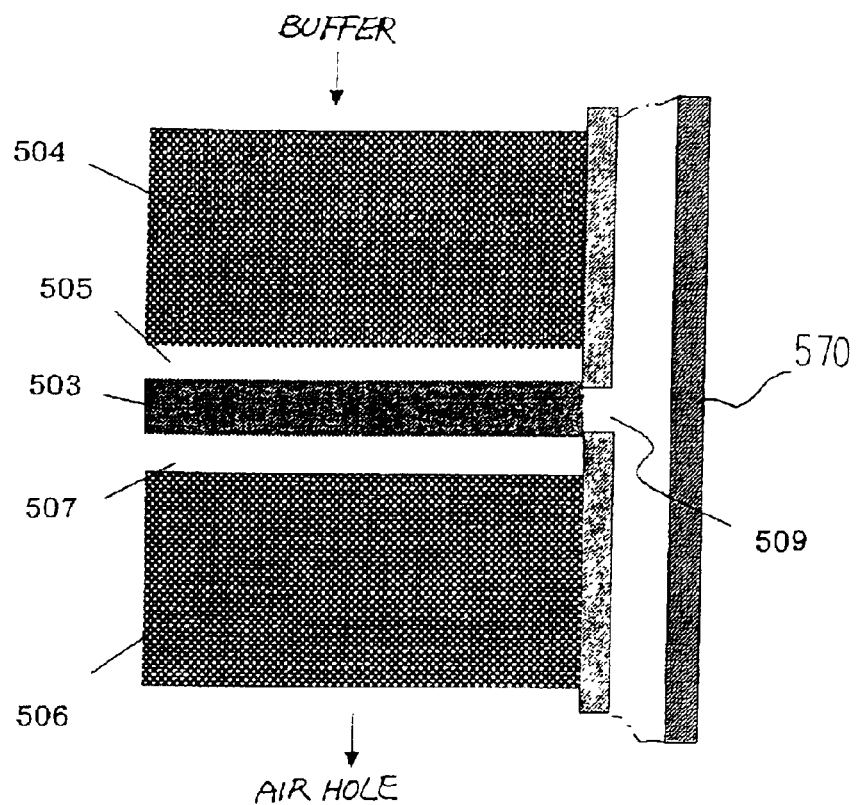
FIG. 10 is a schematic plane view showing a sample accelerator built in the fractionating unit.

A modification of the apparatus shown in FIGS. 7 and 8 is shown in FIGS. 9 and 10. The modification also comprises a fractionating unit 550A and a sample accelerator 530A. The fractionating unit 550B is implemented by an assemblage of a substrate 550b and a cover plate (not shown). A fractionating passage 540 is formed in the substrate 550b, and the feed port 510 and the air hole 560 are connected to both end portions of the fractionating passage 540. The introducing pillars 504, holding space 505, holding pillars 503, holding space 507 and fractionating pillars 506 are formed in the fractionating passage 540 as similar to the third embodiment.

The quantitative passage 530a is replaced with a feed passage 570. Any pillar is not formed in the feed passage 570, and is partially parallel to the fractionating passage 540. The feed passage 570 is connected to the fractionating passage 540 through an opening 509, and the holding pillars 503 occupies the area adjacent to the opening 509. A feeding port 520 and a drain port 580 are connected at both end portions of the feed passage 570.

Sample is supplied through the feed port 520 into the feed passage 570, and reaches the drain port 580. When the sample reaches the opening, 509, the sample is attracted to the holding pillars 503. When the sample fills the space among the holding pillars 503, then high-pressure air is blown into the feed port 520 so as to push out the residual sample from the feed passage 570.

Buffer solution is supplied through the feed port 510 into the fractionating passage 540. The buffer solution fills the space among the introducing pillars 504, and, thereafter, is migrated through the space among the holding pillars 503 to the fractionating pillars 506. The sample is fractionated into microstructures different in size.

Although the above-described modification gives rise to the migration of the sample/buffer solution through the capillary action, the electrophoresis is available for the modification. Prior to the introduction of the sample, liquid sumps, which are corresponding to the feed port 510 and air hole 560, are filled with electrophoresis buffer. The holding spaces 505/507 prohibit the electrophoresis buffer from flowing into the holding pillars 503. When the sample is stored in the space among the holding pillars 503, a small amount of electrophoresis buffer is supplied to one of the liquid sumps, or weak vibrations are imparted to the holding pillars 503. Then, the electrophoresis buffer is merged. A potential is applied for fractionating.

Fractionating Passage

Figure 11:
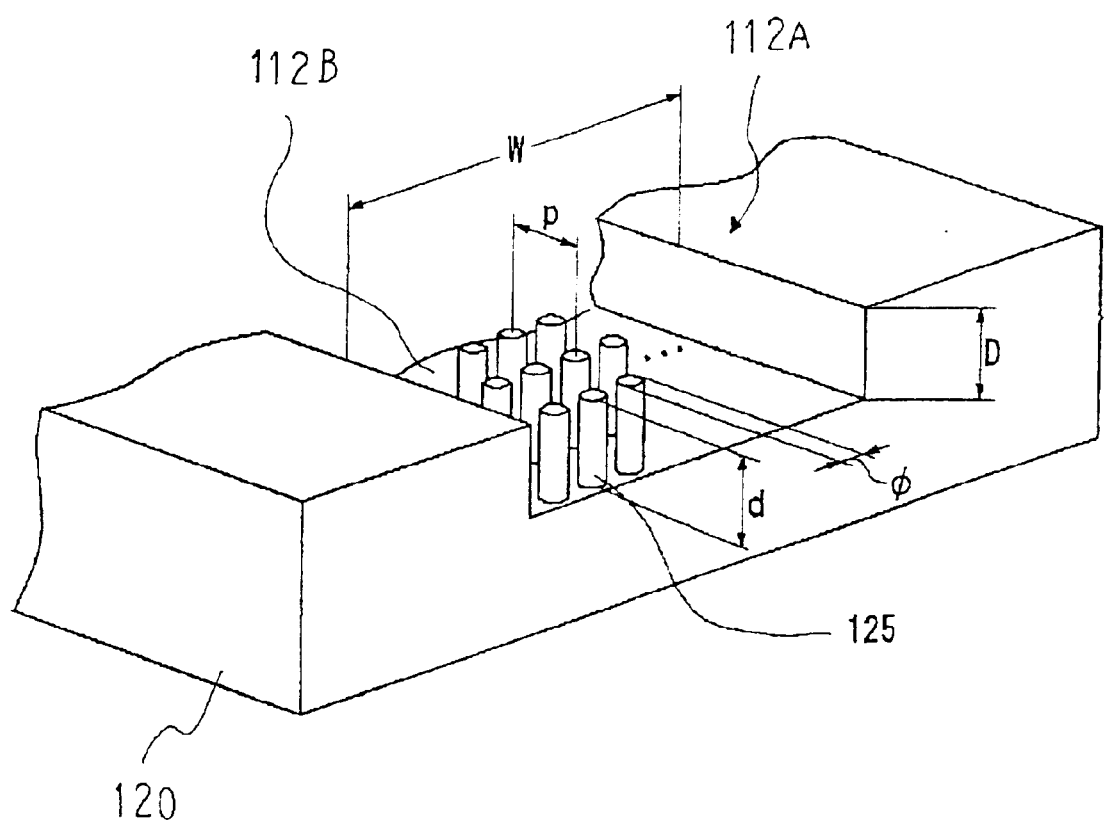
FIG. 11 is a schematic perspective view showing a structure in a fractionating passage formed in the substrates.

Description is hereinbelow made on structures in the fractionating passages sages 112/20a/540 formed in the substrates 110/20A/550/550A. FIG. 11 shows a fractionating passage 112A incorporated in a substrate 120. A groove 112B is formed in the substrate 120, and has a width W and a depth D. Pillars 125 are formed on the substrate 120, and project from the bottom surface defining the groove 112B. The pillars 125 have a configuration like a circular cylinder. The pillars 125 have a diameter $\Phi$ and a height d, and are arranged in matrix at regular intervals. The adjacent pillars 125 are spaced by the mean gap p. These measurements W, D, $\Phi$, D, d and p may be fallen within the following ranges.

| Measurements | Range |
|---|---|
| Width (W) | 10 microns–2000 microns |
| Depth (D) | 50 nanometers–3 microns |
| Diameter ($\Phi$) | 10 nanometers–100 nanometers |
| Height (d) | 10 nanometers–3 microns |
| Mean Gap (p) | 1 nanometer–10 microns |

Figure 12:
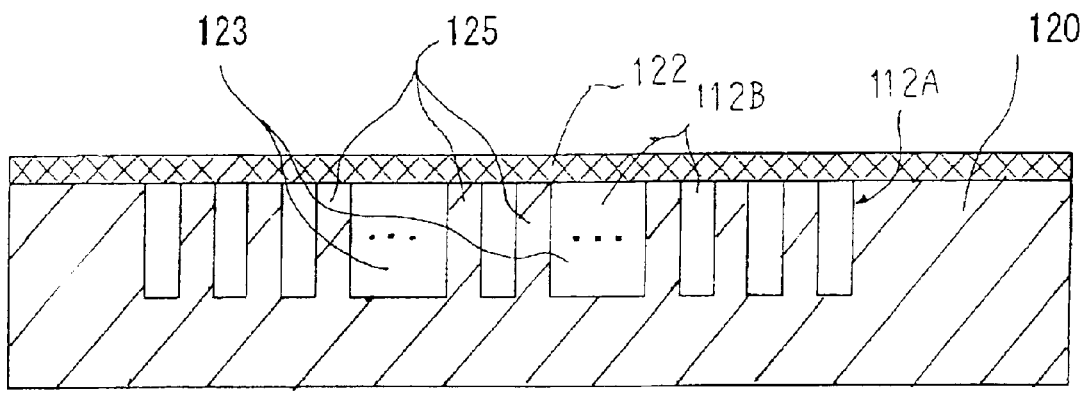
FIG. 12 is a schematic cross sectional view showing pillars formed in the fractionating passage.

FIG. 12 shows a cross section of the fractionating unit. The fractionating unit includes the substrate 120 and a cover plate 122. The groove 112B is formed in the substrate 120, and the pillars 125 are formed in the groove 112B. In this instance, all the pillars 125 are same in size, i.e., measurements. The pillars 125 form colonies of pillars. The major surface of the substrate 120 is overlaid with the cover plate 122. Although liquid sumps and/or ports are formed in the fractionating unit, they are omitted for the sake of simplicity. The space among the crows of pillars serves as a path 123. Thus, the fractionating passage 112A is broken down into the space occupied by the pillars 125 and the path 123. The sample and buffer solution flows through the path, and the sample is fractionated by means of the colonies of pillars 125. Thus, the sample and buffer solution are migrated through the fractionating passage 112A for the fractionation.

Figure 13:
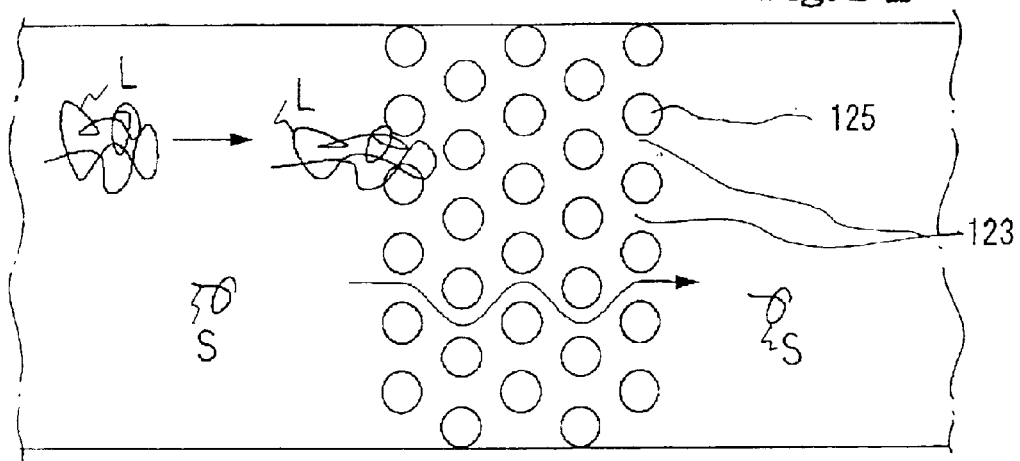
FIG. 13 is a schematic view showing microstructures migrated through the prior art fractionating passage.

If the pillars 125 are densely built up over the entire space of the groove 112B like the prior art apparatus, large-sized molecules L are much liable to be trapped in the pillars 125, and only small-sized molecules S can pass through the pillars 125 (see FIG. 13). This means that the fractionating passage tends to be clogged with the large-sized molecules L. In case where the sample contains many sorts of small-sized microstructures, the clogging is serious, because the pillars 125 are to be densely formed along the groove. The small-sized molecules S complete the migration faster than the large-sized molecules L do.

On the other hand, the pillars 125 according to the present invention forms colonies 121 of pillars 125, which are hereinbelow referred to as "pillar patches 121". The pillar patches 121 are spaced from one another so that a path 123 takes place among the pillar patches 121. The pillars 125 are arranged at regular intervals in the colony 121 or patch, and the gap between adjacent pillar patches 121 is wider than the intervals. It is preferable that the path 123 is twice to twentieth times wider than the gap between the adjacent pillars 125 in the patch. It is more preferable that the path 123 is five times to ten times wider than the gap between the adjacent pillars 125 in the patch 121.

Using the fractionating passage 112A, sample is fractionated as follows. The sample is supplied to one end of the fractionating passage 112A. The large-sized microstructures such as large-sized molecules L are migrated through the path 123 without being trapped in the colonies 121 as indicated by arrow AR1. However, small-sized microstructures such as small-sized molecules S are much liable to be trapped in the pillar patches 121. The pillars 125 define a labyrinth in the patch 121, and the small-sized molecules S are to be migrated in the labyrinth as indicated by arrow AR2. This is time-consuming so that the small-sized molecules S are delayed. The smaller the size of the microstructures, the longer the time consumed. This results in that the small-sized molecules S reaches the end of the fractionating passage 112A after the large-sized molecules L. Thus, the fractions, i.e., the microstructures such as molecules are output from the fractionating passage 112A in order of size. Since the large-sized molecules L are smoothly migrated through the path 123, the fractionating passage 112A is less liable to be clogged with the large-sized molecules. This means that the throughput is enhanced. Thus, the fractionating passage 112A according to the present invention achieves a high throughput.

Figure 15:
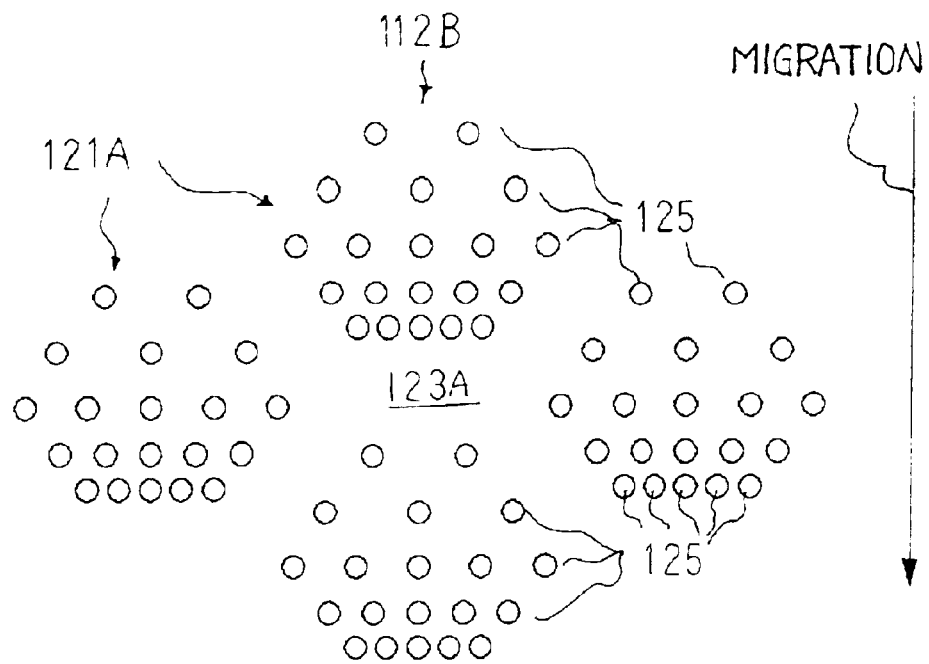
FIG. 15 is a plane view showing the arrangement of a modification of a pillar patch.
Figure 16:
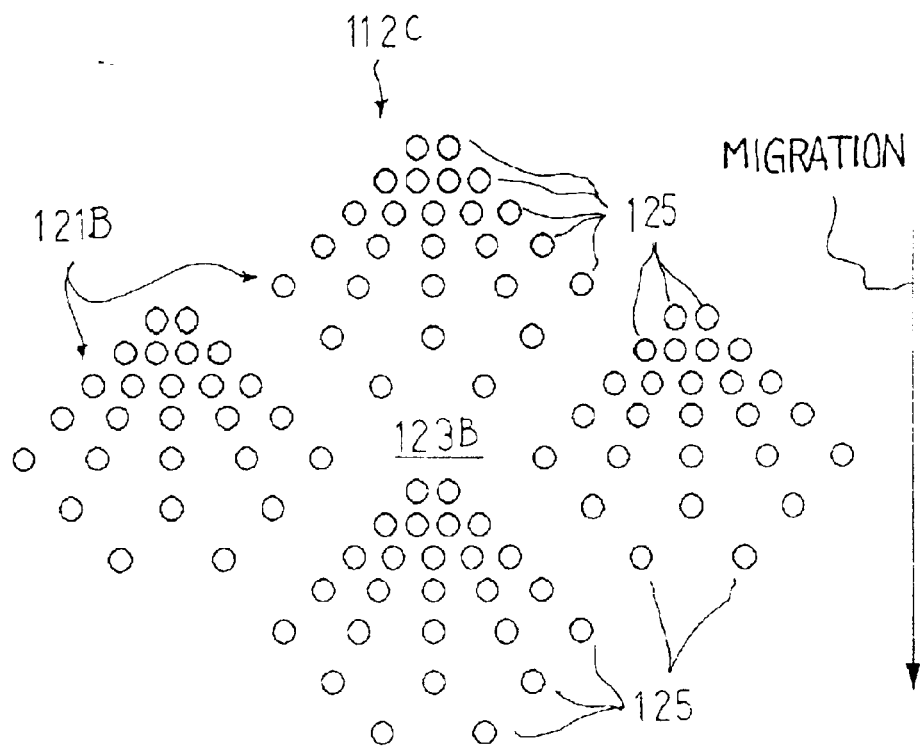
FIG. 16 is a plane view showing the arrangement of another modification of the pillar patch.

FIGS. 15 and 16 show modifications of the pillar patch. Pillar patches 121A shown in FIG. 15 are provided in the fractionating passage 112B. The pillar patches 121A are spaced from one another so as to define the path 123A. Sample and buffer solution are migrated along the fractionating passage 112B as indicated by arrow. The pillars 125 are arranged at irregular intervals in the patch 121A. The interval or gap between adjacent pitches 125 is decreased toward the downstream. In this instance, the pillars 125 on the down-stream side give larger resistance against the migration of microstructures than the pillars 125 on the upstream side do. For this reason, the time lug between large-sized microstructures, which are migrated through the path 123A, and small-sized microstructures, which are trapped in the pillar patches 121A, is longer than the time lug introduced by the pillar patches 121. Thus, the pillar patches 121A enhances the resolution on the sample.

Pillar patches 121B shown in FIG. 16 are also provided in the fractionating passage 112C. The pillar patches 121B are spaced from one another so as to define the path 123B. Sample and buffer solution are migrated along the fractionating passage 112C as indicated by arrow. The pillars 125 are arranged at irregular intervals in the patch 121B. The interval or gap between adjacent pitches 125 is increased toward the downstream. Microstructures are migrated in the labyrinth of the pillar patch 121B smoother than the microstructures in the labyrinth of the pillar patch 121A. For this reason, the pillar patches 121B are conducive to the enhancement of the throughput.

Figure 14:
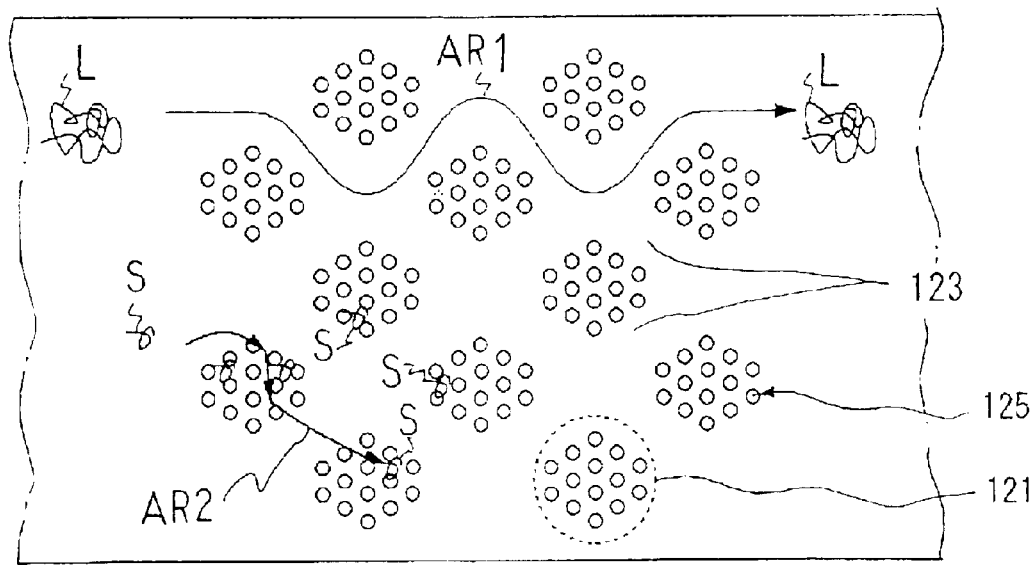
FIG. 14 is a schematic view showing microstructures migrated through the fractionating passage formed in the fractionating unit according to the present invention.
Figure 17:
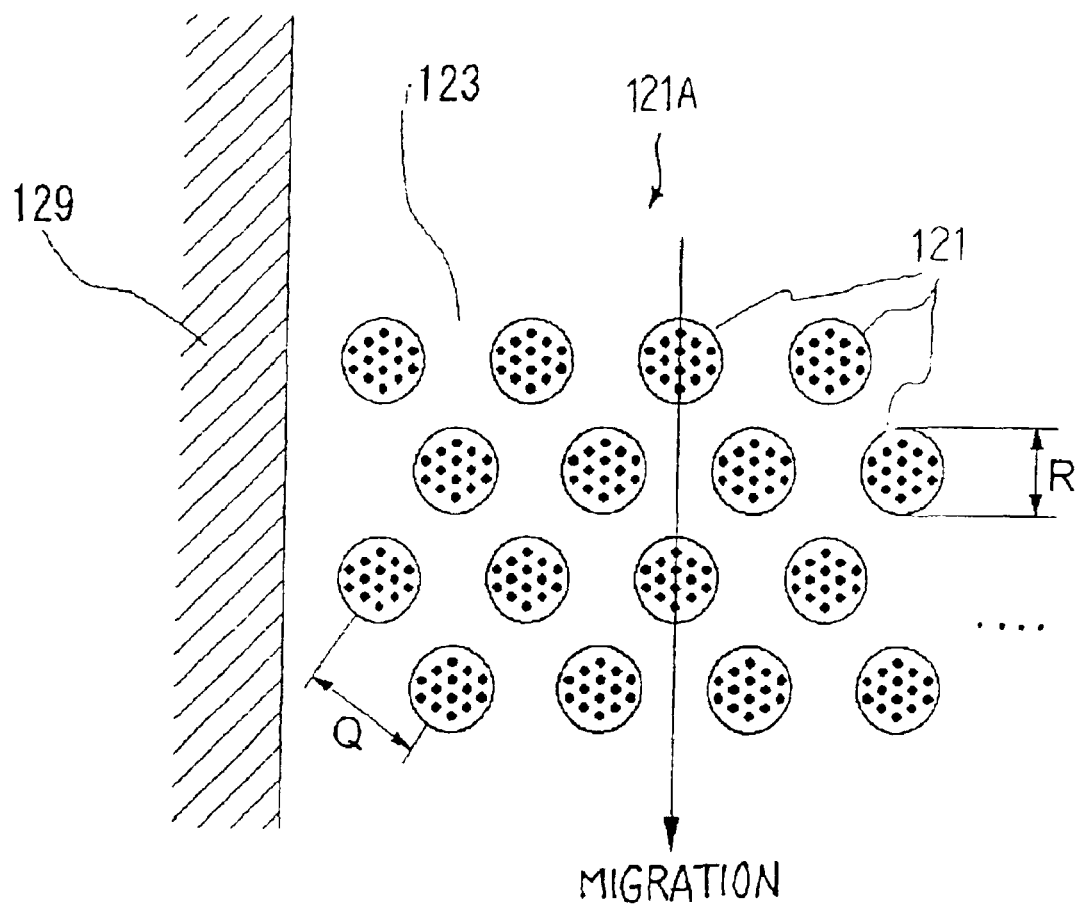
FIG. 17 is a plane showing the layout of pillar patches in the fractionating passage.

Turning back to FIG. 14 of the drawings, the pillars 125 are arranged at regular intervals in the patch 121 as described hereinbefore. The pillar patches 121 are further arranged in regular intervals between the side walls 129 defining the fractionating passage 121A as shown in FIG. 17. The pillar patches occupy circular areas in the fractionating passage 121A, and the circular areas have a diameter R. The gap between the adjacent pillar patches 121 serves as the path 123, and Q represents the gap between the adjacent pillar patches 121. In this instance, the gap Q is twice as wide as the diameter R. For example, the diameter R is equal to or less than 10 microns, and the gap Q is equal to or less than 20 microns.

Figure 18:
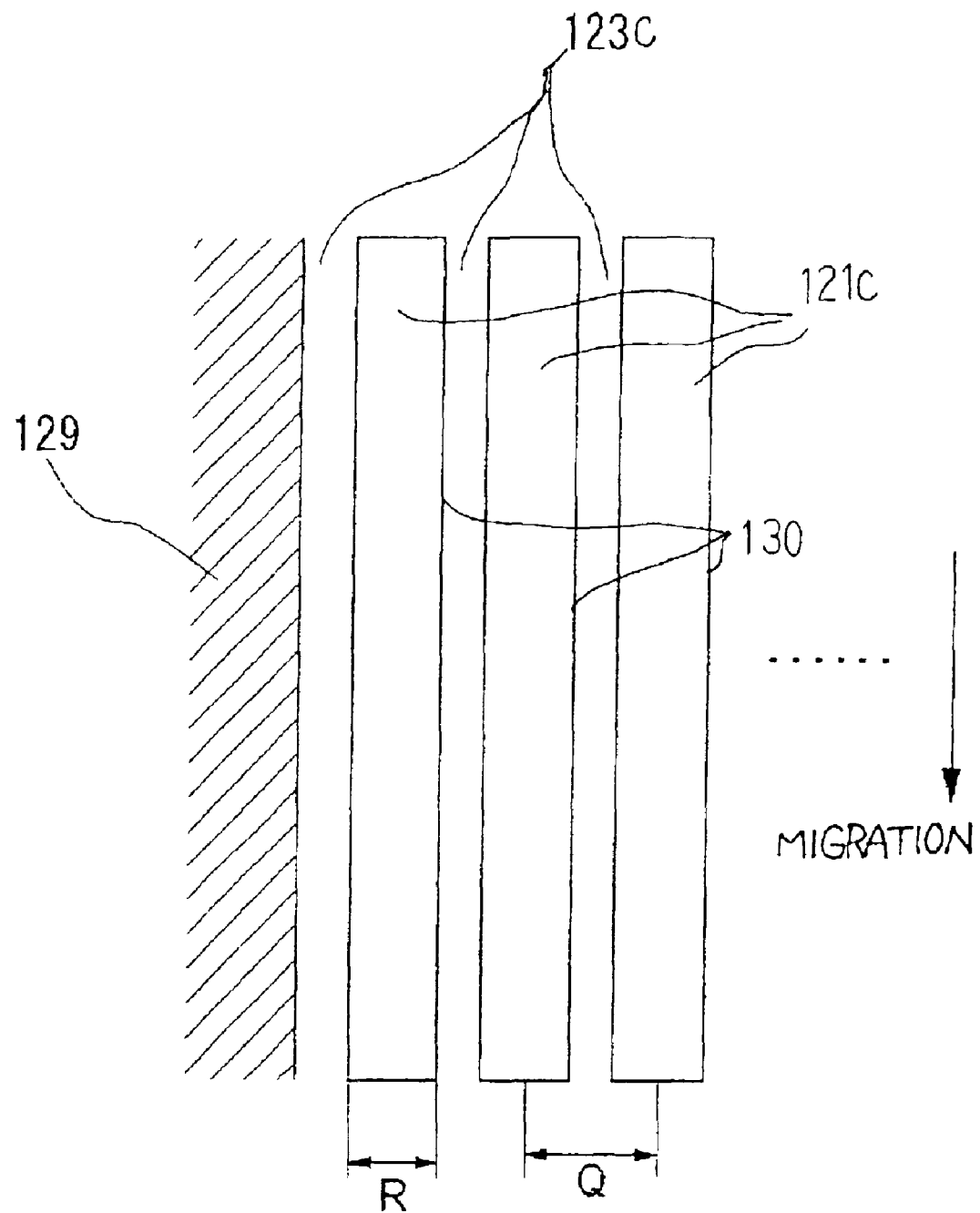
FIG. 18 is a plane view showing a modification of pillar patches.

The circular area does not set any limit to the pillar patches 121. In another modification, pillar patches 121C occupy rectangular areas as shown in FIG. 18. The rectangular areas have a width R equal to or less than 10 microns, and the mean gap Q ranges from 10 microns to 100 microns. A path 123C is defined among the pillar patches 121C, and extends in parallel to the direction of migration.

Figure 19:
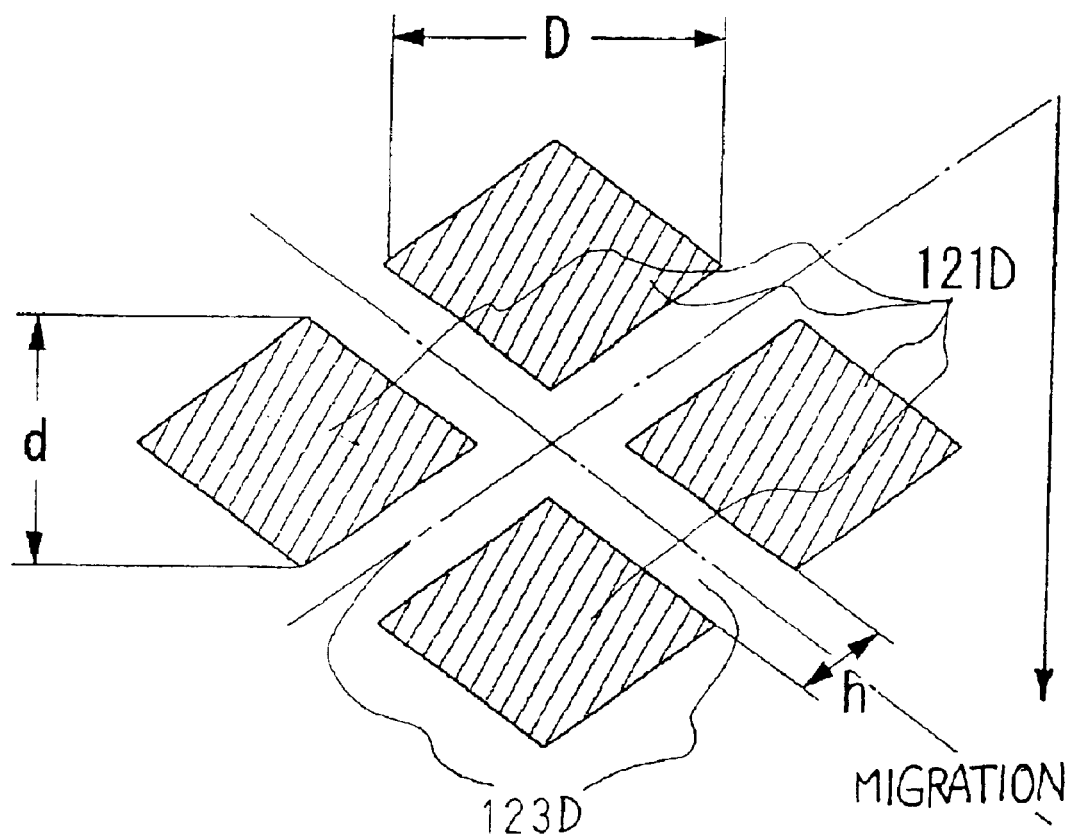
FIG. 19 is a plane view showing another modification of pillar patches.

Yet another modification may have pillar patches 121D, which occupy rhomboid areas as shown in FIG. 19. The fractionating passage extends in the direction of arrow. D is a diagonal measured in perpendicular to the direction of migration, and d is another diagonal measured in parallel to the direction of migration. A path 123D is defined among the rhomboid areas, and has a width h. In other words, the pillar patches 121D are spaced apart from one another by the distance h. Centerlines of the path 123D are indicated by dot-and-dash lines. The centerlines cross the direction of migration at certain angles. While sample is migrated along the fractionating passage, microstructures are repeatedly brought into contact with the pillar patches 121D. This means that certain microstructures, the size of which is less than the gap between adjacent pillars, are much liable to be trapped in the pillar patches 121D. This results in a long time lug between the certain microstructures and other microstructures. Thus, the path inclined to the direction of migration is preferable from the viewpoint of high resolution. It is preferable to fulfill the following conditions for separating target microstructure from the sample at good fractionating efficiency. R is representative of the diameter of the target microstructures, and p stands for the gap between adjacent pillars in the pillar patch 121D.

Figure 20:
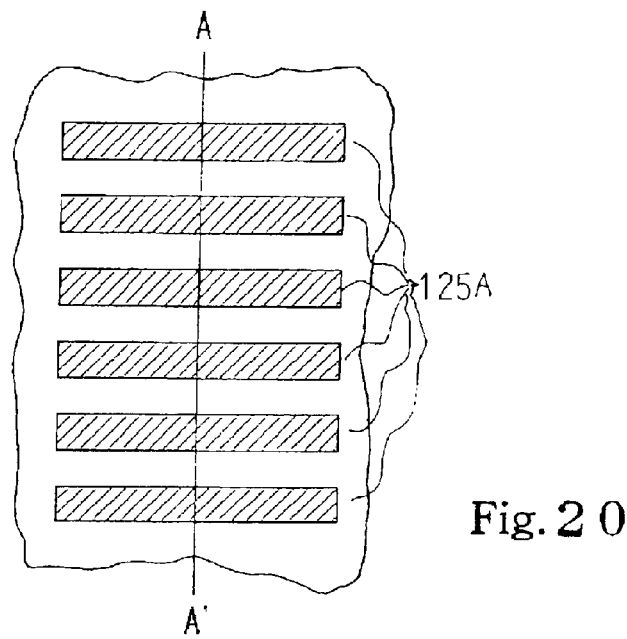
FIG. 20 is a plane view showing the layout of yet another modification of a pillar patch.
Figure 21:
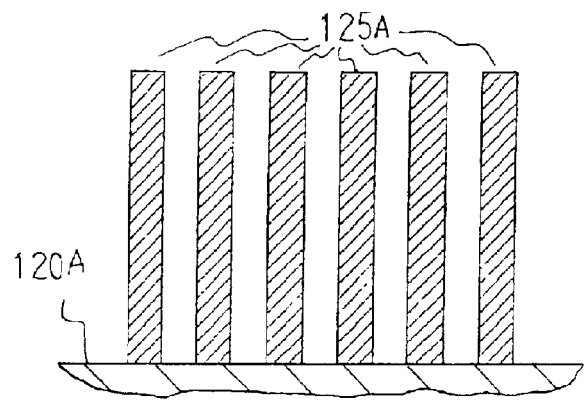
FIG. 21 is a cross sectional view taken along line A–A' of FIG. 20, and showing the structure of the pillar patch.
Figure 22:
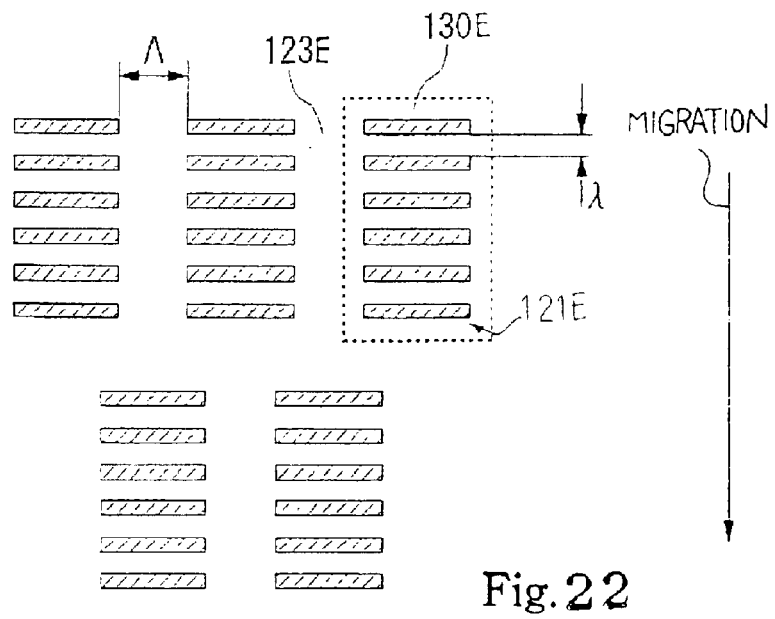
FIG. 22 is a plane view showing the arrangement of pillar patches.

$h: R \leq h < 10R$ $p: 0.5R \leq p < 2R$ $D: 5h \leq D < 20h$ $d: 5h \leq d < 20h$ FIGS. 20, 21 and 22 show still another modification of the pillar patch 121. Pillars 125A have a plate-like configuration, and are upright on the bottom surface defining a groove, which is formed in a substrate 120A of a fractionating unit. The plate-like pillars 125A are arranged in parallel at intervals of λ. The plate-like pillars 125A form a pillar patch 121E which occupies a rectangular area 130E. The adjacent pillar patches 121E are spaced from one another by gap Λ, and a path 123E takes place among the pillar patches 121E. Sample is migrated in the direction of an arrow (see FIG. 22). The pillar patches 121E form rows, which extend in the direction perpendicular to the direction of the migration. The pillar patches 121E in a row are offset from the pillar patches 121E in the next row. Thus, the pillar patches 121E are arranged in a staggered manner.

While sample is migrated together with buffer solution in the direction indicated by the arrow, target microstructures are trapped in the pillar patches 121E. The target microstructures thus trapped stays in the pillar patches 121E for a long time. This results in a long time lug between the arrival of the target microstructures and the arrival of other microstructures. Thus, the pillar patches 121E enhances the resolution.

In case where the target microstructures have a diameter R, it is preferable to fulfill the following conditions for separating the target microstructures from the sample at high fractionating efficiency.

$\Lambda: R \leq \Lambda < 10R$ $\lambda: 0.5 R \leq \lambda < 2R$.

Figure 23:
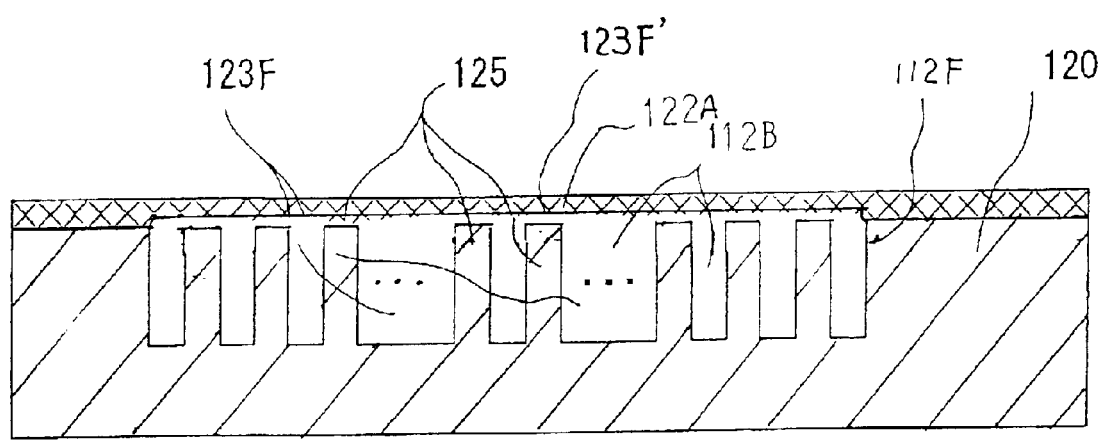
FIG. 23 is a cross sectional view showing the structure of yet another fractionating passage.

In the fractionating unit shown in FIG. 12, the top surfaces of the pillars 125 are held in contact with the reverse surface of the cover plate 122, and the pillars 125/125A in the other fractionating units also have the top surfaces held in contact with the reverse surfaces of the cover plates. In yet another modification, although the pillars 125 are as tall as those shown in FIG. 12, the top surfaces of the pillars 125 are spaced from the reverse surface of the cover plate 122A as shown in FIG. 23. The gap between the pillars 125 and the cover plate 122A serves as another path 123F' for large-sized microstructures. Thus, a fractionating passage 112F has not only path 123F among the pillar patches but also the path 123F' between the pillars and the cover plate 122A. The large-sized microstructures are migrated through the path 123F' more smoothly so that the fractionating passage 112F is less clogged with the large-sized microstructures. The path 123F' offers entrances to small-sized microstructures. While the small-sized microstructures are migrated through the path 123F' together with the large-sized microstructures, the large-sized microstructures pass over the pillar patches, and the small-sized microstructures enter the pillar patches through the entrances at the boundaries between the path 123F' and the pillar patches. Thus, the path 123F' increases the probability of the entry into the pillar patches so as to enhance the fractionating efficiency. In the modification shown in FIG. 23, the recess formed in the cover plate 122A serves as the path 123F'. The path 123F' may be formed by replacing the tall pillars with short pillars.

A modification of the fractionating unit, a fractionating passage 112G further includes a row of pillars 710 in front of the fractionating region 711 where the pillar patches occupy as shown in FIGS. 24A to 24D. The pillars are arranged in the row 710 at regular intervals. It is preferable to adjust the intervals to a value as small in value as the measure of the minimum molecules in sample 709 or a colony of molecules different in size.

Figure 24A:
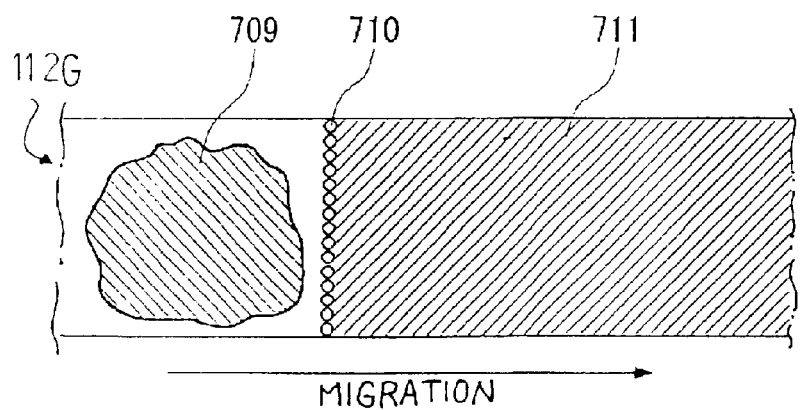
FIGS. 24A to 24D are plane views showing sample forced to pass a row of pillars provided in front of a fractionating region.
Figure 24B:
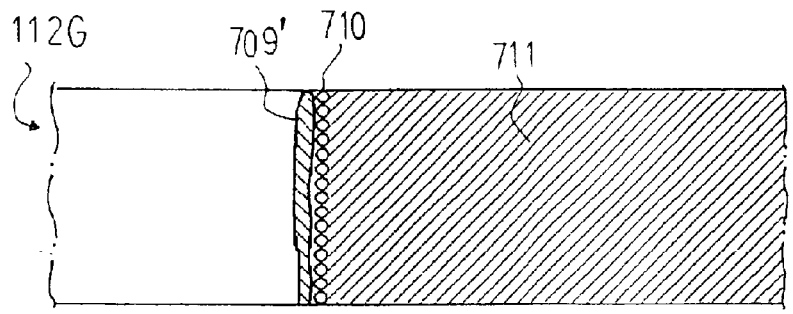
Figure 24C:
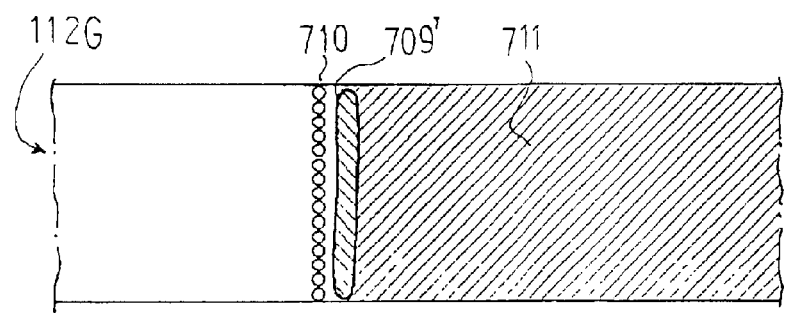
Figure 24D:
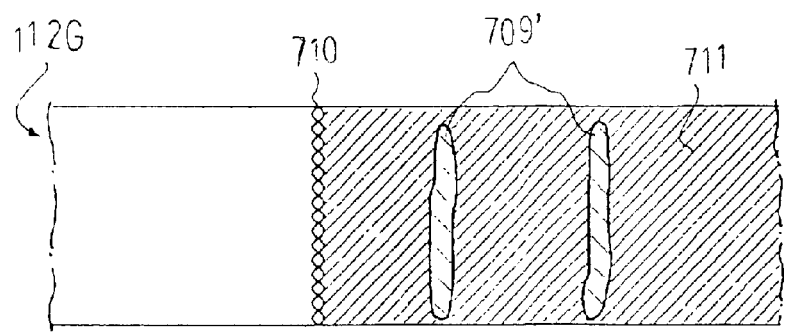

The row of pillars 710 behaves as follows. Weak force such as weak electric force is assumed to be exerted on the sample 709. The sample is migrated grated in the direction of an arrow (see FIG. 24A). When the sample reaches the row of pillars 710, the row of pillars 710 impedes the migration of the sample 709 like a dam. Since the weak force is still exerted on the sample 709, the sample is crashed on the row of pillars 710, and is reshaped in a band 709' as shown in FIG. 24B. The force is changed from the weak force to strong force. In this instance, the electric force is exerted on the sample 709 in the electric field, strong electric field is created along the fractionating passage sage 112G. Then, the band-shaped sample 709' is forced to pass the row of pillars 710, and enters the fractionating region 711 as shown in FIG. 24C. In detail, if the pillars are made in a single row of several rows, macromolecules such as DNA and proteins are prolonged at the boundary of the row or rows so that the macro-molecules can pass through the gaps, which are narrower than the measure of the macro-molecules. The phenomenon is called as "reptation". The force is regulated to a proper value after passing through the row of pillars 710. The band-shaped sample 709' is migrated through the fractionating region 711 so that the sample is fractionated into fractions different in size (see FIG. 24D).

As to the width of the path 123A/123B/123C/123D/123E and the gap of adjacent pillars or the intervals of the pillars, the width and the gap/intervals are to be designed depending upon fractions in sample. The fractions are organic molecules such as nucleic acids, amino acids, peptides and proteins and other molecules/ions such as chelate compounds and metal ions, by way of example. It is preferable that the gap or intervals are equal to, slightly greater than or slightly less than the inertia radius of curvature of the medium-sized molecules which is equivalent to the median of the molecules to be separated. When the difference between the inertia radium of curvature equivalent to the median and the intervals is equal to or less than 100 nanometers, the sample is fractionated into fractions at high resolution. It is more preferable that the difference is equal to or less than 10 nanometers. It is most preferable that the difference is equal to or less than 1 nanometer. When the difference is decreased, the resolution is enhanced.

The path is designed in such a manner that the with is equal to, slightly greater than or slightly less than the inertia radius of curvature of the maximum-sized molecules. It is preferable that the difference between the width of path and the inertia radius of curvature of the maximum molecules is equal to or less than 10% of the inertia radium of curvature. It is more preferable that the difference is equal to or less than 5%. It is most preferable that the difference is equal to or less than 1%. If the path is too wide, small-sized molecules are migrated together with large-sized molecules, and the fractionation is incomplete. On the other hand, if the path is too narrow, the path is liable to be clogged.

The gap between the adjacent pillars in a certain patch is varied in the modification shown in FIGS. 15 and 16. When the gap is varied in the direction of migration, the resolution is improved, or the fractionating passage is prevented from the clogging. Pillar patches, in which the gap is varied, are further conducive to the fractionation of sample into more than two sorts of fractions different in size.

Figure 25:
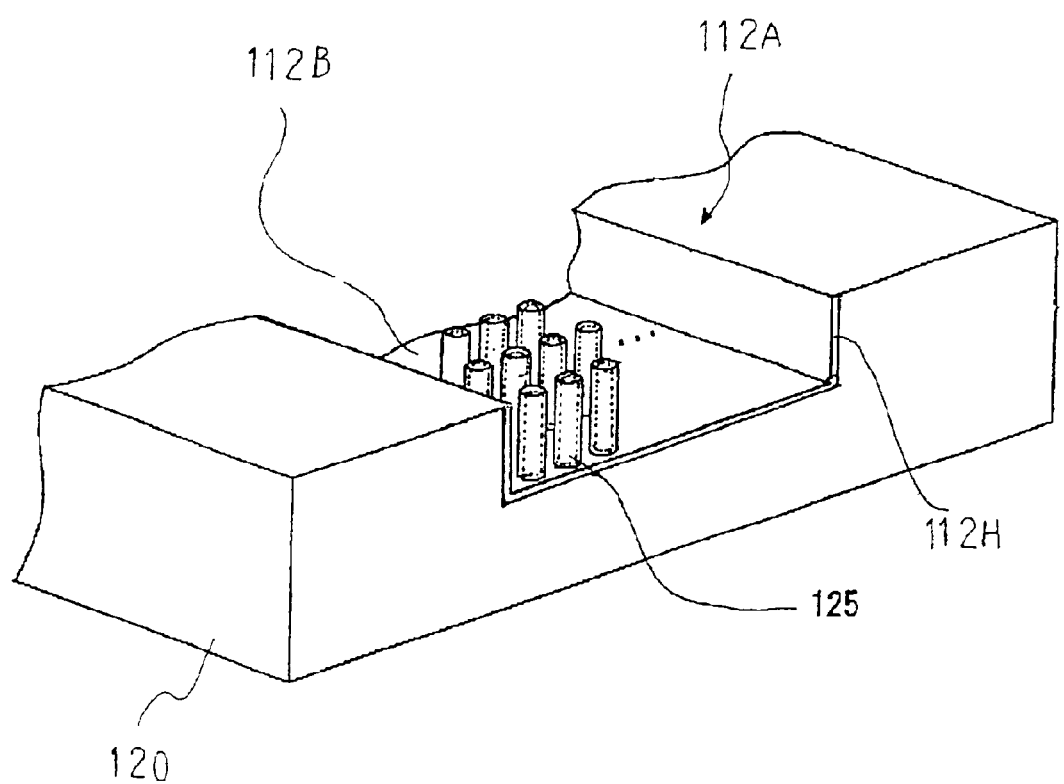
FIG. 25 is a schematic perspective view showing the walls of a groove coated with a smoothing layer.

The walls, which define the groove 112A/112B may be coated with certain material as shown in FIG. 25. The coating layer is designated by reference 112H. The coating material makes the surfaces smooth, and the coated walls are effective against adhesion of molecules such as DNA and proteins thereto. It is preferable that the coating material has the structure analogous to that of the phospholipid which forms the cell membrane. The coating material is commercially obtainable. Nippon Yusi Corporation limited sells the coating material as "Lipidure" (trademark). The coating material "Lipidure" is dissolved in TBE buffer solution, and the concentration is regulated to 0.5 weight %. The solution is spread over the walls, and dried for several minutes. Then, the walls are coated with the smoothing layer 112H. The smoothing layer 112H may be made of fluorine-contained resin or bovine serum albumin.

Figure 26:
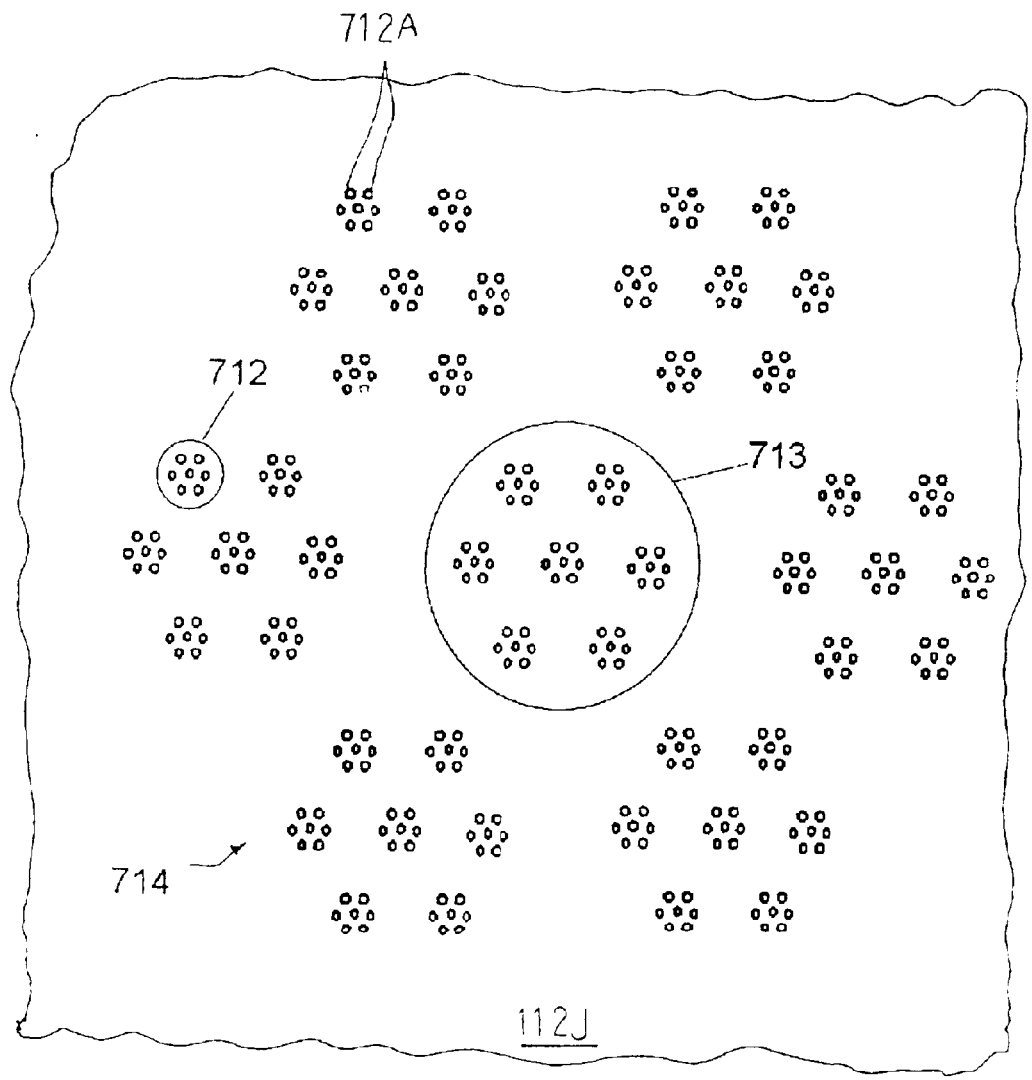
FIG. 26 is a plane view showing the arrangement of colonies of pillar patches in a fractionating passage.

The pillars may be hierarchically arranged as shown in FIG. 26. The gap between adjacent pillar patches 712 is wider than the gap between adjacent pillars 712A. Every seven pillars 712A form pillar patches 712. Seven pillar patches 712 are gathered, and form a small colony 713 of pillar patches. The gap between adjacent colonies 713 is wider than the gap between adjacent pillar patches 712. Seven colonies 713 of pillar patches are further gathered, and form a large colony 714 of pillar patches 712. Although only one large colony 714 is drawn in FIG. 26, plural large colonies 714 are formed in a fractionating passage 112J. Thus, the pillars are hierarchically arranged in the fractionating passage 112J. While sample is migrated through the fractionating passage 112J, huge microstructures pass through the widest path among the large colonies 714 of pillar patches 712, large-sized microstructures pass through the labyrinth among each large colonies 714, middle-sized microstructures pass through the labyrinth among each small colony 713, and small-sized microstructures pass through the labyrinth in each pillar patch 712. Thus, the huge microstructures firstly reach the end of the fractionating passage 112J, the large-sized microstructures reaches the end of the fractionating passage 112J next to the huge microstructures, the middle-sized microstructures follows the large-sized microstructures, and the small-sized microstructures finally reach the end of the fractionating passage 112J.

Sample Accelerator

Figure 27:
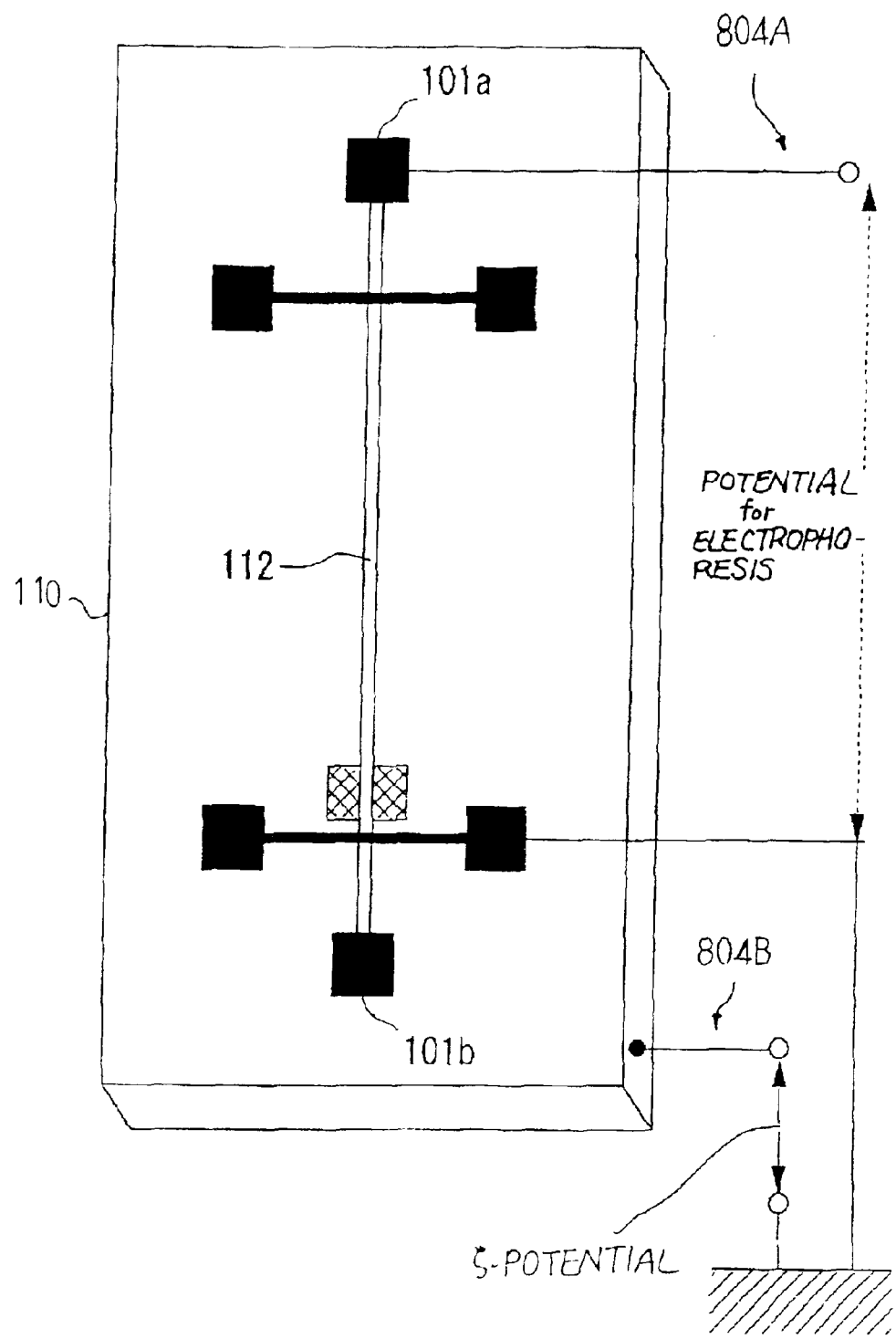
FIG. 27 is a schematic perspective view showing the arrangement of a modification of the sample accelerator.

Two sorts of sample accelerator have been already described with reference to FIGS. 2–4 and 5. FIG. 27 shows a modification of the sample accelerator 804A. In the modification, $\zeta$-potential is applied to the substrate 110. Sample is migrated through the fractionating passage 112 by means of the electrophoresis. The $\zeta$-potential is applied to the substrate 110 for the sake of restriction against electroosmosis. Thus, the $\zeta$-potential system 804B is effective against the broadening at the peak in the measurement.

Introduction of Buffer Solution

In the apparatus according to the present invention, it is preferable to introduce buffer solution. If the walls of the substrates and reverse surface of the cover plate which define the fractionating passage are hydrophobic such as hydrophobicity of synthetic resin, it is not easy to feed the buffer solution into the fractionating passage. From the viewpoint that the buffer solution is to be smoothly fed into the fractionating passage, a centrifugal system may be used.

Figure 28:
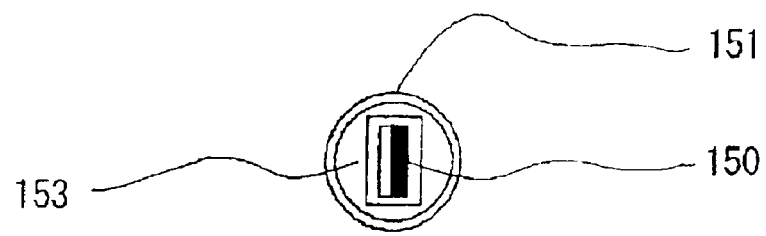
FIG. 28A is a plane view showing a chip in a tube of a centrifugal system.
FIG. 28B is a cross sectional view showing the chip accommodated in the tube.
Figure 28:
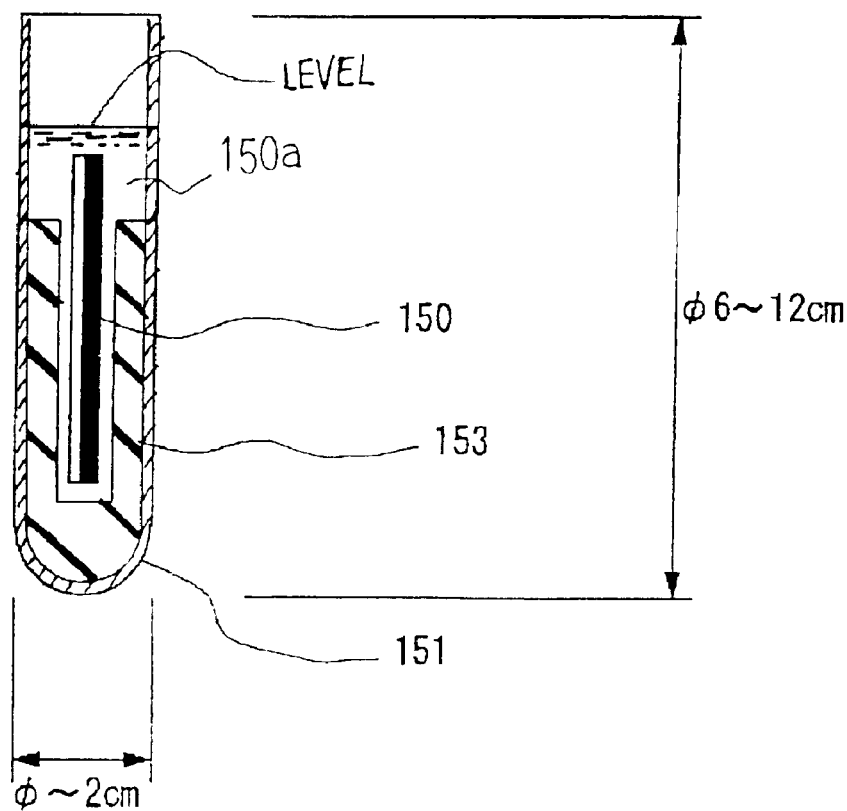

FIGS. 28A and 28B show a chip 150 into which buffer solution is forcibly introduced. A holder 153 is inserted into a centrifugal tube 151, and is formed with a deep recess. In this instance, the holder is made of silicone rubber. The chip, which is equivalent to the fractionating unit, i.e., the substrate and cover plate, is inserted into the deep recess, and the centrifugal tube 151 is filled with buffer solution 150a. The chip 150 is fixed to the holder 153. The centrifugal tube 151 is assembled with the centrifugal system, and is rotated at high speed. The centrifugal force is exerted on the buffer solution 150a, and is forcibly introduced into the chip 150.

A hydrophilic surface is preferable for buffer solution. The surfaces defining the fractionating passage and the surfaces of pillars may be covered with hydrophilic layers. Silicon oxide is an example of the hydrophilic material. It is preferable to cover the walls defining the groove and the entire surface of the pillars with the silicon oxide. Even though any external force is exerted on the buffer solution, the hydrophilic surfaces permit the buffer solution to flow into the fractionating passage. The surfaces covered with silicon oxide will be hereinafter described in detail.

Pillars

It is preferable that the pillars have top surfaces narrower than the cross sections of the base portions thereof. The pillars may have a cone/pyramid form or a frustum thereof. If the pillars have the cone/pyramid form or the frustum thereof, the cross sectional area is decreased toward the tops of the pillars. In case where the pillars are covered with hydrophilic layers such as silicon oxide layers, the pillars, the cross sectional area of which are decreased toward the tops, are effective against reduction of the aspect ratio.

It is more preferable that the pillars, the cross sectional area of which are decreased toward the tops, are merged with one another at the bottoms of valleys in the pillar patches. The growth of silicon oxide is restricted at the bottoms of the valleys so that the pillars keep the aspect ratio large. FIG. 1 shows the pillars 110 covered with the silicon oxide layer 104. The pillars 110 are respectively defined by gentle robes, and the gentle robes are merged with one another at the bottom of the valley 110V. While silicon oxide is thermally growing on the pillars 110, the growth is restricted at the bottom of the valley 110V, and the silicon oxide layer 104 at the bottom of the valley 110V is not so thick as the silicon oxide layer 104 on the remaining gentle robes. The silicon oxide at the bottom of the valley 110V does not swell into an eminence. In other words, the valley 110V is never buried with the silicon oxide. Thus, the pillars 110 keep themselves at the high aspect ratio. It is not sure why the merged robes restrict the growth of silicon oxide. Nevertheless, it is considered that the compressive stress suppresses the growth of silicon oxide. While the silicon is being oxidized, the pillars are increased in volume, and the compressive stress exerted on the silicon oxide at the bottom is enlarged with the progress of the oxidation. The large compressive stress is considered to suppress the growth of silicon oxide.

In the above-described embodiments and modifications, the fractionating region is implemented by the pillar patches, i.e., colonies of pillars. Caron nanotubes or carbon nanohorns are available for the fractionating region. The carbon nanotubes or carbon nanohorns are formed in the groove, and form colonies in a similar manner to the pillar patches. The carbon nanotubes are micro-tubes having diameter of 1 to 30 nanometers, and the carbon nanohorns are horn-like micro-projections, which measure 4 nanometers at the base portions thereof and 1 nanometer at the top portions thereof.

The pillars, carbon nanotubes and carbon nanoporns serve as microbodies.

Process of Fabricating

Description is hereinbelow made on a process for forming the pillars shown in FIG. 1 with reference to FIGS. 29A to 29G. FIGS. 29A to 29G show a part of the substrate 110 where a groove has been already formed.

The process starts with preparation of the substrate 110. Silicon oxide is deposited over the entire surface of the substrate 110, and forms a silicon oxide layer 105. Subsequently, electron beam resist is spread over the entire surface of the silicon oxide layer 105, and an electron beam resist layer 107 is formed on the silicon oxide layer 105. Thus, the silicon oxide layer 105 and electron beam resist layer 107 are laminated on the bottom surface defining the groove as shown in FIG. 29A.

The resultant structure is placed in an electron beam lithography system, and a pattern of pillars is written in the electron beam resist layer 107 with an electron beam. In other words, a latent image of the pattern is produced in the electron beam resist layer 107, and the latent image is developed so that a resist mask 107a is made from the electron beam resist layer 107 as shown in FIG. 29B.

Figure 29:
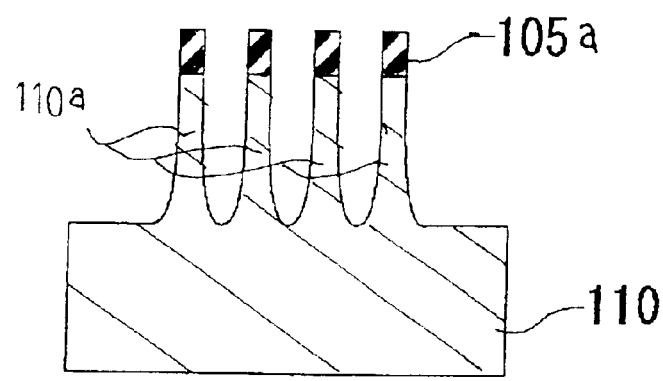
FIGS. 29A to 29G are cross sectional views showing a process for forming pillars of a fractionating unit.
Figure 29:
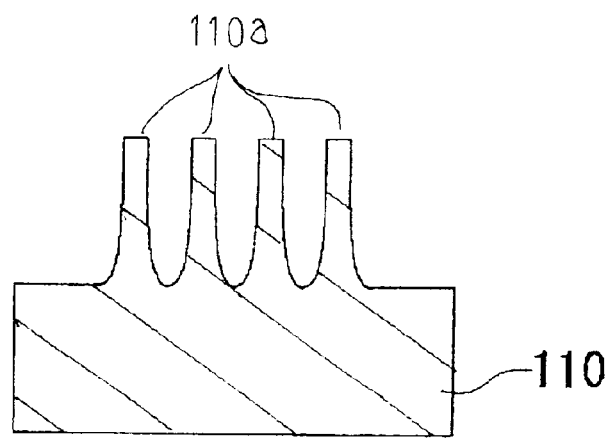
Figure 29:
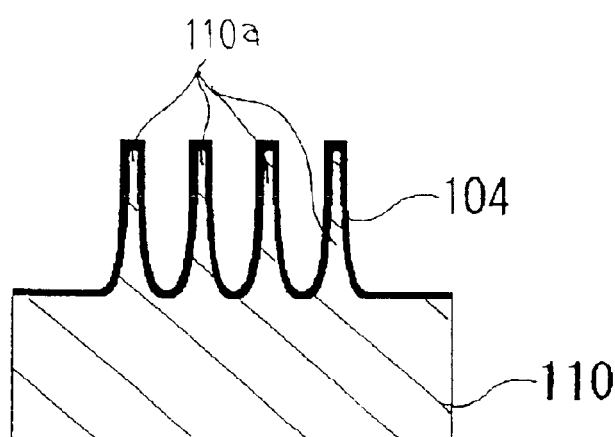

Using the resist mask 107a, the silicon oxide layer 105 is selectively removed by using a dry etching as shown in FIG. 29C. Thus, the pattern is transferred from the resist mask 107a to the silicon oxide layer 105, and a hard mask 105a is left on the bottom surface of the substrate 110. The resist mask 107a is stripped off. The resultant structure is shown in FIG. 29D.

Using the hard mask 105a, the substrate 110 is selectively removed by using a dry etching so that pillars 110a are formed as shown in FIG. 29E. The etching deeply proceeds into the substrate 110 so that the pillars 110a have a large aspect ratio. The hard mask 105a is stripped off, and the pillars 110a are left on the bottom surface of the substrate 110 as shown in FIG. 29F. Subsequently, the substrate 110 is placed in a furnace, and is heated to or over 850 degrees in centigrade in oxidizing atmosphere. Silicon oxide is thermally grown on the entire surface of the substrate 110, and the pillars 110a are covered with a silicon oxide layer 104 as shown in FIG. 29G. The pillars 110a covered with the silicon oxide layer 104 are a sort of nanostructure, and are available for the fractionation of sample containing microstructures different in size.

Figure 30A:
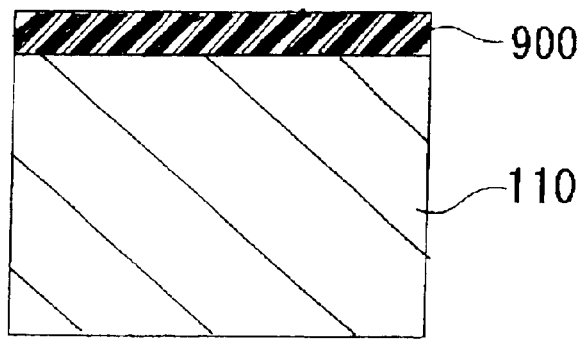
FIGS. 30A to 30C are cross sectional views showing another process for forming pillars of a fractionating unit.
Figure 30B:
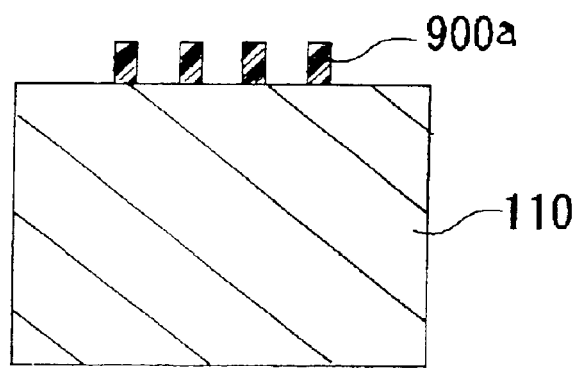
Figure 30C:
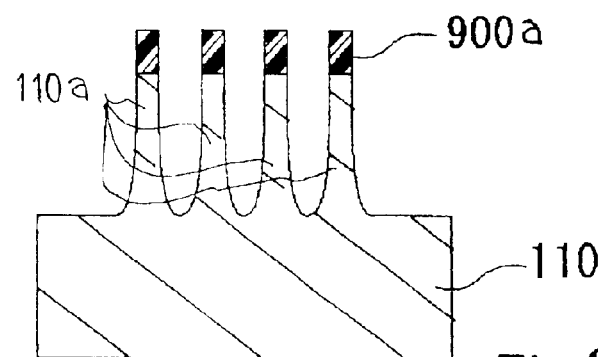

The pillars 110a may be formed on the bottom surface of the substrate 110 through a process shown in FIGS. 30A to 30C. In the process shown in FIGS. 29A to 29G, the pattern of pillars is indirectly transferred to the substrate 110. However, the pattern is directly transferred to the substrate 110 in the following process. First, the substrate 110 is prepared.

The electron beam resist is formed on the bottom surface of the substrate 110, and a pattern image of the pillars is written in the electron beam resist layer 900 so as to produce a latent image of the pattern as shown in FIG. 30A. The latent image is developed so that a resist mask 900a is left on the substrate 110 as shown in FIG. 30B. Using the resist mask 900, the substrate 110 is selectively removed by using a dry etching so that the pillars 110a are formed as shown in FIG. 30C. Since the pattern is directly transferred to the substrate 110. The process shown in FIGS. 30A to 30C is simpler than the process shown in FIGS. 29A to 29G.

FIGS. 31A to 31D shows yet another process for producing pillars. First, a die 106 and the substrate 110 are prepared. The die 106 is formed with recesses 106a, the arrangement of which is corresponding to the arrangement of pillars 110a. The recesses 106a may be formed through a process having an electron beam lithography followed by an etching.

Figure 31:
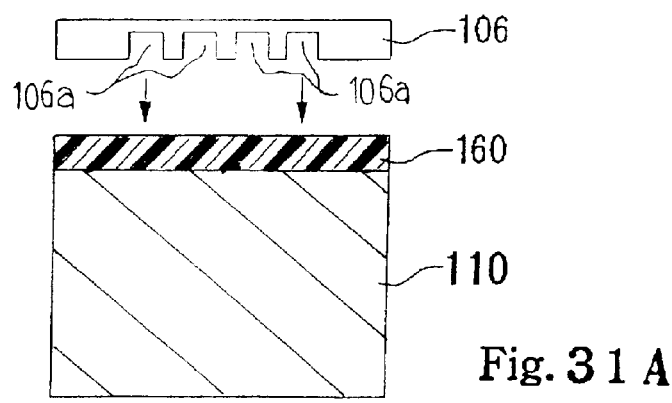
FIGS. 31A to 31D are cross sectional views showing yet another process for forming pillars of a fractionating unit.
Figure 31:
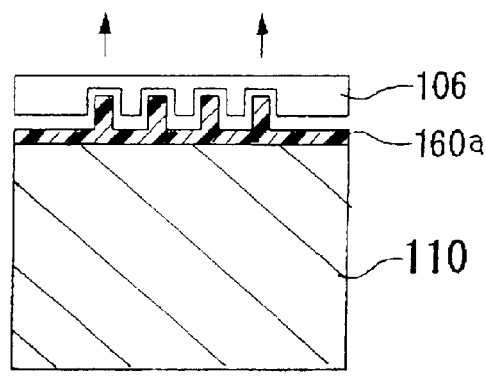
Figure 31:
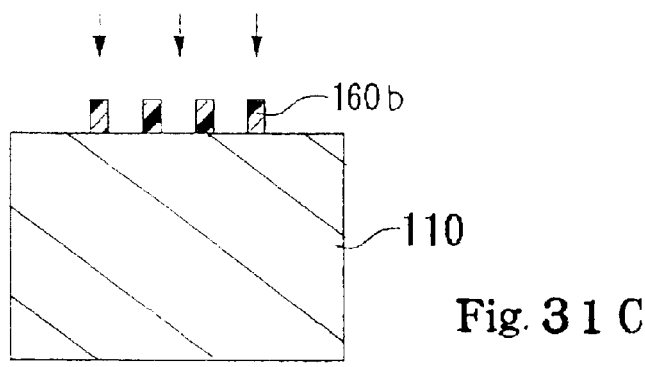
Figure 31:
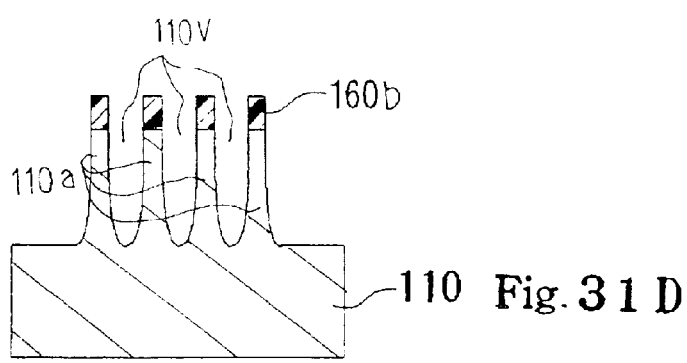

The substrate 110 is coated with synthetic resin. The synthetic resin layer 160 is laminated on the substrate 110. The synthetic resin is in polymethyl methacrylate series. The synthetic resin layer is of the order of 200 nanometers thick. Any material is available for the die 106. In this instance, the material is selected from the group consisting of Si, $SiO_2$ and SiC. The die is opposed to the synthetic resin layer 160 as shown in FIG. 31A.

Subsequently, the die 106 is pressed to the synthetic resin layer 160, and the synthetic resin layer 160 is heated under application of pressure. The pressure ranges from 600 psi to 1900 psi, and the temperature is fallen within the range between 140 degrees to 180 degrees in centigrade. The pattern is transferred to the synthetic resin layer 160. Upon completion of the pattern transfer, the die 106 is separated from the patterned synthetic resin layer 160a as shown in FIG. 31B.

Subsequently, the patterned synthetic resin layer 160a is exposed to oxygen plasma. The patterned synthetic resin layer 160a is uniformly ashed in the oxygen plasma, and the substrate 110 is exposed to the gaps among a resin mask 160b. Using the resin mask 160b, the substrate 110 is selectively removed by using a dry etching as shown in FIG. 31C. The dry etchant is, by way of example, in halogen series. Deep valleys 110V are formed in the substrate, and are as deep as 0.4 micron. The pillars 110a are separated from one another by the valleys 110V, and the gap between the adjacent pillars 110a is of the order of 100 nanometers. Thus, the pillars 110a have large aspect ratio of 4:1. The dry etchant is less active in the deep valleys 110V so that the pillars 110a have the gentle robes merged with one another at the bottoms of the valleys 110V as shown in FIG. 31D. In other words, the pillars have the cross sectional area decreased toward the tops. The resin mask 160b is removed from the top surfaces of the pillars 110a.

Subsequently, the substrate 110 is inserted into a furnace, and is subjected to a furnace anneal at 800 to 900 degrees. Silicon oxide is grown on the entire surface of the silicon substrate 110, and the silicon pillars 110a are covered with a silicon oxide layer 104 (see FIG. 1). The robes are sharply merged with one another at the bottoms of the valleys 110V so that the silicon oxide does not well into any eminence. This means that the valleys are still deep. Thus, the pillars 110a still have the large aspect ratio. The electron beam lithography is not required for the process in which the die 106 is used for the pattern transfer. This results in enhancement of the productivity.

Figure 32:
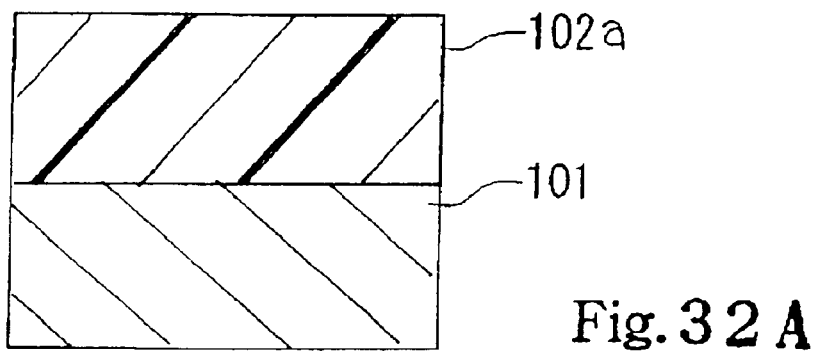
FIGS. 32A to 32C are cross sectional views showing still another process for forming pillars of a fractionating unit.
Figure 32:
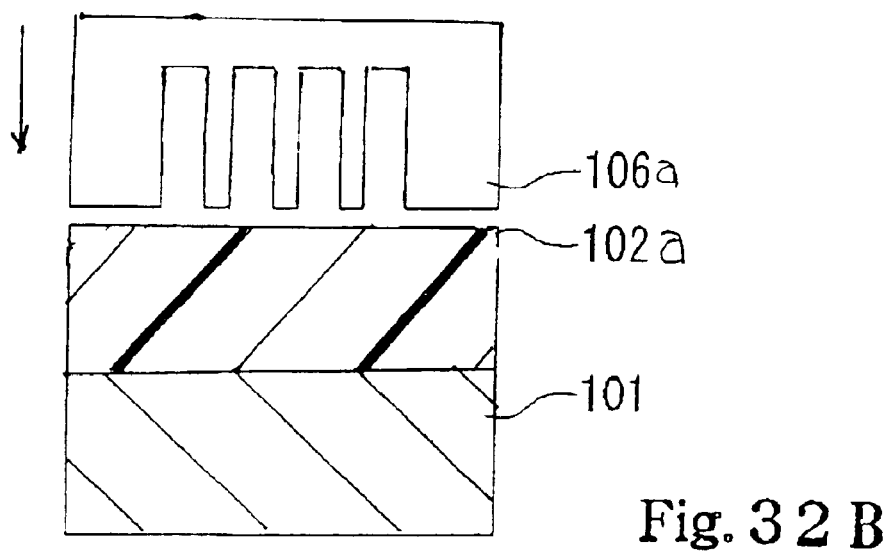
Figure 32:
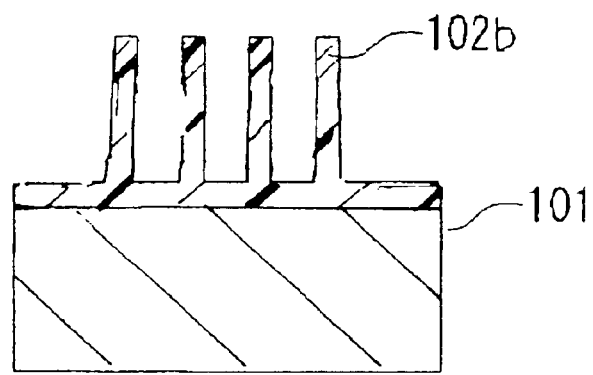

The processes described hereinbefore are applied to substrates made of oxidizable material such as, for example, silicon. The pillars are, by way of example, formed as follows. First, a substrate 101 and a die 106a are prepared. The hie 106a has a pattern of recesses corresponding to the pillars. The groove and liquid sumps have been already formed in the substrate 101. The bottom surface of the substrate 101 is coated with resin. In other words, the bottom surface is overlaid with a resin layer 102a as shown in FIG. 32A. It is preferable that the resin is hydrophilic. The resin may be selected from the group consisting of resins in polyvinyl alcohol series. It is preferable to use ethylene vinyl alcohol resin (EVOH) or polyethylene terephthalate. If the resin is coated with hydrophilic material, hydrophobic resin is available for the process.

Subsequently, the die 102b is pressed to the resin layer 102a as shown in FIG. 32B, and the resin layer is heated. The pattern is transferred from the die 106a to the resin layer 102a as shown in FIG. 32C. Any thermal oxidation is not required, because the resin pillars 102b are hydrophilic. The process is more simpler than the above-described processes, and the productivity is drastically enhanced.

In the substrates fabricated through the above-described processes having the oxidizing steps, the electrophoresis may be used as the sample accelerator. If the groove, liquid sumps and pillars are imperfectly coated with the silicon oxide, the electric current is leaked into the silicon substrate, and the electric field may be too weak to make the sample migrated. In order to prevent the substrate from imperfect coverage with the silicon oxide, the groove and liquid sumps may be formed as follows.

Figure 33A:
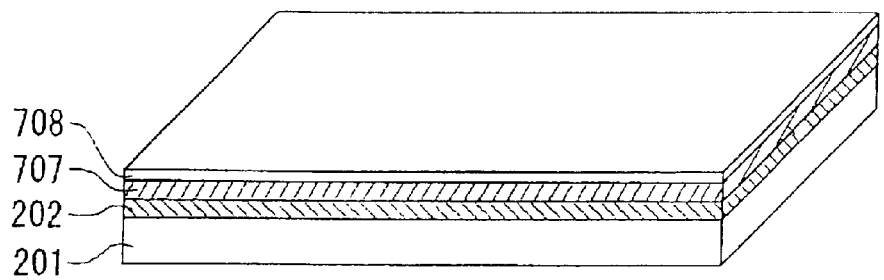
FIGS. 33A to 33D are schematic perspective views showing a process for forming spaces in a substrate.

FIGS. 33A to 33D show a process for forming spaces in a substrate. The process starts with preparation of a silicon substrate 201. The silicon substrate 201 is thermally oxidized so that a silicon oxide layer 202 is grown on the major surface of the silicon substrate 201. Polysilicon is deposited over the major surface of the silicon substrate 201, and the silicon oxide layer 202 is overlaid with a polysilicon layer 707. The polysilicon layer 707 is thermally oxidzed so that a silicon oxide layer 708 is formed on the polysilicon layer 707 as shown in FIG. 33A.

Figure 33B:
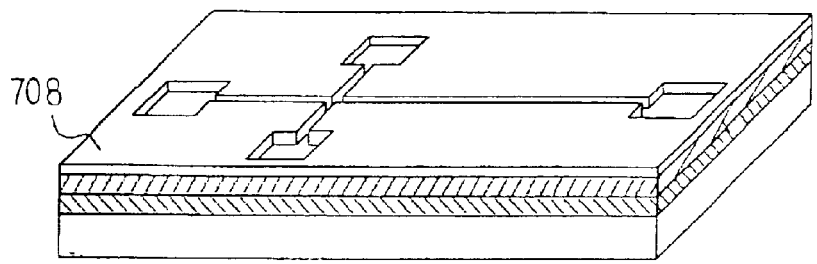

Subsequently, calixarene electron beam negative resist is spread over the entire surface of the silicon oxide layer 708 so that the silicon oxide layer 708 is overlaid with the calyx allene electron beam negative resist layer (not shown). A pattern of a groove and liquid sumps is written in the calixarene electron beam negative resist layer with an electron beam so as to produce a latent image in the negative resist layer. The latent image is developed so that a resist mask (not shown) is left on the silicon oxide layer 708. Using the resist mask, the silicon oxide layer 708 is selectively removed by using a reactive ion etching (RIE), and, thereafter, the resist mask is stripped off. Thus, the pattern is transferred to the silicon oxide layer 708 as shown in FIG. 33B.

Figure 33C:
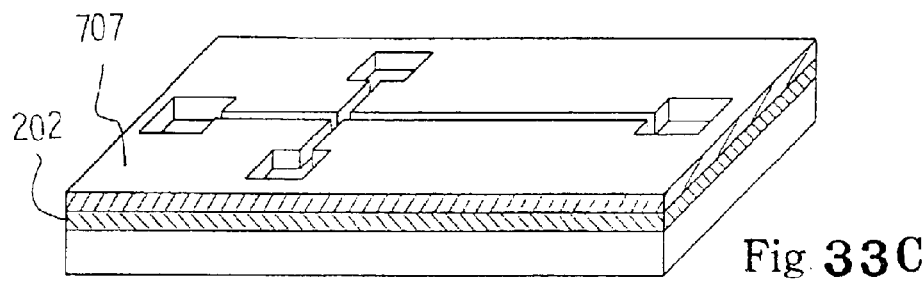
Figure 33D:
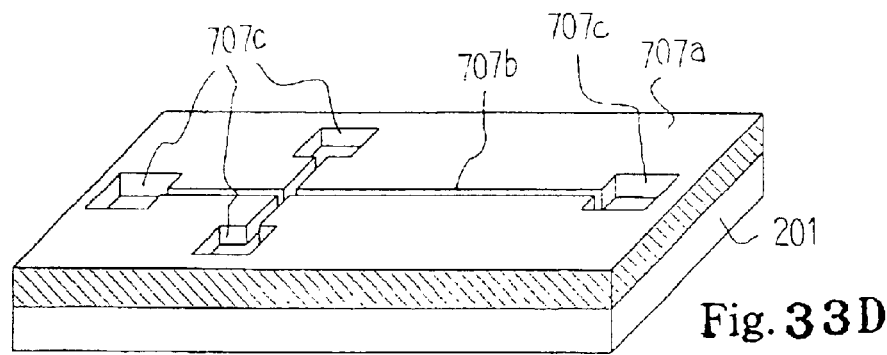

Using the patterned silicon oxide layer 708 as an etching mask, the poly-silicon layer 707 is selectively removed by using an electron cyclotron resonance (ECR) etching so that the pattern is transferred to the polysilicon layer 707. The patterned silicon oxide layer 708 is removed so that the patterned polysilicon layer 707 is exposed as shown in FIG. 33C.

Finally, the patterned polysilicon layer 707 is thermally oxidized. The polysilicon is converted to the silicon oxide, which is merged with the silicon oxide layer 202. In other words, the patterned silicon oxide layer and no-patterned silicon oxide layer 202 are merged into a silicon oxide layer 707a. A groove 707b and liquid sumps 707c are formed in the silicon oxide layer 707a, and the lower part of the silicon oxide layer 707a, i.e., the silicon oxide layer 202 perfectly separates the silicon substrate 201 from the groove 707b and liquid sumps 707c. Even if sample is migrated through the fractionating passage in the groove 707b through the electrophoresis, the current is never leaked from the fluid into the substrate 201.

In the above-described embodiment, the silicon substrate 201 and silicon oxide layer 202 may be replaced with a quartz substrate. The silicon substrate 201, silicon oxide layer 202 and polysilicon layer 707 may be replaced with a SOI (Silicon On Insulator) substrate.

In case where the carbon nanotubes or carbon nanohorns are used in the fractionating region, a core-providing method or an extrusion method may be used. In the extrusion method, the carbon nanotubes or carbon nanohorns are mixed in hydrophilic resin, and the carbon nanotubes or carbon nanohorns are extruded from the resin. The carbon nanotubes and carbon nanohorns are hydrophobic. It is desirable to convert the surfaces of the carbon nanotubes/carbon nanohorns from hydrophobic to hydrophilic before application to the fractionating unit according to the present invention. The carbon nanotubes/carbon nanohorns are converted to hydrophilic through oxidizing treatment as known to persons skilled in the art.

As will be understood, micro-bodies, i.e., the pillars, carbon nanotubes or carbon nanohorns are formed through the processes according to the present invention.

Function of Space among Pillar Forming Regions

Figure 34:
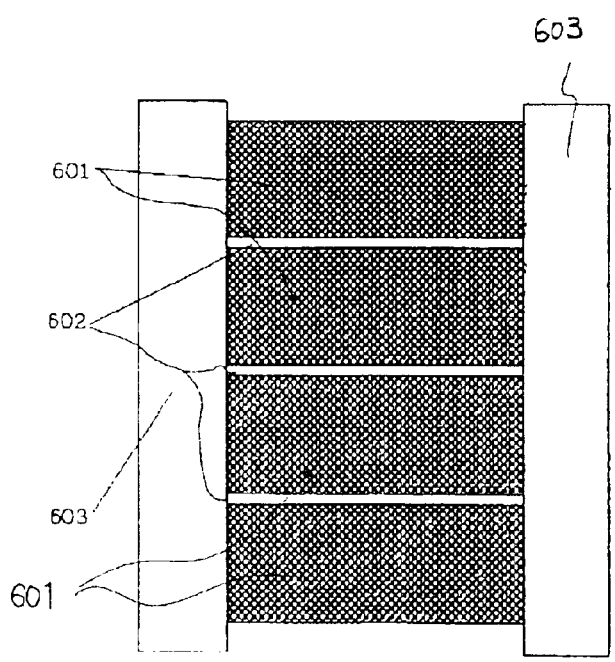
FIG. 34 is a plane view showing the arrangement of fractionating regions incorporated in a fractionating unit according to the present invention.

Turning to FIG. 34 of the drawings, an apparatus embodying the present invention includes a fractionating unit with plural pillar forming regions 601. The pillar forming regions 601 are selectively used as the fractionating region or regions, introducing region and sample holding pillar region (see FIG. 10). The pillar forming regions 601 occupy spaces between walls 603, and paths are defined among the pillar patches for large-sized microstructures. In other words, there is not any gap between the pillar forming regions 601 and the walls 603. The pillar patches are formed in the fractionating regions, and the pillars are formed in the other pillar forming regions at different values of density. The pillar forming regions 601 are spaced from one another in the direction of migration by vacant spaces 602. Any pillar or microbody is not formed in the vacant spaces 602.

The fractionating unit thus arranged achieves a high resolution. FIGS. 35A and 35B show boundaries of fluid. Assuming now that the pillar forming regions 601 are contiguous to one another without any vacant space, the sample is migrated as indicated by an arrow, and forms a boundary 601a like a parabola as shown in FIG. 35A. This is because of the fact that the sample is accelerated on the inner surfaces of the walls 603 by virtue of the capillary action. The capillary action is less influential to the sample migrated in the central region of the passage.

In the case where the vacant spaces 602 are inserted between the adjacent pillar forming regions 601, the sample is made flat at the boundary betwene the pillar forming region 601 and the vacant space, and is temporarily held in the vacant space 602. In detail, the air fills in the vacant spaces 602. While the sample is being migrated in the pillar forming region 601, the sample is warped, and the part of the sample on the walls firstly reaches the boundary between the pillar forming region 601 and the vacant space 602. However, the part of the sample waits for the remaining part, because the air in the vacant space impedes the migration of sample. When the remaining part reaches the boundary between the pillar forming region 601 and the vacant space 602, the sample pushes out the air from the vacant space 602, and enters the vacant space 602. Thus, the vacant spaces 602 make the boundary 601b of the sample flat (see FIG. 35B), and the resolution is improved. The sample is accurately analyzed on the measuring plane.

FIGS. 36A, 36B and 36C show the boundary of buffer solution flowing into a space uniformly filled with artificial gel 601d. A passage is uniformly filled with artificial gel 601d (see FIG. 36A). Buffer solution flows into the passage. Then, the boundary between the buffer solution 601e and the artificial gel 601d is warped due to the different in capillary phenomenon between the central area and the peripheral area as shown in FIG. 36B. While the buffer solution 601e is proceeding toward a detector 601f, the boundary is gradually warped widely as shown in FIG. 36C.

Figure 37A:
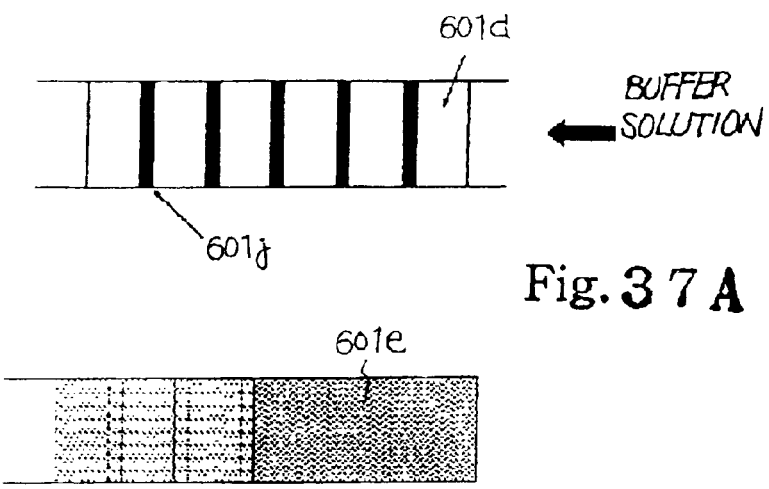
FIGS. 37A to 37C are schematic views showing buffer solution flowing into a space non-uniformly filled with artificial gel.
Figure 37B:
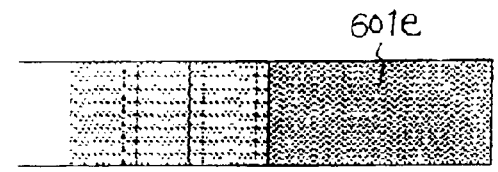
Figure 37C:
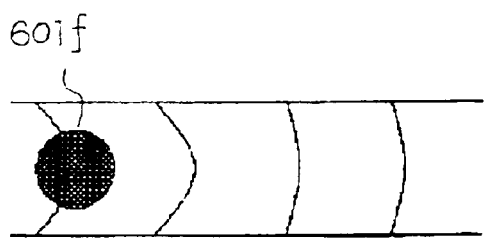

FIGS. 37A shows a fluid passage in which pillars are sparsely arranged in regions 601j. The sparsely arranged pillar regions 601j serves as similar to the vacant spaces 602. Buffer solution flows into the fluid passage. Although the boundary of the buffer solution is warped in the artificial gel 601d, the time lug is canceled in the sparsely arranged pillar region 601j, and the boundary is reshaped into flat in the sparsely arranged pillar regions 601j as shown in FIG. 37B. As a result, when the sample reaches the detector 601f, the boundary of the sample is less warped as shown in FIG. 37C.

As will be understood, the vacant space and sparsely arranged pillar region are effective against the warped boundary of the sample. Although the vacant space is formed in the fractionating unit accompanied with the capillary sample accelerator (see FIGS. 8 and 10). The vacant spaces may be formed in the fractionating unit accompanied with the electrophoresis sample accelerator, because the band-shaped sample is warped. Even though the vacant spaces are filled with buffer solution, the band-shaped sample is reshaped in the vacant spaces.

In the above-described embodiments, the pillars 110/125 and walls 125A are corresponding to obstacles.

Investigations

The present inventors fabricated samples of the fractionating units according to the present invention, and evaluated the samples as follows.

Fabrication Process

Figure 38A:
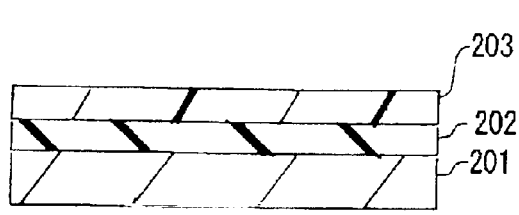
FIGS. 38A to 38Q are cross sectional view showing a process through which the present inventors fabricated a sample of an apparatus for evaluation.
Figure 39A:
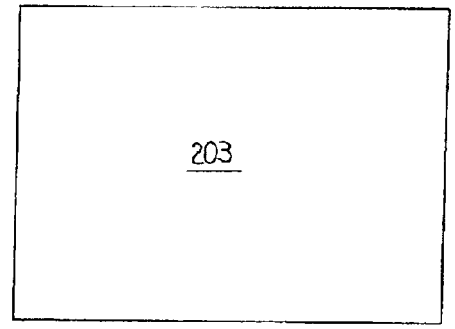
FIGS. 39A to 39Q are plane views showing the process used for the fabrication of the sample.

The inventors firstly prepared a silicon substrate 201. Silicon oxide was grown on the major surface of the silicon substrate 201, and formed a silicon oxide layer 202. Calixarene electron beam negative resist was spread over the silicon oxide layer 202, and formed a negative resist layer 203. The silicon oxide layer 202 was 35 nanometers thick, and the calixarene electron beam negative resist was 55 nanometers thick. A predetermined area of the negative resist layer 203 was exposed to an electron beam so that a latent image of a pillar pattern was produced in the negative resist layer 203. The resultant structure was shown in FIGS. 38A and 39A.

Figure 38B:
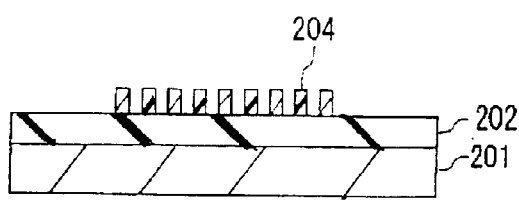
Figure 39B:
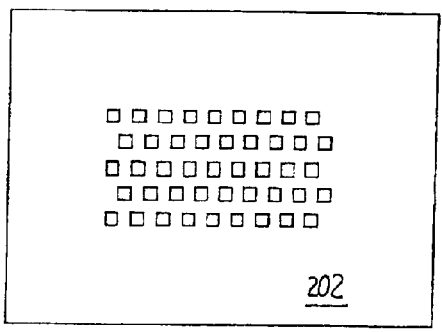

The latent image was developed. Xylene-contained developer was used. After the development, the resultant structure was rinsed in isopropyl alcohol. Then, a resist pattern 204 was left on the silicon oxide layer 202 as shown in FIGS. 38B and 39B.

Figure 38C:
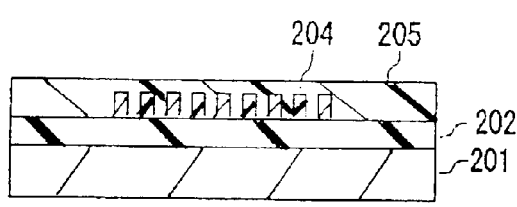
Figure 39C:
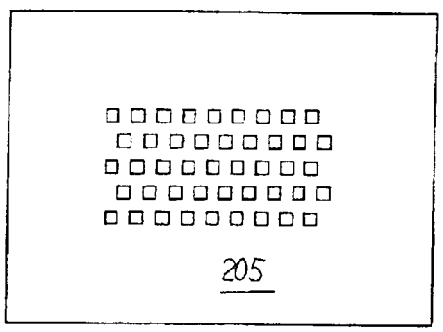
Figure 38D:
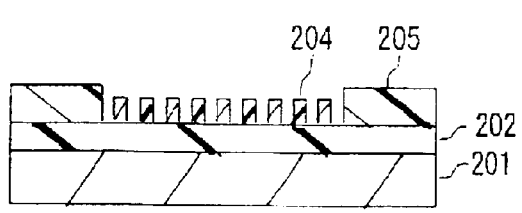
Figure 39D:
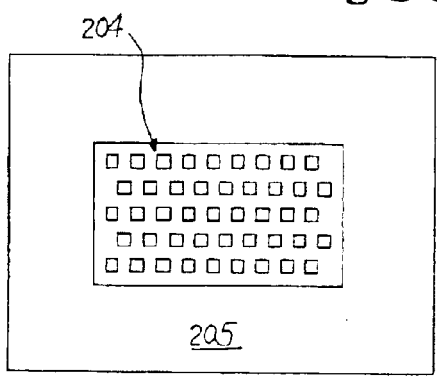
Figure 39:
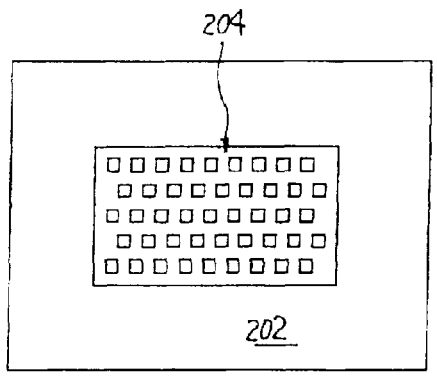
Figure 39:
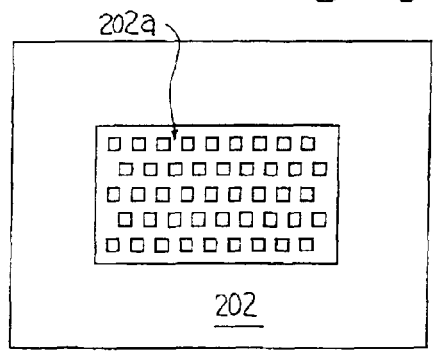
Figure 39:
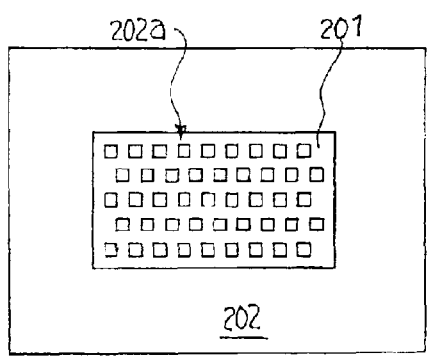
Figure 39:
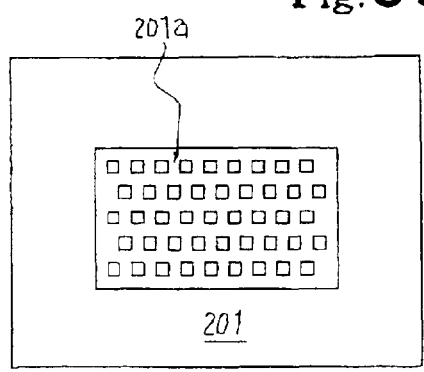
Figure 39:
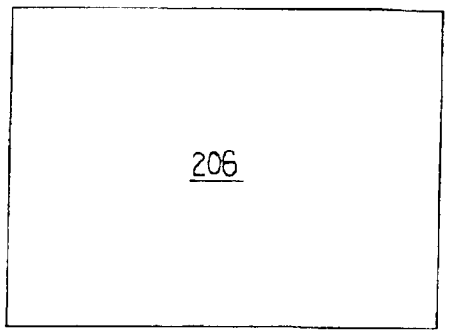
Figure 39:
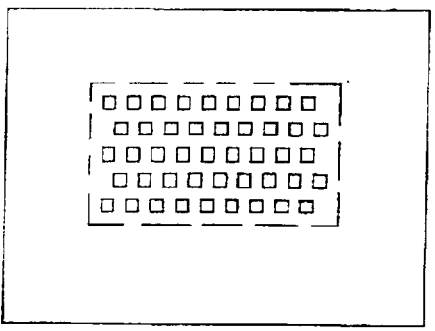
Figure 39:
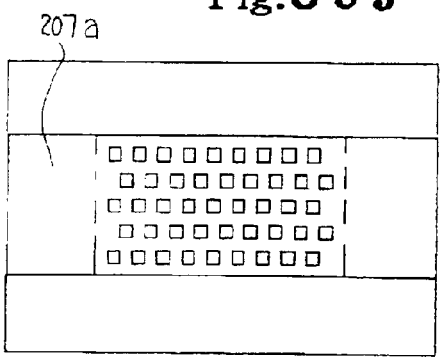
Figure 39:
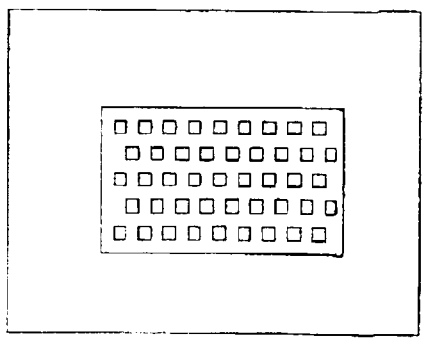

Subsequently, positive photo-resist 205 was spread over the entire surface of the resultant structure, and the resist pattern 204 was covered with a positive photo-resist layer 205 as shown in FIGS. 38C and 39C. The positive photo-resist layer 205 was of the order of 1.8 microns thick. A pattern image of an array region was transferred from a photo-mask (not shown) to the positive photo-resist layer 205, and a latent image was produced in the positive photo-resist layer 205. The latent image was developed. Then, the positive photo-resist layer 205 was partially removed from the area over the array region, and the resist pattern 204 was exposed, again, as shown in FIGS. 38D and 39D.

Using the patterned resist layers 204 and 205, the silicon oxide layer 202 was selectively removed by using a reactive ion etching. The etchant contains $CF_4$ gas and $CHF_3$ gas. The dry etching was continued over the thickness of the silicon oxide layer 202, i.e., 35 nanometers. Then, the silicon substrate 201 was exposed, again, as shown in FIGS. 38E and 39E. The resist pattern 204 was removed by using organic remover containing acetone, alcohol and water, and the resultant structure was subjected to a plasma oxidization, Pillars of silicon oxide 202a were exposed as shown in FIGS. 38F and 39F.

Using the pillars of silicon oxide 202 as an etching mask, the silicon substrate 201 was selectively removed in HBr gas-contained etchant through the electron cyclone resonance (ECR) etching, and the pattern of silicon oxide pillars 202a was transferred to the silicon substrate 201. Upon completion of the dry etching, the silicon substrate 201 had the minimum thickness of the order of 400 nanometers. The silicon oxide 202 was removed through a wet etching. The wet etchant was buffered hydrofluoric acid (BHF). Pillars 201a were formed in the array region as shown in FIGS. 38H and 39H.

Subsequently, silicon oxide was deposited over the entire surface of the resultant structure by using a chemical vapor deposition. The silicon oxide filled the valleys among the silicon pillars 201a, and swelled into a silicon oxide layer 206 as shown in FIGS. 38I and 39I. The silicon oxide layer 206 was of the order of 100 nanometers thick.

Positive photo-resist was spread over the entire surface of the silicon oxide layer 206. The silicon oxide layer 206 was overlaid with a positive photo-resist layer 207 as shown in FIGS. 38J and 39J, and was 1.8 microns thick. A pattern image of a groove was transferred to the positive photo-resist layer 207, and a latent image was produced in the positive-resist layer 207. The latent image was developed so that a photo-resist mask 207a was left on the silicon oxide layer 206 as shown in FIGS. 38K and 39K. Using the photo-resist mask 207a, the silicon oxide layer 206 was selectively removed by using the wet etching. Buffered hydrofluoric acid was used as the wet etchant. The silicon substrate 201 was exposed as shown in FIGS. 38L and 39L.

Figure 38:
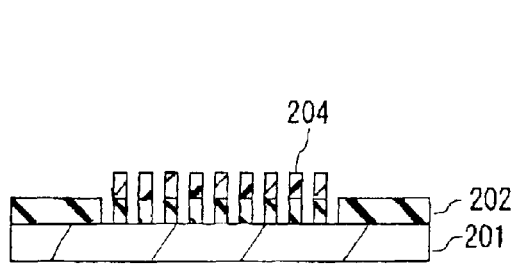
Figure 38:
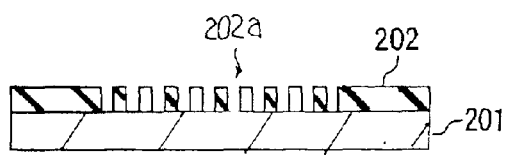
Figure 38:
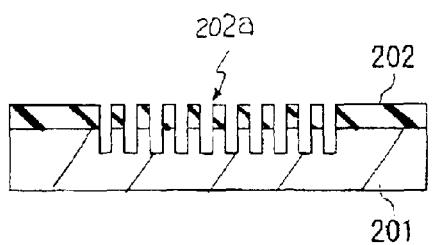
Figure 38:
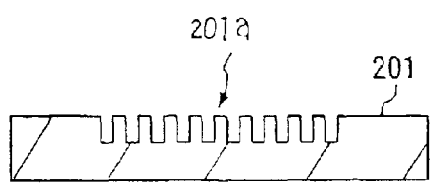
Figure 38:
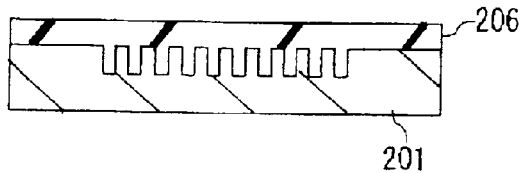
Figure 38:
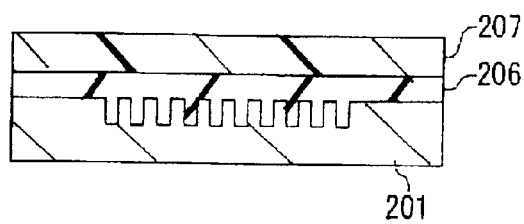
Figure 38:
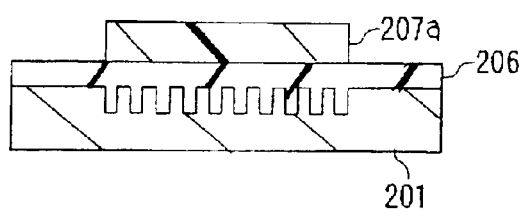
Figure 38:
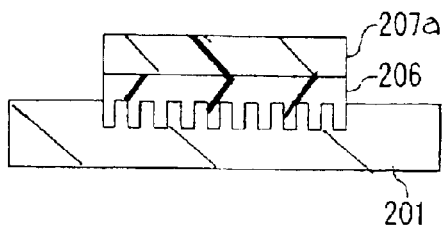
Figure 38M:
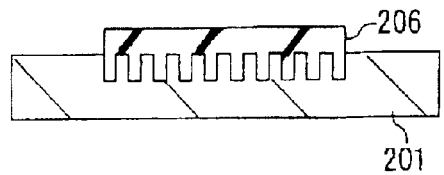
Figure 39M:
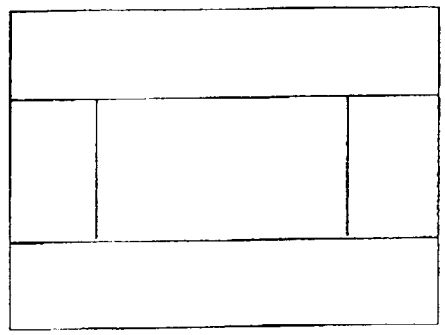
Figure 38N:
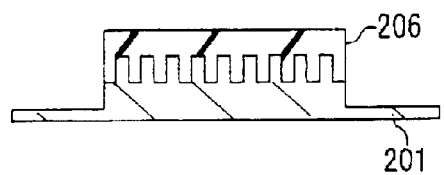
Figure 39N:
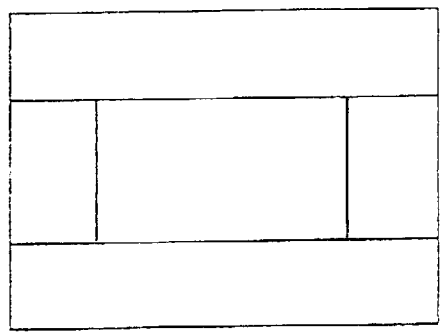
Figure 38O:
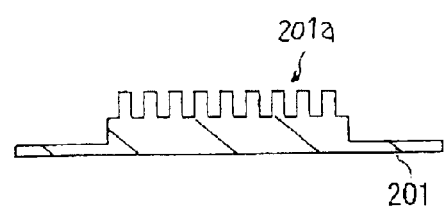
Figure 39O:
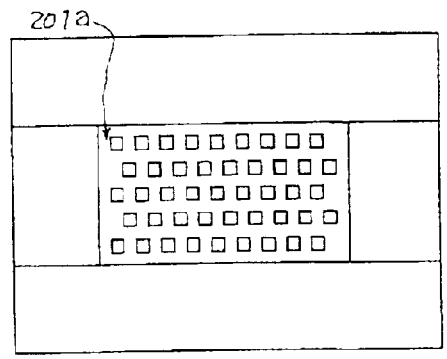

The photo-resist mask 207a was removed by using organic remover as shown in FIGS. 38M and 39M. The silicon oxide layer 206 was left on the array region. Using the silicon oxide layer 206 as an etching mask, the silicon substrate 201 was selectively removed by using a wet etching. Tetramethylammoniumhydroxide was used as the wet etchant. The resultant structure was shown in FIGS. 38N and 39N. The silicon oxide was removed by using the buffered hydrofluoric acid, and the silicon pillars 201 were exposed, again, as shown in FIGS. 38O and 39O.

Figure 38P:
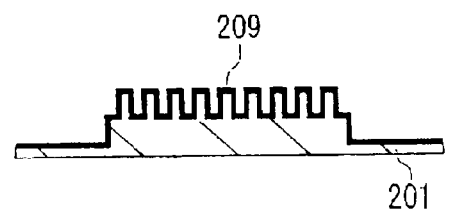
Figure 39P:
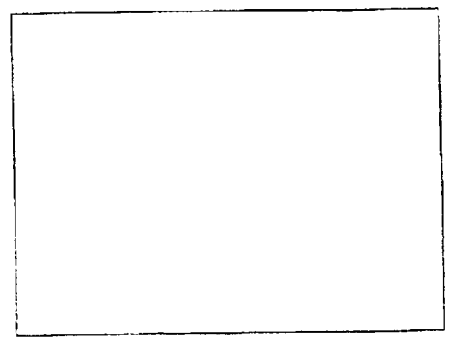
Figure 38Q:
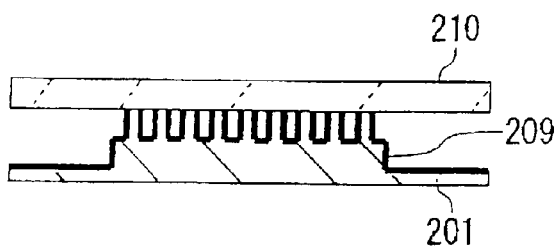
Figure 39Q:
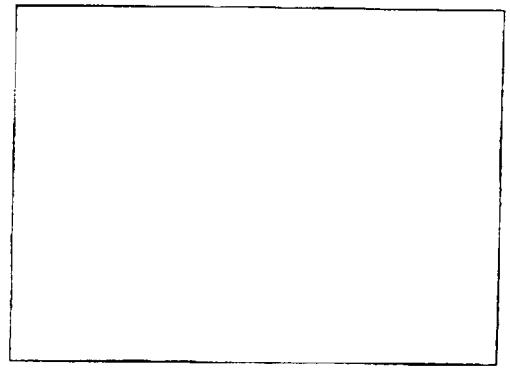

The silicon substrate 201 was placed in a furnace, and silicon oxide was thermally grown in the furnace as shown in FIGS. 38P and 39P. The silicon substrate 201 was covered with a silicon oxide layer 209 of 20 nanometers thick as shown in FIGS. 38P and 39P. As described herienbefore in detail, the silicon oxide was hydrophilic so that buffer solution was to be smoothly introduced. Finally, a glass plate was fixed to the resultant structure through an electrostatic process as shown in FIGS. 38Q and 39Q.

Figure 41:
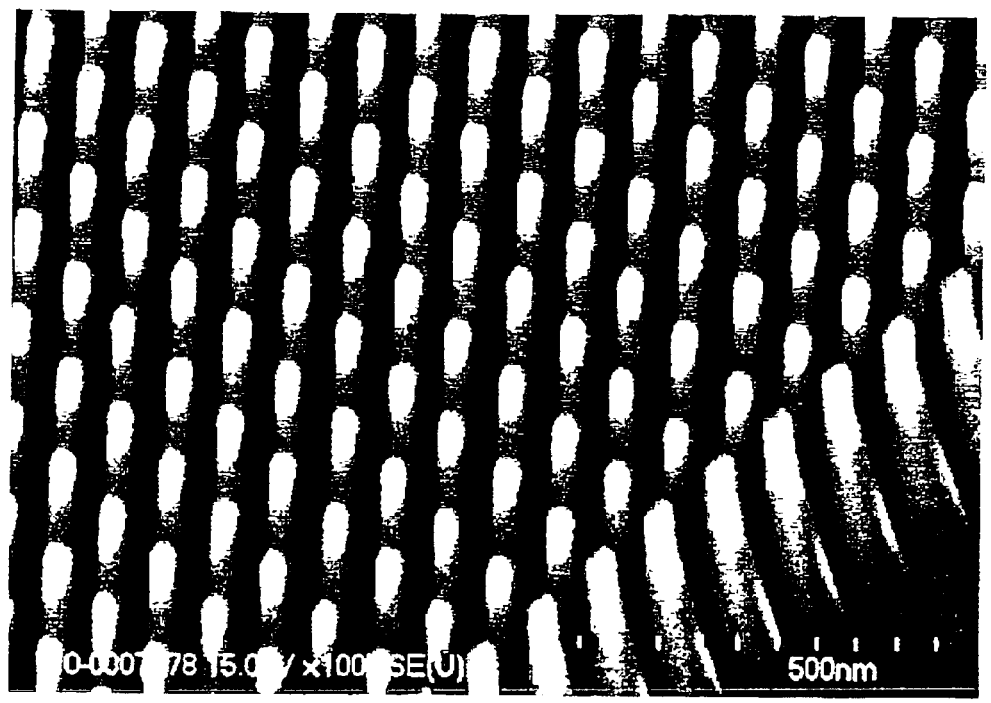
FIGS. 40 and 41 are photographs showing pillars fabricated through a process according to the present invention.
Figure 40:
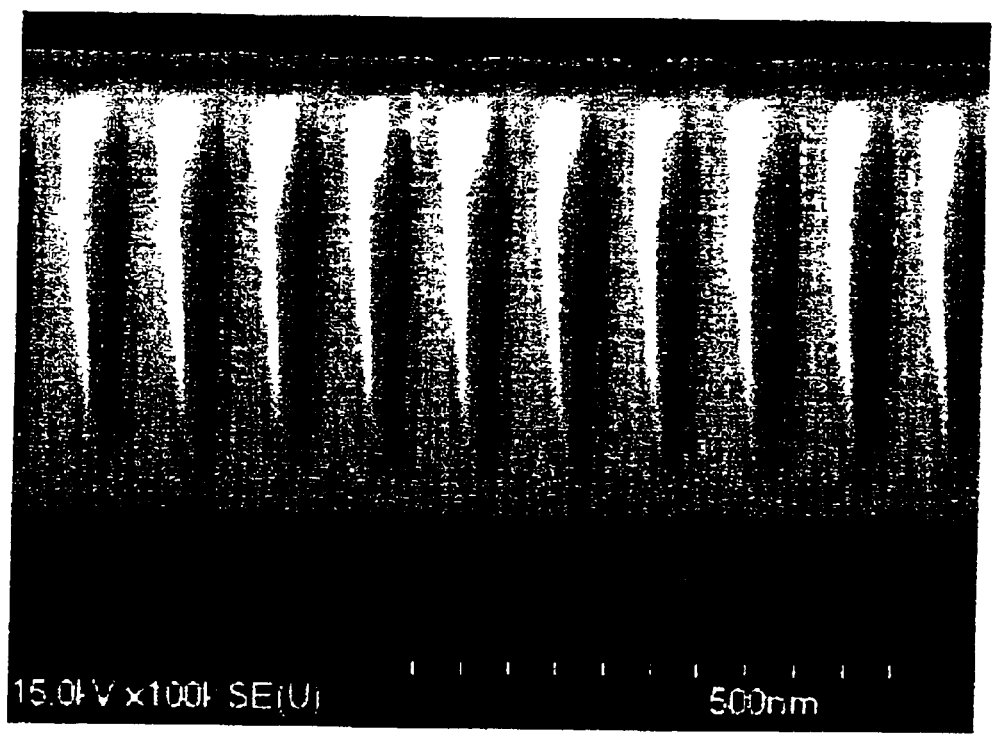

The inventors inspected the sample of the fractionating unit, and confirmed that the sample was excellent. The inventors observed the intermediate structure of a sample at the step shown in FIG. 38P through an electron microscope, and took photographs. FIGS. 40 and 41 are the photographs. Although the silicon oxide was grown to 30 nanometers thick, it was understood that the pillars were regularly arranged. The mean gap among the pillars was of the order of 60 nanometers. Thus, the inventors successfully evaluated the process sequence.

Thermal Oxidation

The inventors investigated the thermal oxidation on the pillars as follows. Samples, which had two sorts of pillars different in aspect ratio, were fabricated through the process similar to the first example. The pillars were thermally oxidized for investigating the thermal oxidation. The inventors took photographs of the two sorts of pillars.

Figure 42:
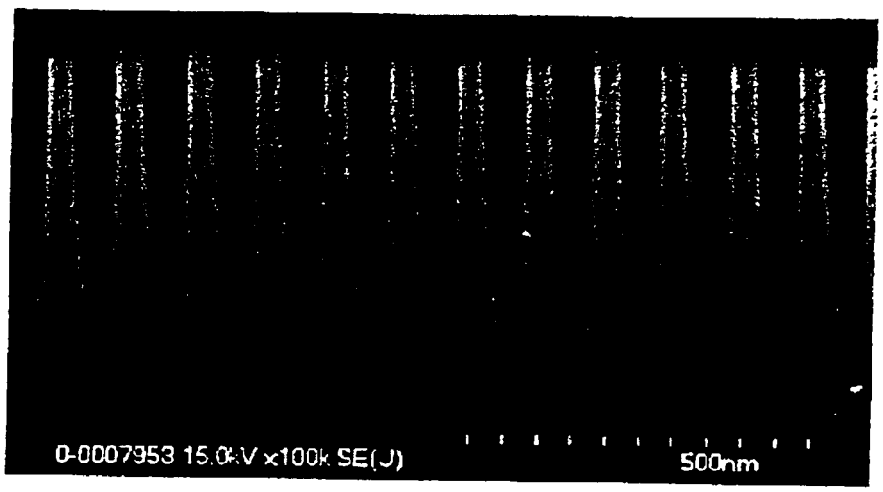
FIG. 42 is a photograph showing pillars of Sample 1 taken upon completion of an etching.
Figure 43:
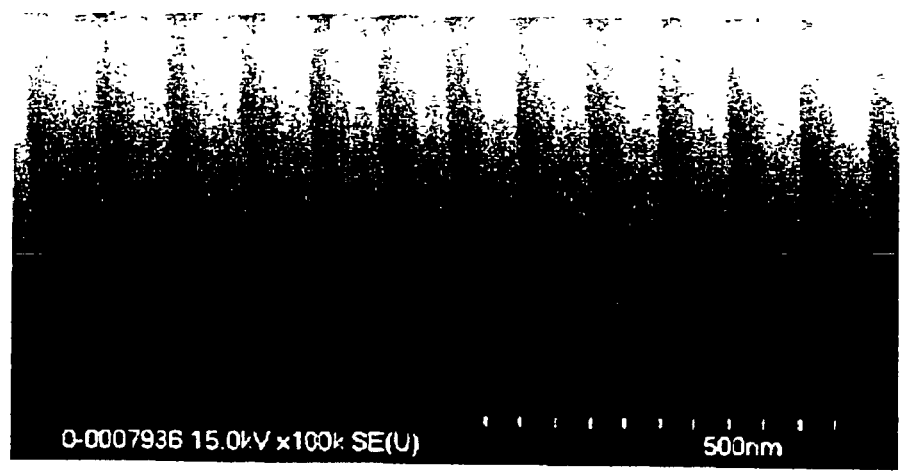
Figure 4:
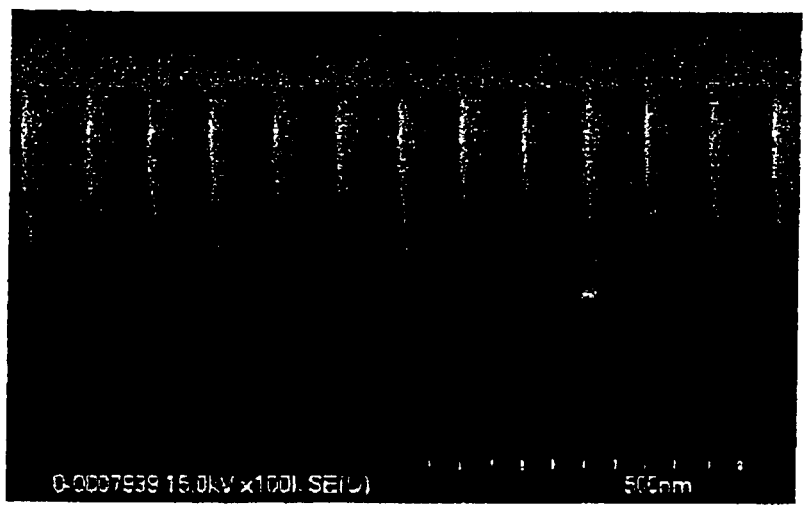
Figure 4:
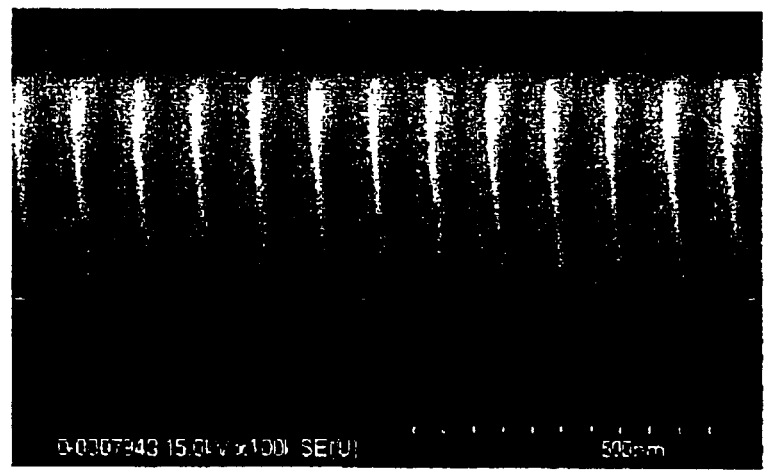
Figure 4:
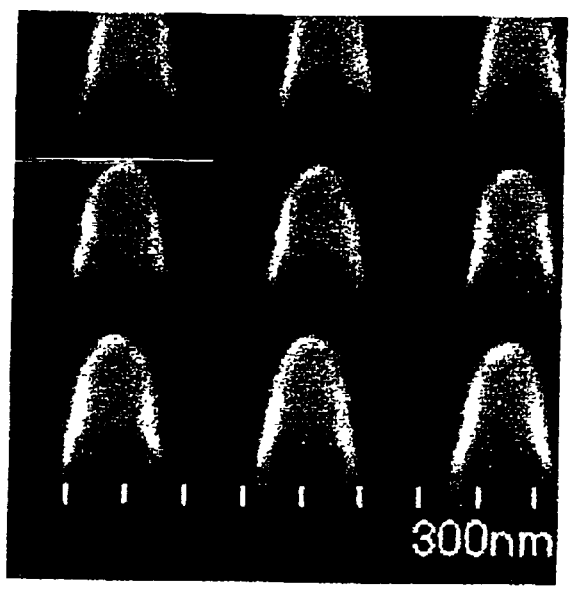
Figure 4:
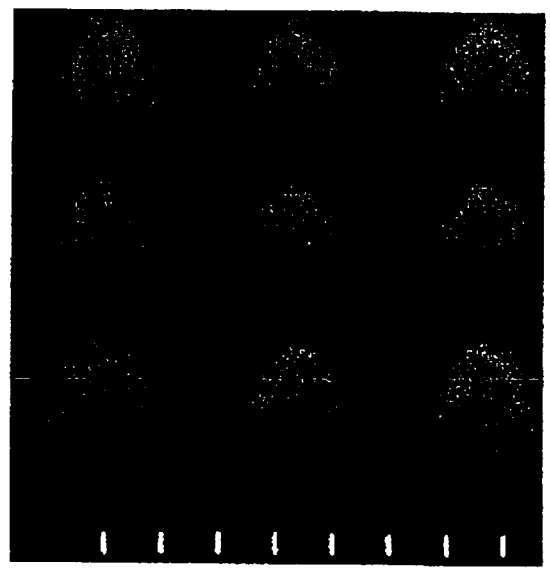

Sample 1 had pillars of 440 nanometers high, and the pillars were spaced by 80 nanometers. The pillars were decreased in cross section toward the top surfaces. The pillars were so close that the robes were merged with one another at the bottoms of the valleys. FIG. 42 was the photograph of Sample 1 after the etching. FIGS. 43 to 45 were photogrpahs after the thermal oxidatoin. The silicon oxide layers were grown to 10 nanometers thick, 20 nanometers thick and 30 nanometers thick, respectively, and were seen in the photographs of FIGS. 43, 44 and 45. The thickness was measured on the side surfaces of the pillars.

Figure 48:
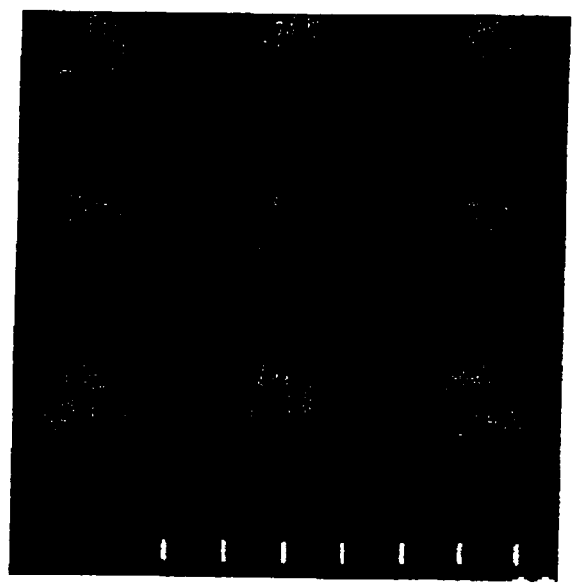
Figure 49:
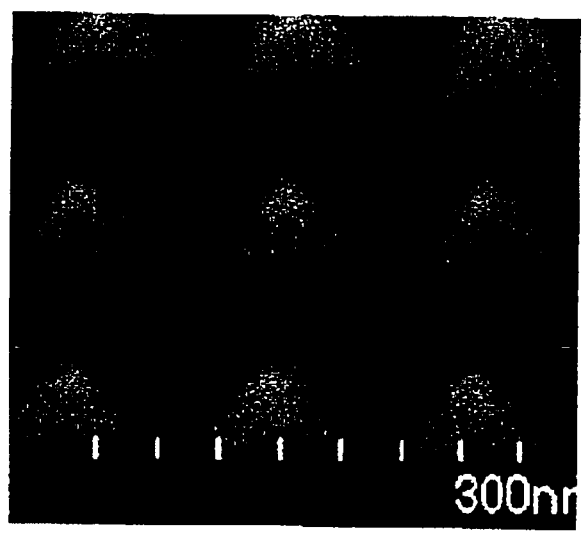

Sample 2 had pillars of 200 nanometers high, and the pillars were spaced by 100 nanometers. The pillars were also decreased in cross section toward the top surfaces, and had the robes. Nevertheless, the pillars were widely spaced so that the bottoms of valleys were flat. FIG. 46 was the photograph of Sample 2 after the etching. The flat bottom surfaces were seen in the photograph. Sample 2 was subjected to the thermal oxidation, and silicon oxide was grown to 10 nanometers thick, 20 nanometers thick and 30 nanometers thick, respectively. The silicon oxide layer of 10 nanometers thick, silicon oxide layer of 20 nanometers thick and silicon oxide layer of 30 nanometers thick were seen in the photographs of FIGS. 47, 48 and 49, respectively. The thickness was measured on the side surfaces of the pillars.

Comparing the photographs of Sample 1 with the photographs of Sample 2, it was understood that the pillars densely formed on the substrate were effective against the reduction of the aspect ratio. In detail, although the silicon oxide was increased in thickness to 30 nanometers, the silicon oxide did not swell into an eminence in Sample 1. This means that the pillars kept the large aspect ratio. On the other hand, the thermal oxidation stopped on the side surfaces of the pillars at 20 nanometers thick in Sample 2. However, the thermal oxidation was continued at the bottoms of the valleys. The silicon oxide swelled into eminences in Sample 2, and the depth of valleys was decreased (compare FIG. 46 with FIG. 49).

The inventors confirmed that the flared configuration, the cross section of which was decreased toward the top, and the bases of pillars merged with one another were effective against reduction in aspect ratio.

Capillary Action

Figure 50A:
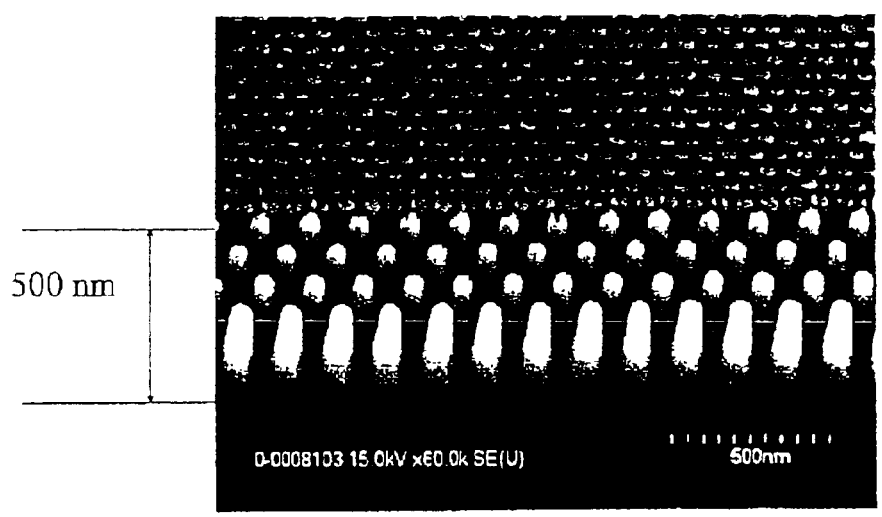
FIG. 50A is a photograph showing a triangular lattice of pillars.

The inventors fabricated a sample where the pillars were arranged partially at high density and partially in at low density. The high dense regions were altered with the sparse regions along a fluid passage. The pillars were formed by using the electron beam lithography and dry etching, and the region measured 40 microns by 60 microns. The pillars in the high dense regions were arranged in triangular lattice at pitches of 100 nanometers (see FIG. 50A), and each of the sparse regions was 50 nanometers wide between two high dense regions.

Figure 50B:
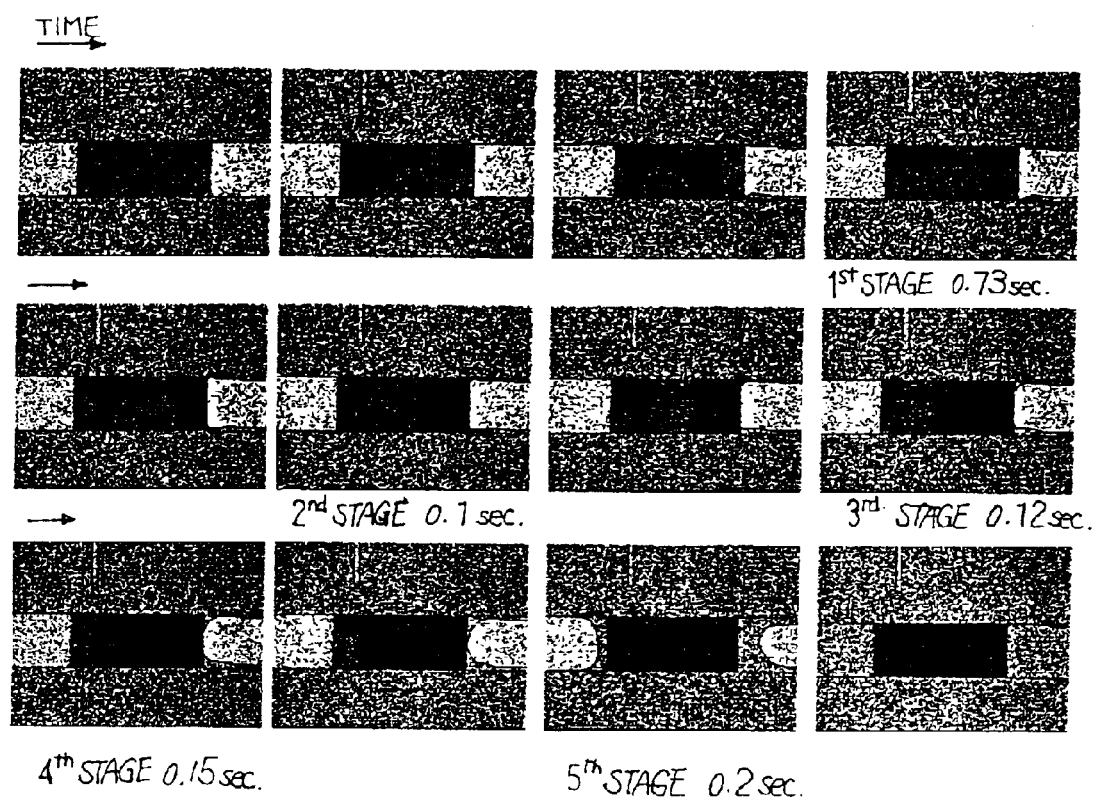
FIG. 50B is a series of photographs showing migration of buffer solution through pillar regions different in density.

The inventors introduced sample into the fluid passage, and observed the migration of sample. FIG. 50B are photographs showing the migration of sample. The deep black area represented the sample. The sample started the migration at the leftmost photograph in the uppermost row. The sample proceeded through the fluid passage, and was seen in the photographs on the right side. When the sample passed the first high dense region, 0.73 second was consumed, and the rightmost photograph showed the sample upon completion of the migration through the first high dense region.

The sample continued the migration from the leftmost photograph toward the rightmost photograph in the second row. 0.1 second was consumed until the sample completed the migration through the second high dense region, and 0.12 second was consumed until the sample completed the migration through the third high dense region.

The sample further continued the migration from the leftmost photograph toward the rightmost photograph in the third row. 0.15 second was consumed until the sample completed the migration through the fourth high dense region. When the sample completed the migration through the fifth high dense region, 0.2 second was consumed.

The time lug was canceled at the boundary between the high dense region and the sparse region, and the sample formed a flat front surface. Thus, the sparse regions caused the sample to reshape the front surface at the boundary so that the detectable portion of the sample was widened.

The inventors confirmed that the migration speed was controllable by changing the pillar regions in diameter of pillars or pillar density. When the dispersion of pillar density was optimized, the uniformity of sample loading was enhanced.

Fabrication Process

Figure 51:
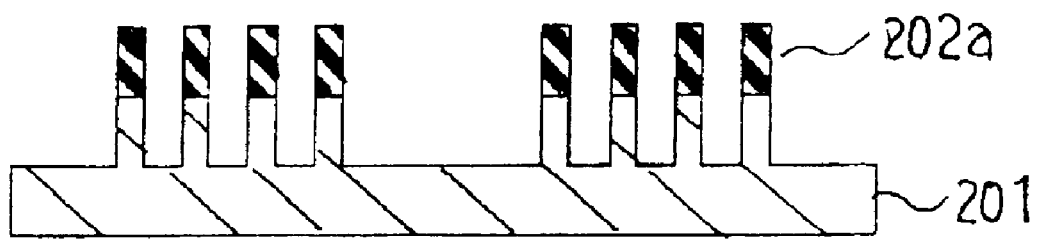
FIGS. 51A to 51E are cross sectional view showing a process sequence through which inventors fabricated a sample.
Figure 51:
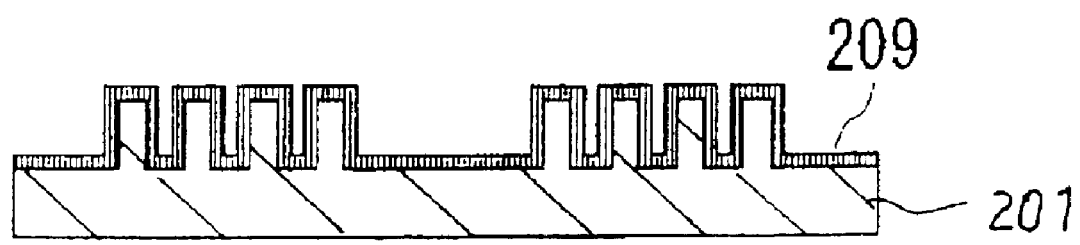

The inventors fabricated samples of a fractionating unit through the following process. FIGS. 51A to 51E shows the process sequence. First, the inventors prepared a silicon substrate 201, and grew silicon oxide on the major surface of the silicon substrate 201. The silicon oxide formed a silicon oxide layer 202 of 35 nanometers thick as shown in FIG. 51A.

Calixarene electron beam negative resist was spread over the silicon oxide layer 202, and was formed into a negative resist layer of 55 nanometers thick. An image of fractionating region was written in the negative resist layer with an electron beam so that a latent image was produced therein. The latent image was developed in a developer containing xylene, and, thereafter, the resultant structure was rinsed in isopropyl alcohol. A resist mask 204 was left on the silicon oxide layer as shown in FIG. 51B.

Using the resist mask 204, the silicon oxide layer 202 was selectively removed by using a reactive ion etching (RIE). The dry etchant contained $CF_4$ and $CHF_3$. The silicon oxide layer 202 was patterned so that a siliconoxide mask 202a was left on the silicon substrate 202 as shown in FIG. 51C.

The resist mask was removed by using organic remover containing acetone, alcohol and water, and the resultant structure was subjected to an oxidation plasma treatment. The silicon substrate 201 was selectively removed by using an electron cyclone resonance (ECR) etching as shown in FIG. 51D. The etchant contained HBr gas and oxygen gas.

The silicon oxide mask 202a was removed by using buffered hydrofluoric acid (BHF), and the resultant silicon substrate 201 was placed in a furnace. The surface portion of the silicon substrate 201 was thermally oxidized so that the silicon substrate 201 was covered with a silicon oxide layer 209 as shown in FIG. 51E. Thus, the sample was obtained.

Figure 52:
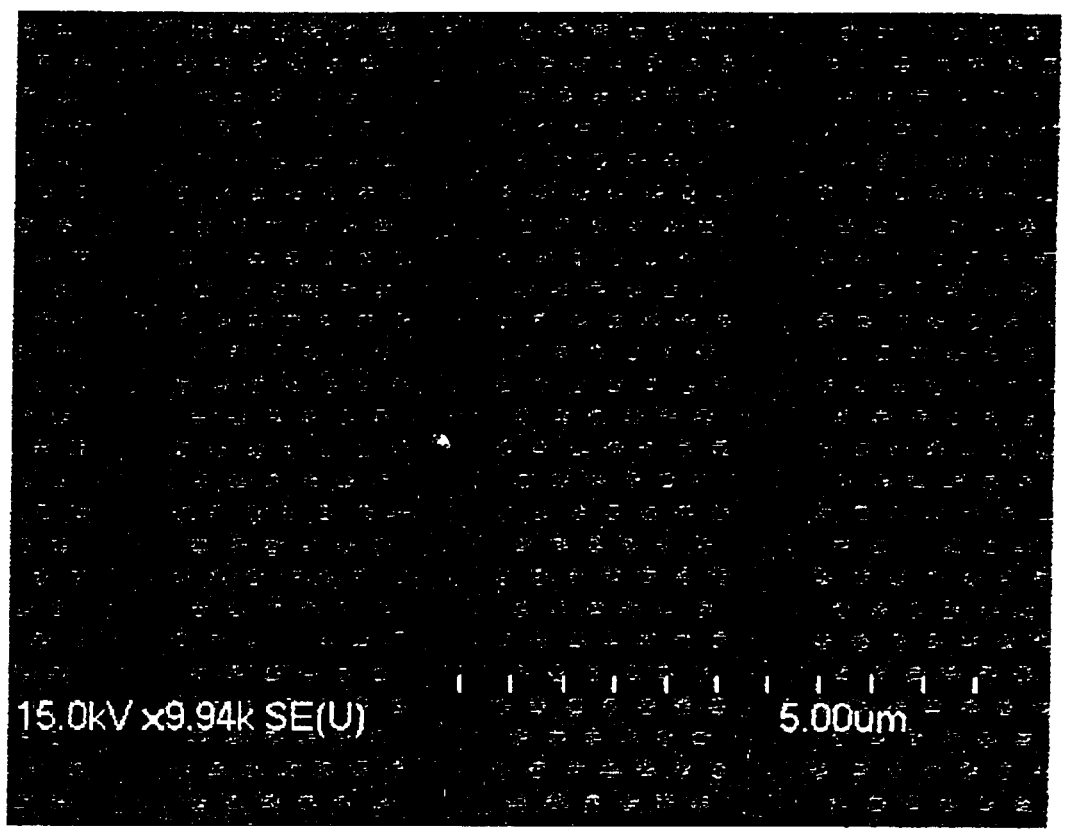
FIG. 52 is a photograph showing a sample fabricated by the inventors.
Figure 53:
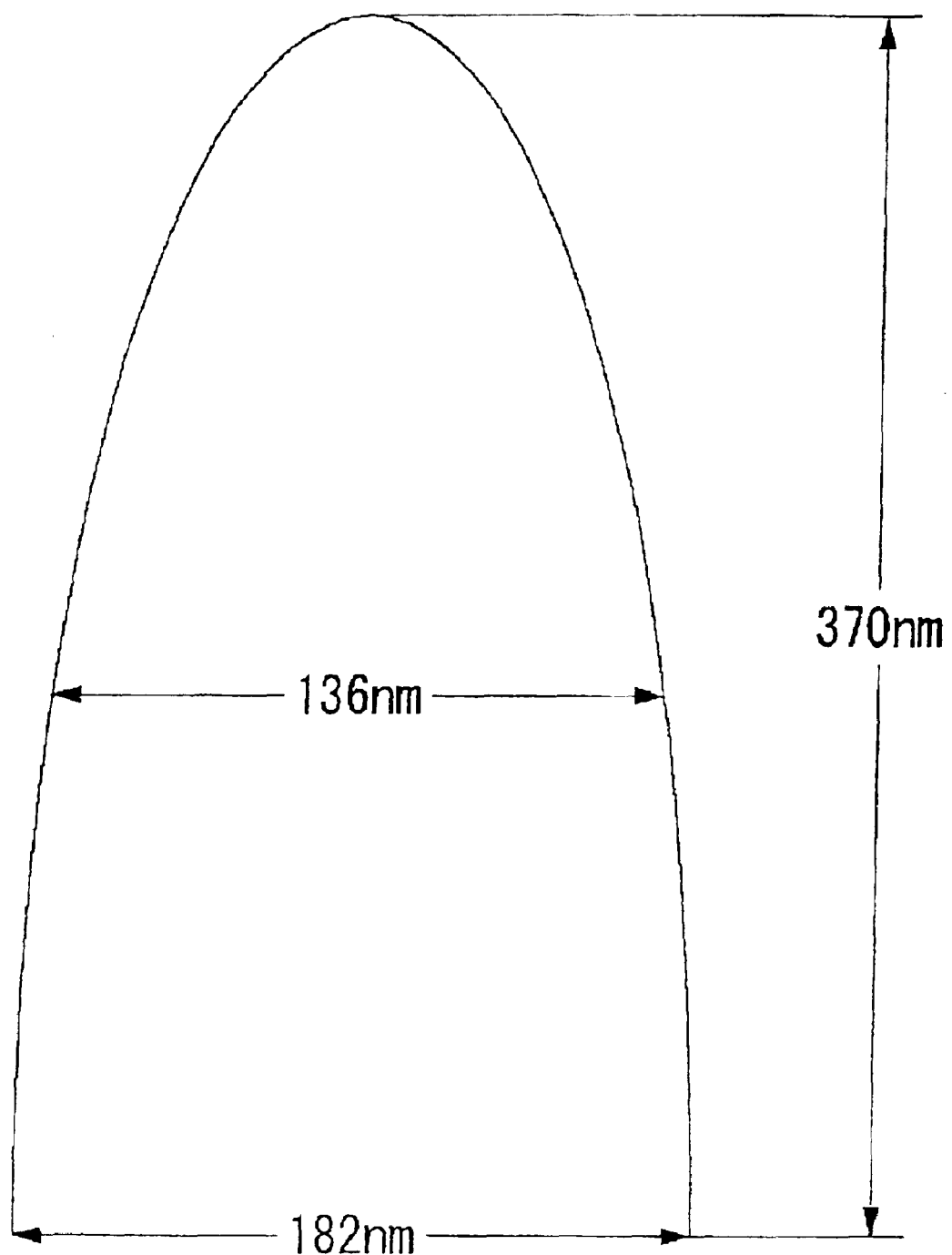
FIG. 53 is a schematic view showing the measurements of a pillar incorporated in the sample.

The inventors observed the sample through an electron microscope, and took a photograph. FIG. 52 shows the photograph. A large number of pillars were seen in the photograph. The pillars had a flared configuration. The pillars measured 370 were 370 nanometers high (see FIG. 53). The diameter of the pillars was 136 nanometers at the intermediate section and 182 nanometers at the base section. The pillars were arranged at pitches of 350 nanometers. The patch region was 2500 nanometers wide, and the gap between the patch regions was 1000 nanometers. The fractionating passage was 40 millimeters long and 80 microns wide. The fractionating passage was 370 nanometers deep.

Steps after Completion of Fractionating Passage

Figures 54A, 55A:
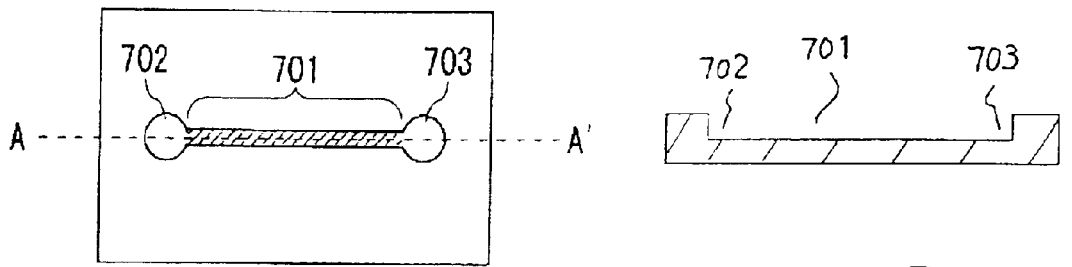
FIGS. 54A to 54C are plane views showing later part of the process for fabricating the sample of a fractionating unit.
FIGS. 55A to 55C are cross sectional views taken along line A–A' and showing the sample in the later part of the process.

The inventors continued the fabrication process for the sample. FIGS. 54A to 54C and 55A to 55C show the steps of the later part of the fabrication process. The fractionating passage was hatched, and was labeled with reference numeral 701. The fractionating passage 701 extended between liquid sumps 702 and 703 as shown in FIG. 54A and 55A.

Figures 54B, 55B:
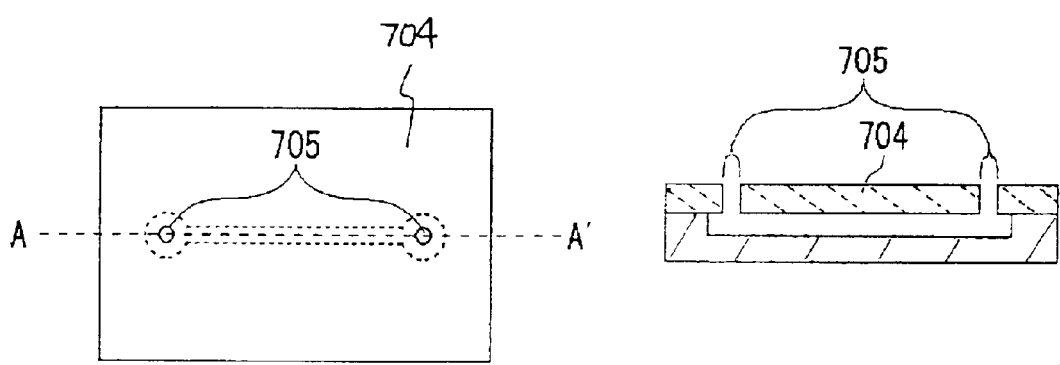
Figures 54C, 55C:
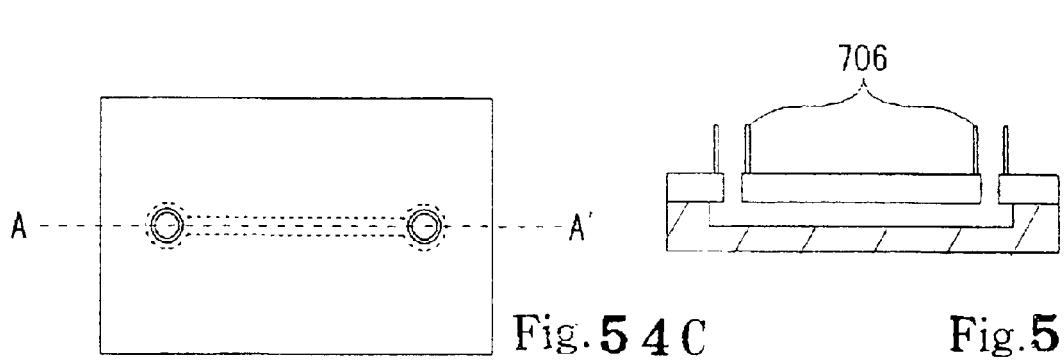

A cover plate 704 was prepared. The cover plate 704 was made of glass, and was formed with holes 705. The cover plate 704 was laminated on the substrate, and the holes 705 were aligned with the liquid sumps 702/703, respectively. The cover plate 704 was fixed to the substrate through an electrostatic process as shown in FIGS. 54B and 55B.

Finally, the glass tubes 706 were prepared. The glass tubes were 3 millimeters in inner diameter, 5 millimeters in outer diameter and 5 millimeters in length. The glass tubes 706 were aligned with the holes 705, and were bonded to the cover plate 704 with epoxy resin. An electrophoresis sample accelerator was assembled with the fractionating unit.

Fractionation Characteristics

The inventors evaluated the sample of the apparatus. The inventors fed 1×TBE buffer, which was 0.09M trisbolate+2 mM EDTA, through the glass tubes 706 into the fractionating unit. Subsequently, the inventors injected buffer, which contained 2 kbp of DAN, from the reservoir into the liquid sump. The inventors had previously treated the DNA molecules with fluorescent dye YOYO-1 manufactured by Molecular Probe Corporation.

The inventors inserted platinum wires through the glass tubes into the liquid sumps, and applied 60 volts between the platinum wires. Then, the sample started the migration through the electrophoresis, and the inventors measured the migration speed. In detail, the amount of fluorescence was a thousand times increased by using a fluorescence microscope, and produced an image on an image intensifier manufactured by Hamamatsu Photonics Corporation. Thus, the individual DNA molecules were traced on the screen, and determined the migration speed. The inventors repeated the migration through the electrophoresis for 2 kbp of DNA, and determined the mean migration speed.

The inventors further repeated the migration through the electrophoresis for 5 kbp of DAN and 10 kbp of DNA, and determined the mean migration speed for these samples. In detail, the inventors prepared a hundred DNA molecules of 5 kbp and a hundred DNA molecules of 10 kbp for precisely investigating a statistical tendency. The DNA molecules were treated as similar to the DNA molecules of 2 kbp, and the migration speed was measured as similar to that of the DNA molecules of 2 kbp.

Figure 56:
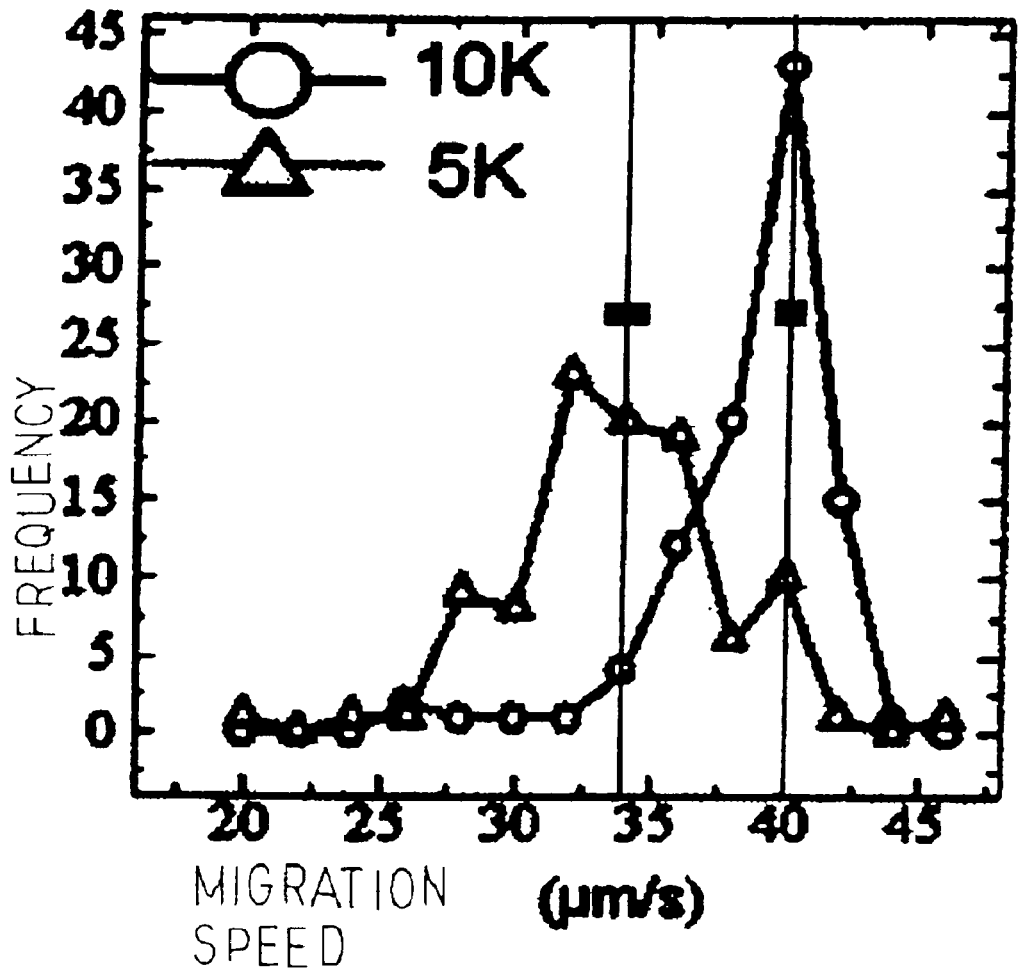
FIG. 56 is a graph showing dispersion of migration speed of DNA molecules.
Figure 5:
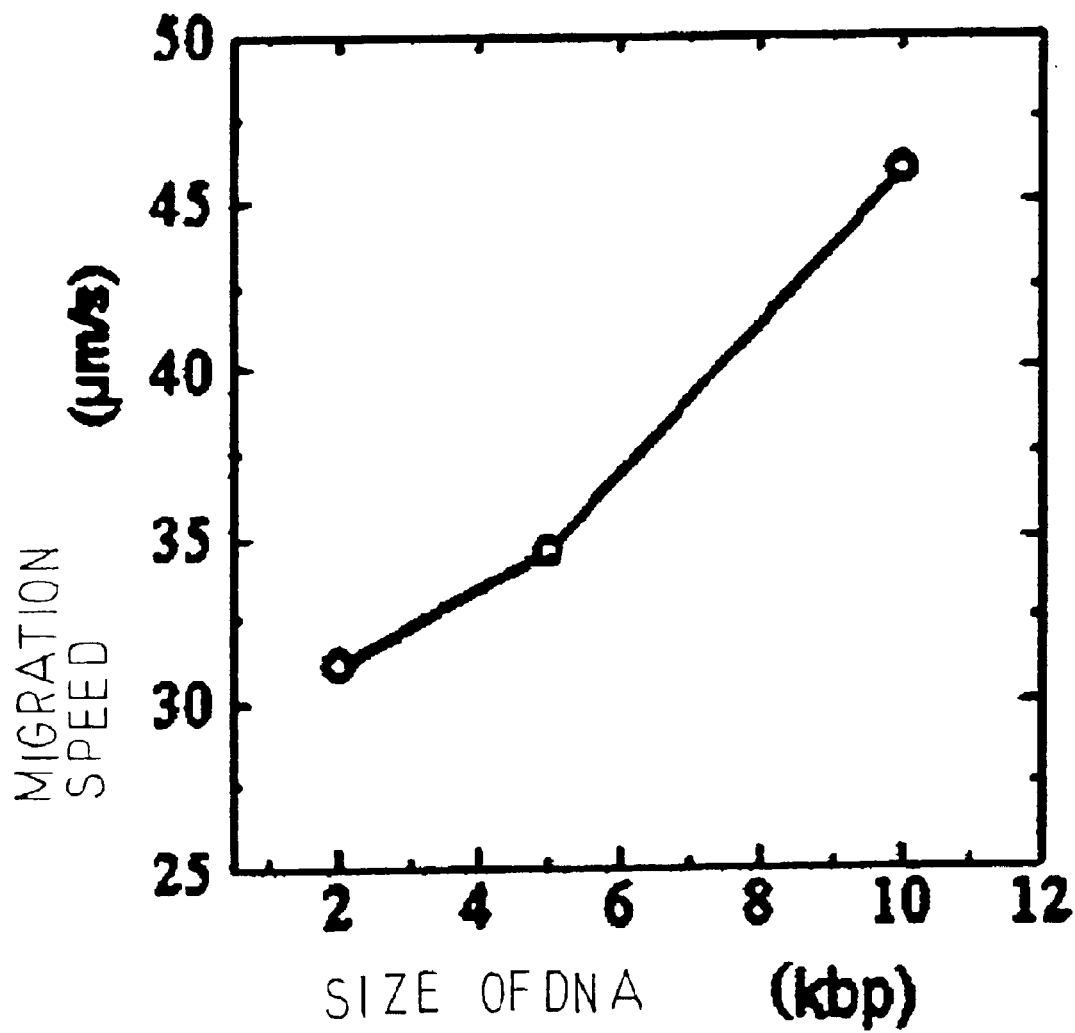

The inventors plotted the values of migration speed in FIG. 56. The dispersion was discriminative between the DNA molecules of 10 kbp and the DNA molecules of 5 kbp. From FIG. 56, the inventors determined that the mean migration speed was 40 microns per second for DNA molecules of 10 kbp and 34 microns per second for DNA molecules of 5 kbp.

The inventors plotted the mean migration speed in FIG. 56. From FIG. 56, it was understood that the DNA molecules were migrated at different values of speed depending upon the size thereof. In other words, the fractionating unit introduced a time lug in the migration through the fractionating passage, and the value of time lug was dependent on the size of the DNA molecules. Thus, the inventors confirmed that the sample was fractionated into fractions different in size by using the apparatus according to the present invention.

Although the DNA molecules of 5 kbp and the DNA molecules of 10 kbp were widely dispersed in FIG. 56, it was considered that the apparatus according to the present invention exhibited a high resolution. As well known to persons skilled in the art, the deviation of the peak was reduced in proportional to $1/N^{1/2}$ where N was the number of molecules to be traced. This was known as "center limit theorem". In general, a band, which was formed through the electrophoresis, contained several hundreds thousand DNA molecules, i.e., $10^7$ DNA molecules. If the trace was carried out for the DNA molecules of the band, the deviation of peak was reduced to $1/100000^{1/2}$, i.e., only 0.003 of the deviation of a hundred DNA molecules. This meant that the peak was quite sharp. In other words, the fractionating apparatus according to the present invention achieved a high resolution.

The present inventors accurately determined the holding time of the peak. The buffer containing the DNA molecules of 10 kbp and buffer containing the DNA molecules of 5 kbp were used. The holding time was 995 seconds for the DNA molecules of 10 kbp and 1170 seconds for the DNA molecules of 5 kbp (see table 1). Thus, DNA molecules different in size were separated through the migration along the fractionating passage of the sample.

TABLE 1

| Sample | Peak Holding Time (seconds) | Difference between Peak Holding Times (seconds) |
| --- | --- | --- |
| 10 kbp | 995 | 175 |
| 4 kbp | 1170 | |

The inventors compared the performance of the sample with those of the bio-analyzer manufactured by Agilent Technologies Corporation. The bio-analyzer had a fractionating passage of 14 millimeters long. The bio-analyzer exhibited the performance summarized in table 2.

TABLE 2

| Sample | Peak Holding Time (seconds) | Difference between Peak Holding Times (seconds) |
| --- | --- | --- |
| 10 kbp | 81 | |
| 5 kbp | 77 | 4 |
| 3 kbp | 75 | 2 |
| 2 kbp | 73 | 2 |

The present inventors fabricated another sample, which had the fractionating passage of 2.8 millimeters long, through the process described hereinbefore. Using the sample, the inventors analyzed DNA molecules of 10 and DNA molecules of 5 kbp, and summarized the results in table 3.

TABLE 3

| Sample | Peak Holding Time (seconds) | Difference between Peak Holding Times (seconds) |
| --- | --- | --- |
| 10 kbp | 70 | 12 |
| 5 kbp | 82 | |

Comparing table 2 with table 3, it was understood that the apparatus according to the present invention introduced time lug, i.e., 12 seconds longer than the time lug, i.e., 2–4 seconds introduced by the bio-analyzer. Moreover, the bio-analyzer required the fractionating passage of 14 millimeters for the fractionation. On the other hand, the sample according to the present invention required the fractionating passage shorter than that of the bio-analyzer. Moreover, when the DNA molecules equal to 10 kbp or greater than it were fractionated through the bio-analyzer, the fractionating passage tended to be clogged with the large-sized DNA molecules. However, the sample was free from the clogging by virtue of the pass among the pillar patches. The inventors concluded that the apparatus according to the present invention was superior to the bio-analyzer.

As will be appreciated from the foregoing description, the path for large-sized microstructures such as, for example, large-sized molecules is formed among the colonies of microbodies, i.e., pillar patches in the fractionating passage formed in the apparatus according to the present invention. The large-sized microstructures are migrated through the path, and the small-sized microstructures are trapped in the pillar patches. This results in the fractionation into fractions different in size without clogging.

Resolution

The present inventors further investigated the fractionation characteristics of the fractionating apparatus according to the present invention. The inventors fabricated a sample of the fractionation apparatus. The sample was fabricated on a chip. A fractionating passage was formed in the chip, and was 42 millimeters in length and 80 microns in width. A feed passage was further formed in the chip, and was 18 millimeters in length and 40 microns in width. The feed passage crossed the fractionating passage.

Colonies of pillars, i.e., pillar patches were formed in the fractionating passage. The pillars patches occupied an area in the fractionating passage, and the occupation area extended from a certain point 30 microns spaced from the crossing point between the fractionating passage and the feed passage through 5.6 millimeters. The pillar patches were arranged as shown in FIG. 22. The pillars were like walls, and were 0.4 micron in height and 3 microns in length. The pillars of each patch were arranged at intervals of 700 nanometers like a ladder. The adjacent pillar patches were spaced by 1200 nanometers. The pillars were formed through the electron beam lithography and dry etching.

The present inventors prepared three sorts of DNA molecules different in size, i.e., 2 kbp, 5 kbp and 10 kbp, and marked the three sorts of DNA molecules with the fluorescent dye YOYO-1. The different in size among the three sorts of DNA molecules was large enough to be discriminable from one another on the basis of the strength of fluorescence. The present inventors mixed the three sorts of DNA molecules so as to obtain sample to be fractionated.

The present inventors put the sample into one end of the feed passage, and applied −50 volts to the one end and +30 volts to the other end of the feed passage. A piece of sample entered the fractionating passage at the crossing point. Since −40 volts had been applied to both ends of the fractionating passage, the piece of sample was kept at the crossing point. Subsequently, the potential difference applied between the feed passage was inverted for 0.5 second. Then, the piece of sample was partially attracted backward so that the piece of sample was reduced in width. Finally, the present inventors applied plied −15 volts to both ends of the feed passage, −10 volts to the end of the fractionating passage close to the crossing point and 0 volt to the other end of the fractionating passage. The piece of sample was introduced into the fractionating passage. However, any piece of sample was not introduced from the feed passage to the fractionating passage.

The piece of sample was migrated through the fractionating passage, and was fractionated into three bands in the pillar patches. The present inventors measured the amount of fluorescence at 1 millimeter downstream from the crossing point between the feed passage and the fractionating passage. The present inventors used a fluorescence microscope. When the DNA molecules, which had been marked with the fluorescent dye, were excited under radiation from a fluorescent lamp, the DNA molecules generated fluorescence, and the amount of fluorescence was dependent on the length of the DNA molecules. A photo-multiplexer had been attached to the fluorescent microscope, and was sold by Hamamatsu Photonics Corporation as H7467. The images of the bands of DNA molecules in the field were split through a half-mirror. The images were directly obserbed by the inventors, and were incident on the photo-multiplexer. The present inventors measured the amount of fluorescence with the photo-multiplexer, and specified the band just measured through the microscope. The present inventors plotted the intensity of fluorescence in FIG. 58.

Figure 58:
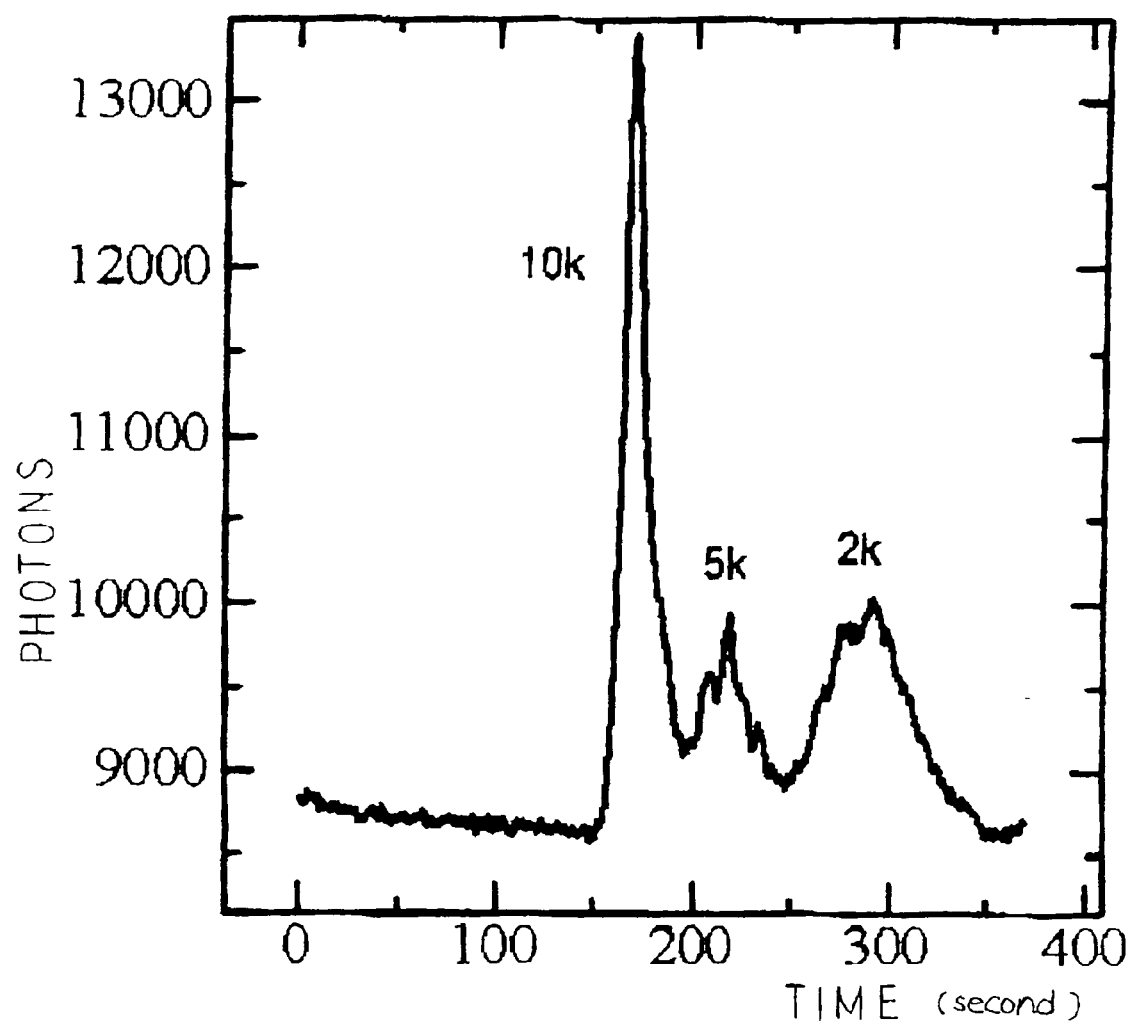
FIG. 58 is a graph showing relation between the amount of photon counted in an experiment and time.

FIG. 58 had the axis of coordinates indicative of the photons counted by the photo-multiplexer and the abscissa indicative of time. The first band reached the field of the fluorescent microscope around 160 seconds, and the photons were increased to more than 13000. The second band reached the field of the fluorescent microscope around 220 seconds, and the photons were increased to 9900. The third band reached the field of the fluorescent microscope around 290 seconds, and the photons were increased 10000. Thus, the intensity of fluorescence was peaked three times. The photons were about 8600 before the first peak, around 9100 between the first peak and the second peak and about 9000 between the second peak and the third peak. The first band, second band and third band were mainly constituted by the DNA molecules of 10 kbp, DNA molecules of 5 kbp and DNA molecules of 2 kbp, respectively. Thus, the present inventors concluded that the fractionating apparatus according to the present invention achieved high resolution.

The present inventors calculated HETP (Height Equivalent to a Theoretical Plate) on the basis of the experimental result. The HETP was an index representative of the resolution of fractionating apparatus. The lower the height, the higher the resolution. A gel filtration column used for fractionating biopolymers merely achieved 10 microns to 100 microns. The gel filtration columns "Ohpack SB-80 Series" were manufactured by Showa Denko Corporation Limited, and achieved the HETP of the order of 25 microns. High resolution columns "KF-40 Series" were also manufactured by Showa Denko Corporation Limited, and achieved the HETP of the order of 10 microns. The HETP of the fractionating apparatus according to the present invention was 4.85 microns for the DNA molecules of 2 kbp, 0.81 micron for the NDA molecules of 0.81 kbp. Thus, the present inventors confirmed that the fractionating apparatus according to the present invention was superior to the other fractionating apparatus commercially sold in the market.

Although particular embodiments of the present invention have been shown and described, it will be apparent to those skilled in the art that various changes and modifications may be made without departing from the spirit and scope of the present invention. For example, the process according to the present invention is available for the array of pillars on the substrate shown in FIG. 13.

In the above-described embodiments and modifications, the groove is corresponding to a region. Microbodies are, by way of example, pillars 125 or plate 125A. The die 106/106a or the resist mask 107a/900a/204 serves as a pattern transfer layer. The bottom surface defining the bottom of the groove is corresponding to an area or a surface area. The direction of migration is corresponding to a longitudinal direction of a region.

What is claimed is:

1. An apparatus for fractionating a sample into microstructures different in size comprising a fractionating unit including a region for permitting said sample to be migrated and at least one colony of microbodies serving as obstacles against a migration of said microstructures, formed in an area of said region and defining a labyrinth for trapping small-sized microstructures so that a remaining area of said region serves as a path for large-sized microstructures.

2. The apparatus as set forth in claim 1, in which paths are defined in said labyrinth, and have a width narrower than a width of said path for said large-sized microstructures.

3. The apparatus as set forth in claim 1, in which another colony of micro-bodies is further formed in said region, and the gap between said at least one colony of microbodies and said another colonies of microbodies forms part of said path for said large-sized microstructures.

4. The apparatus as set forth in claim 3, in which paths are defined in said labyrinth, and have a width narrower than a width of said path for said large-sized microstructures.

5. The apparatus as set forth in claim 3, in which said part of said path is directed to a certain direction crossing a longitudinal direction of said region.

6. The apparatus as set forth in claim 1, in which said microbodies in said at least one colony are spaced by regular intervals.

7. The apparatus as set forth in claim 1, in which a density of said micro-bodies is increased in said at least one colony in a direction in which said sample is migrated.

8. The apparatus as set forth in claim 1, in which a density of said micro-bodies is decreased in said at least one colony in a direction in which said sample is migrated.

9. The apparatus as set forth in claim 1, in which plural colonies of micro-bodies are further formed in said region, and said plural colonies of micro-bodies and said at least one colony of microbodies form at least two giant colonies spaced from one another by a gap forming a part of said path.

10. The apparatus as set forth in claim 9, in which a gap between adjacent two colonies selected from said plural colonies and said at least one colony is narrower than said gap between said at least two giant colonies and wider than a gap between adjacent two microstructures selected from said at least one colony and said plural colonies.

11. The apparatus as set forth in claim 1, in which paths are defined in said labyrinth, and have a width adjusted to 1–10 microns for separating cells from other components of said sample, 100–1000 nanometers for separating fragments of cell membranes and organelles from cytosol and 1–100 nanometers for sorting soluble fraction of broken cells into high molecule weight components containing DNA, RNA, proteins and sugar chains and low molecular weight components containing steroid and grape sugar.

12. The apparatus as set forth in claim 1, in which said microbodies are pillars projecting from said area.

13. The apparatus as set forth in claim 12, in which said pillars are flared from tops thereof toward bases thereof.

14. The apparatus as set forth in claim 12, in which said pillars have a configuration selected from the group consisting of a circular cylinder, a cylindroid, a cone, an elliptical cone, a pyramid and a prism.

15. The apparatus as set forth in claim 12, in which said pillars have hydrophilic surface portions, respectively.

16. The apparatus as set forth in claim 15, in which cores of said pillars inside said surface portions and said surface portions are respectively made of certain material and oxide of said certain material, respectively.

17. The apparatus as set forth in claim 16, in which said pillars are closely arranged so that said surface portions are sharply merged with one another at the bottoms of valleys among said pillars.

18. The apparatus as set forth in claim 1, in which said fractionating unit further includes wall portions defining a feeding sump connected to one end of said region and walls portions defining a recovery sump connected to the other end of said region so that said sample is migrated from said feeding sump through said region to said recovery sump.

19. The apparatus as set forth in claim 1, in which at least one row of micro-bodies is formed in front of said at least one colony of microbodies so that said sample is shaped into a band at said row of microbodies before entry into said at least one colony of microbodies.

20. The apparatus as set forth in claim 1, in which said fractionating unit further includes at least one sparse colony of microstructures lower in density than said at least one colony, and said at least one sparse colony is provided in front of said at least one colony of microbodies so that said sample is shaped into a band before entry into said at least one colony of microbodies.

21. The apparatus as set forth in claim 20, in which said sparse colony is replaced with a slit between said at least one colony of microbodies and another colony of microbodies.

22. The apparatus as set forth in claim 1, in which said region is a bottom of a groove defined by walls.

23. The apparatus as set forth in claim 22, in which said walls are hydrophilic.

24. The apparatus as set forth in claim 22, in which said groove is closed with a cover plate, and a gap between said bottom and said cover plate is less than a height of said microbodies so that another path is defined between said microbodies and said cover plate for said large-sized microstructures.

25. The apparatus as set forth in claim 1, further comprising a sample accelerator exerting a force on said sample so as to forcibly migrate said sample through said region.

26. The apparatus as set forth in claim 25, in which said sample accelerator includes an electrode provided at one end of said region, another electrode provided at the other end of said region and a biasing unit applying a potential difference between said electrode and said another electrode for creating an electric field over said region.

27. The apparatus as set forth in claim 25, in which said sample accelerator includes a pressurizing unit supplying high-pressure buffer solution to one end portion of said region so as to forcibly flow said sample together with said high-pressure buffer solution from said one end to the other end of said region.

28. The apparatus as set forth in claim 25, in which said sample accelerator includes a holding colony of microbodies located between said at least one colony of microbodies and a sample feeding port and larger in density than said at least one colony of microbodies, a quantitative colony of microbodies located between said holding colony and said sample feeding port and smaller in density than said at least one colony, a holding space provided between said holding colony and said quantitative colony, an introducing colony of microbodies located between said holding colony and a buffer feeding port and equal in density to said at least one colony and holding spaces provided between said at lest one colony and said holding colony and between said holding colony and said introducing colony.

* * * * *

UNITED STATES PATENT AND TRADEMARK OFFICE
CERTIFICATE OF CORRECTION

PATENT NO. : 6,881,315 B2
APPLICATION NO. : 10/207852
DATED : April 19, 2005
INVENTOR(S) : Iida et al.

It is certified that error appears in the above-identified patent and that said Letters Patent is hereby corrected as shown below:

Col. 3, line 54, delete "view" and insert --views--.

Col. 4, line 7, delete "view" and insert --views--.

Col. 4, line 15, delete "part" and insert --parts--.

Col. 4, line 26, delete "photon" and insert --photons--.

Col. 4, line 37, delete "comprises" and insert --comprise--.

Col. 5, line 11, delete "become" and insert --becomes--.

Col. 6, line 19, delete "ed".

Col. 7, line 32, delete "cable" and insert --able--.

Col. 7, line 54, delete "stays" and insert --stay--.

Col. 8, line 8, after "gathers" insert --the--.

Col. 9, line 64, delete "through-away" and insert --throw away--.

Col 12, line 10, delete "FIGS" and insert --FIG--.

Col. 16, line 47, delete "flows" and insert --flow--.

Col. 16, line 53, delete "flows" and insert --flow--.

Col. 17, line 42, delete "sages".

Col. 17, line 52, delete "D, Φ, D, d and p" and insert --D, Φ, d and p--.

Col. 18, line 5, delete "crows" and insert --rows--.

Col. 18, line 24, delete "forms" and insert --form--.

Col. 19, line 14, delete "pitches" and insert --pillars--.

Col. 20, line 20, delete "stays" and insert --stay--.

Col. 20, line 23, delete "enhances" and insert --enhance--.

UNITED STATES PATENT AND TRADEMARK OFFICE
CERTIFICATE OF CORRECTION

PATENT NO. : 6,881,315 B2
APPLICATION NO. : 10/207852
DATED : April 19, 2005
INVENTOR(S) : Iida et al.

It is certified that error appears in the above-identified patent and that said Letters Patent is hereby corrected as shown below:

Col. 21, line 14, delete "sage".

Col. 21, line 45, delete "with" and insert --width--.

Col. 22, line 4, delete "membrare" and insert --membrane--.

Col. 22, line 5, delete "limited" and insert --Limited--.

Col. 22, line 34, delete "reaches" and insert --reach--.

Col. 22, line 36, delete "follows" and insert --follow--.

Col. 23, line 49, delete "Caron" and insert --:Carbon--.

Col 23, line 57, delete "nanoporns" and insert --nanohorns--.

Col. 24, line 51, delete "110. The" and insert --110, the--.

Col. 24, line 53, delete "shows" and insert --show--.

Col. 25, line 44, delete "hie" and insert --die--.

Col. 26, line 11, delete "oxidzed" and insert --oxidized--.

Col. 27, line 29, delete "betwene" and insert --between--.

Col. 27, line 50, delete "in".

Col. 27, line 55, delete "FIGS" and insert --FIG--.

Col. 29, line 3, delete "381 and 391" and insert --38I and 39I--.

Col. 29, line 32, delete "herienbefore" and insert --hereinbefore--.

Col. 29, line 60, delete "photogrpahs" and insert --photographs--.

Col. 29, line 60, delete "oxidatoin" and insert --oxidation--.

Col. 30, line 30, delete "in".

Col. 32, line 8, delete "2 kbp of DAN" and insert --2 kbp of DNA--.

UNITED STATES PATENT AND TRADEMARK OFFICE
CERTIFICATE OF CORRECTION

PATENT NO. : 6,881,315 B2
APPLICATION NO. : 10/207852
DATED : April 19, 2005
INVENTOR(S) : Iida et al.

It is certified that error appears in the above-identified patent and that said Letters Patent is hereby corrected as shown below:

Col. 32, line 25, delete "5 kbp of DAN" and insert --5 kbp of DNA--.

Col. 33, line 33, after "10" insert --kbp--.

Col. 34, line 26, delete "different" and insert --difference--.

Col. 34, line 41, delete "plied".

Col. 34, line 62, delete "obserbed" and insert --observed.--.

Col. 35, line 34, delete "NDA" and insert --DNA--.

Col. 38, Claim 28, line 22, delete "lest" and insert --least--.

Signed and Sealed this

Thirtieth Day of September, 2008

JON W. DUDAS
*Director of the United States Patent and Trademark Office*